(12) United States Patent
Li et al.

(10) Patent No.: US 11,597,954 B2
(45) Date of Patent: Mar. 7, 2023

(54) BIOPRODUCTION OF PHENETHYL ALCOHOL, ALDEHYDE, ACID, AMINE, AND RELATED COMPOUNDS

(71) Applicant: National University of Singapore, Singapore (SG)

(72) Inventors: Zhi Li, Singapore (SG); Shuke Wu, Singapore (SG); Yi Zhou, Singapore (SG); Benedict Ryan Lukito, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/615,689

(22) PCT Filed: May 23, 2018

(86) PCT No.: PCT/SG2018/050250
§ 371 (c)(1),
(2) Date: Nov. 21, 2019

(87) PCT Pub. No.: WO2018/217168
PCT Pub. Date: Nov. 29, 2018

(65) Prior Publication Data
US 2020/0232000 A1    Jul. 23, 2020

(30) Foreign Application Priority Data

May 23, 2017  (SG) .......................... 10201704182Q

(51) Int. Cl.
| | | |
|---|---|---|
| *C12P 13/00* | (2006.01) | |
| *C12N 9/04* | (2006.01) | |
| *C12N 9/02* | (2006.01) | |
| *C12N 9/10* | (2006.01) | |
| *C12N 9/12* | (2006.01) | |
| *C12N 9/88* | (2006.01) | |
| *C12N 9/90* | (2006.01) | |
| *C12P 7/22* | (2006.01) | |
| *C12P 7/24* | (2006.01) | |
| *C12P 7/54* | (2006.01) | |

(52) U.S. Cl.
CPC .......... *C12P 13/001* (2013.01); *C12N 9/0006* (2013.01); *C12N 9/0008* (2013.01); *C12N 9/0071* (2013.01); *C12N 9/1085* (2013.01); *C12N 9/1096* (2013.01); *C12N 9/1205* (2013.01); *C12N 9/88* (2013.01); *C12N 9/90* (2013.01); *C12P 7/22* (2013.01); *C12P 7/24* (2013.01); *C12P 7/54* (2013.01); *C12Y 101/01001* (2013.01); *C12Y 101/01282* (2013.01); *C12Y 102/01003* (2013.01); *C12Y 114/14011* (2013.01); *C12Y 205/01054* (2013.01); *C12Y 206/01057* (2013.01); *C12Y 207/01071* (2013.01); *C12Y 402/01051* (2013.01); *C12Y 503/99007* (2013.01)

(58) Field of Classification Search
CPC ...... C12N 1/005; C12N 9/006; C12N 9/0008; C12N 9/0071; C12N 9/1085; C12N 9/1096; C12N 9/1205; C12N 9/88; C12N 9/90; C12N 15/52; C12Y 114/14011; C12Y 503/99007; C12Y 101/01001; C12Y 101/01282; C12Y 102/01003; C12Y 205/01054; C12Y 206/01057; C12Y 207/01071; C12Y 402/01051; C12P 13/001; C12P 7/22; C12P 7/24; C12P 7/54; C12P 13/22
See application file for complete search history.

(56) References Cited

U.S. PATENT DOCUMENTS

| | | | | |
|---|---|---|---|---|
| 8,270,321 B1 * | 9/2012 | Zhang | .................. | H04W 28/06 370/280 |
| 2010/0069607 A1 * | 3/2010 | MacMillan | ............ | C07K 9/001 530/322 |

(Continued)

FOREIGN PATENT DOCUMENTS

| | | | | |
|---|---|---|---|---|
| WO | WO-2012178126 A1 * | 12/2012 | ......... | C12N 15/8243 |
| WO | WO-2014189469 A1 * | 11/2014 | ........... | C12N 9/0071 |

OTHER PUBLICATIONS

Liu et al. (2016) Asymmetric bio-epoxidation catalyzed with the styrene monooxygenase from *Pseudomonas* sp. LQ26, Bioresour. Bioproc., vol. 10, pp. 1-7.*

(Continued)

*Primary Examiner* — Iqbal H Chowdhury
(74) *Attorney, Agent, or Firm* — Osha Bergman Watanabe & Burton LLP

(57) ABSTRACT

This invention relates to the bioproduction of substituted or unsubstituted phenylacetaldehyde, 2-phenylethanol, phenylacetic acid or phenylethylamine by subjecting a starting material comprising glucose, L-phenylalanine, substituted L-phenylalanine, styrene or substituted styrene to a plurality of enzyme catalyzed chemical transformations in a one-pot reaction system, using recombinant microbial cells overexpressing the enzymes. To produce phenylacetaldehyde from styrene, the cells are modified to overexpress styrene monooxygenase (SMO) and styrene oxide isomerase (SOI). To produce phenylacetic acid from styrene, SMO, SOI and aldehyde dehydrogenase are overexpressed. Alternatively, to produce 2-phenylethanol, SMO, SOI and aldehyde reductase or alcohol dehydrogenase are overexpressed, while to produce phenylethylamine, SMO, SOI and transaminase are overexpressed.

10 Claims, 16 Drawing Sheets
Specification includes a Sequence Listing.

(56) References Cited

U.S. PATENT DOCUMENTS

| | | | |
|---|---|---|---|
| 2014/0011871 A1* | 1/2014 | Rockhill | A61K 31/27 514/481 |
| 2014/0067084 A1* | 3/2014 | Soss | A61F 2/80 623/34 |
| 2015/0056675 A1* | 2/2015 | Muramatsu | C12Y 601/00 435/254.2 |
| 2015/0225751 A1* | 8/2015 | Yan | C12Y 402/99 435/142 |
| 2016/0097063 A1* | 4/2016 | Li | C12N 9/14 435/189 |
| 2016/0186217 A1* | 6/2016 | Oelschlagel | C12N 1/20 435/146 |
| 2016/0340699 A1* | 11/2016 | Gonzalez | C12N 15/52 |
| 2017/0067084 A1* | 3/2017 | Li | C12N 9/0069 |

OTHER PUBLICATIONS

Panke et al. (1998) Towards a Biocatalyst for (S)-Styrene Oxide Production: Characterization of the Styrene Degradation Pathway of *Pseudomonas* sp. Strain VLB120, Appl. Environ. Microbiol., vol. 64, pp. 2032-2043.*

Rodriguez et al. (2014) Engineering *Escherichia coli* to overproduce aromatic amino acids and derived compoundsMicrob, Cell Factor. vol. 13, issue 216, pp. 1-15.*

Sinba et al. (2015) Alignment behaviors of short peptides provide a roadmap for functional profiling of metagenomic dataBMC Genomics, vol. 16, issue 1080, pp. 1-12.*

Gassner G.T. (2019) "The styrene monooxygenase system", Chapter 16, in Methods in Enzymology, vol. 620, pp. 423-453.*

Wang et al. (2013) Mutations in the Hedgehog Pathway Genes SMO and PTCH1 in Human Gastric Tumors, PLOS one, vol. 8, issue 1, e54415, pp. 1-8.*

Panke et al. (1998) Towards a Biocatalyst for (S)-Styrene Oxide Production: Characterization of the Styrene Degradation Pathway of *Pseudomonas* sp. Strain VLB120, Appl. Environ. Microbiol., vol. 64, No. 6, pp. 2032-2043.*

Ref Styrene oxide isomerase (2006) https://www.ncbi.nlm.nih.gov/protein/O50216, pp. 1-2.*

Kim et al. (2015) Current Technologies and Related Issues for Mushroom Transformation,) Microbiology, vol. 43, No. 1, pp. 1-8.*

International Search Report issued in corresponding International Application No. PCT/SG2018/050250 dated Aug. 24, 2018 (8 pages).

Written Opinion issued in corresponding International Application No. PCT/SG2018/050250 dated Aug. 24, 2018 (10 pages).

International Preliminary Report on Patentability in corresponding Application No. PCT/SG2018/050250 dated Dec. 5, 2019 (12 pages).

Toda, Hiroshi and Nobuya Itoh. Isolation and characterization of styrene metabolism genes from styrene-assimilating soil bacteria *Rhodococcus* sp. ST-5 and ST-10. Journal of Bioscience and Bioengineering. vol. 113. No. 1. Oct. 12, 2011 [Retrieved Aug. 1, 2018], pp. 12-19 (8 pages).

Oelschlägel, Michel et al. Production of a recombinant membrane protein in an *Escherichia coli* strain for the whole cell biosynthesis of phenylacetic acids. Biotechnology Reports. May 11, 2015. vol. 7, pp. 38-43 [Retrieved Aug. 1, 2018]. url: https://dx.doi.org/10.1016/j.btre.2015.05.002 (6 pages).

Uthoff, Florian et al. Formal Enantioselective Hydroamination of Non-Activated Alkenes: Transformation of Styrenes into Enantiomerically Pure 1-Phenylethilamines in Chemoenzymatic One-Pot Synthesis. Chem Cat Chem. Nov. 29, 2016, vol. 9, No. 4, pp. 555-558 [Retrieved Aug. 8, 2018] (4 pages).

Klatte, Stephanie and Volker F. Wendisch. Redox self-sufficient whole cell biotransformation for amination of alcohols. Bioorganic & Medicinal Chemistry. May 17, 2014. vol. 22, No. 20, pp. 5578-5585 [Retrieved Aug. 8, 2018] (8 pages).

Itch, Nobuya et al. Characterization of Styrene Oxide Isomerase, a Key Enzyme of Styrene and Styrene Oxide Metabolism in *Corynehacterium* sp. Bioscience, Biotechnology, and Biochemistry. Jun. 12, 1997. vol. 61, No. 12, pp. 2058-2062 [Retrieved Aug. 1, 2018] (6 pages).

Liu, Shuang-Ping et al. Production of L-phenylalanine from glucose by metabolic engineering of wild type *Escherichia coli* W3110. Process Biochemisty. Feb. 24, 2013. vol. 48, No. 3, pp. 413-419 [Retrieved Aug. 1, 2018] (7 pages).

Wu, Shuke et al. Regio- and Steroselective Oxidation of Styrene Derivatives to Arylalkanoic Acids via One-Pot Cascade Biotransformations. Advanced Synthesis & Catalysis. May 26, 2017. vol. 359, No. 12, pp. 2132-2141 [Retrieved Aug. 1, 2018] (10 pages).

Wu, Shuke et al. Biocatalytic Formal Anti-Markovnikov Hydroamination and Hydration of Aryl Alkenes. ACS Catalysis. Jun. 29, 2017. vol 7, No. 8, pp. 5225-5233 [Retrieved Aug. 1, 2018] (9 pages).

Lorenzo, Paloma et al. Design of catabolic cassettes for styrene biodegradation. Antonie Van Leeuwenhoek. Jul. 31, 2003. vol. 84, No. 1, pp. 17-24 [Retrieved Aug. 1, 2018] (8 pages).

Koma, Daisuke et al. Production of Aromatic Compounds by Metabolically Engineered *Escherichia coli* with an Expanded Shikimate Pathway. Applied Environmental Biology. Jun. 29, 2012. vol. 78, No. 17, pp. 6203-6216 [Retrieved Aug. 1, 2018] (14 pages).

Panke, Sven et al. Towards a Biocatalyst for (S)-Styrene Oxide Production: Characterization of the Styrene Degradation Pathway of *Pseudomonas* sp. Strain VLB120. Applied and Environmental Microbiology. Jun. 30, 1998. vol. 64, No. 6, pp. 2032-2043 [Retrieved Aug. 1, 2018] (12 pages).

Etschmann, M.M.W. et al., "Biotechnological production of 2-phenylethanol", Mini-Review, Appl Microbiol Biotechnol., Springer-Verlag, vol. 59, Apr. 2002 (8 pages).

Hua, Dongliang and Ping Xu, "Recent advances in biotechnological productions of 2-phenylethanol", Biotechnology Advances, ScienceDirect, Elsevier Inc., vol. 29, May 2011, pp. 654-660 (7 pages).

Kim, Bosu et al., "Metabolic Engineering of *Saccharomyces cerevisiae* for the Production of 2-Phenylethanol Via Ehrlich Pathway", Biotechnology and Bioengineering, Wiley Periodicals, Inc., vol. 111, No. 1, Jan. 2014, pp. 115-124 (10 pages).

Zhou, Yi et al., "Cascade Biocatalysis for Sustainable Asymmetric Synthesis: From Biobased L-Phenylalanine to High-Value Chiral Chemicals", Biotransformations, Angewandte Chemie: International Edition, Wiley Online Library, Wiley-VCH Veriag GmbH & Co. KGaA, vol. 55, 2016, pp. 11647-11650 (4 pages).

Kaulmann, Ursula et al., "Substrate spectrum of w-transaminase from Chromobacterium violaceum DSM30191 and its potential for biocatalysis", Enzyme and Microbial Technology, ScienceDirect, Elsevier Inc., vol. 41, May 2007, pp. 628-637 (10 pages).

Könst, Paul et al., "Enantioselective Oxidation of Aldehydes Catalyzed by Alcohol Dehydrogenase", Enzyme Catalysis, Angewandte Communications, Wiley Online Library, Wiley-VCH Verlag GmbH & Co., KGaA, vol. 51, pp. 9914-9917 (4 pages).

Kunjapur, Aditya M. et al., "Synthesis and Accumulation of Aromatic Aldehydes in an Engineered Strain of *Escherichia coli*", Journal of the American Chemical Society, ACS Publications, American Chemical Society, vol. 136, Jul. 2014, pp. 11644-11654 (11 pages).

Stark, D. et al., "Inhibition aspects of the bioconversion of L-phenylalanine to 2-phenylethanol by *Saccharomyces cerevisiae*", Enzyme and Microbial Technology, Elsevier Science Inc., vol. 32, Sep. 2003, pp. 212-223 (12 pages).

Lucchini, J.J. et al., "Antibacterial Activity of Phenolic Compounds and Aromatic Alcohols", Res. Microbiol., Institut Pasteur/Elsevier, vol. 141, 1990, pp. 499-510 (12 pages).

Mei, Jianfeng et al., "Enhanced biotransformation of L-phenylalanine to 2-phenylethanol using an in situ product adsorption technique", Process Biochemistry, ScienceDirect, Elsevier Ltd., vol. 44, Apr. 2009, pp. 886-890 (5 pages).

Lukito, Benedict Ryan et al., "One-Pot Production of Natural 2-Phenylethanol from L-Phenylalanine via Cascade Biotransformations", ChemCatChem: Full Papers, Wiley Online Library, Wiley-VCH Veriag GmbH & Co. KGaA, vol. 11, 2019, pp. 831-840 (10 pages).

Sekar, Balaji Sundara et al., "Production of Natural 2-Phenylethanol from Glucose or Glycerol with Coupled *Escherichia coli* Strains

(56) References Cited

OTHER PUBLICATIONS

Expressing L-Phenylalanine Biosynthesis Pathway and Artificial Biocascades", ACS Sustainable Chemistry & Engineering, ACS Publications, American Chemical Society, vol. 7, Jun. 2019, pp. 12231-12239 (9 pages).

Wu, Shuke et al., "Enantioselective trans-Dihydroxylation of Aryl Olefins by Cascade Biocatalysis with Recombinant *Escherichia coli* Coexpressing Monooxygenase and Epoxide Hydrolase", ACS Catalysis, ACS Publications, American Chemical Society, vol. 4, Dec. 2013, pp. 409-420 (12 pages).

Wu, Shuke et al., "Highly regio- and enantioselective multiple oxy- and amino-functionalizations of alkenes by modular cascade biocatalysis", Nature Communications, DOI: 10.1038/ncomms11917, Jun. 2016 (13 pages).

Tieman, Denise M. et al., "Tomato phenylacetaldehyde reductases catalyze the last step in the synthesis of the aroma volatile 2-phenylethanol", Phytochemistry, ScienceDirect, Elsevier Ltd., vol. 68, Jun. 2007, pp. 2660-2669 (10 pages).

Ferrández, Abel et al., "Molecular characterization of PadA, a phenylacetaldehyde dehydrogenase from *Escherichia coli*", FEBS 18373, FEBS Letters, Federation of European Biochemical Societies, vol. 406, 1997, pp. 23-27 (5 pages).

Hua, Dong-Liang et al., "Extractive Bioconversion of L-Phenylalanine to 2-Phenylethanol Using Polypropylene Glycol 1500", Asian Journal of Chemistry, vol. 25, No. 11, Apr. 2013, pp. 5951-5954 (4 pages).

Seward, Rebecca et al., "The Effects of Ethanol, Hexan-1-OL, and 2-Phenylethanol on Cider Yeast Growth, Viability, and Energy Status; Synergistic Inhibition", Journal of the Institute of Brewing, Insitute of Brewing and Distilling, vol. 102, Nov.-Dec. 1996, pp. 439-443 (5 pages).

Link, Andrew J. et al., "Methods for Generating Precise Deletions and Insertions in the Genome of Wild-Type *Escherichia coli*: Application to Open Reading Frame Characterization", Journal of Bacteriology, American Society for Microbiology, vol. 179, No. 20, Oct. 1997, pp. 6228-6237 (10 pages).

Gottesman, Susan, "Miinimizing Proteolysis in *Escherichia coli*: Genetic Solutions", Methods in Enzymology, vol. 185, 1990, pp. 119-129 (11 pages).

Wada, Ken-nosuke et al., "Codon usage tabulated from the GenBank genetic sequence data", Nucleic Acids Research, Oxford University Press, vol. 20, Supplement, 1992, pp. 2111-2118 (8 pages).

\* cited by examiner

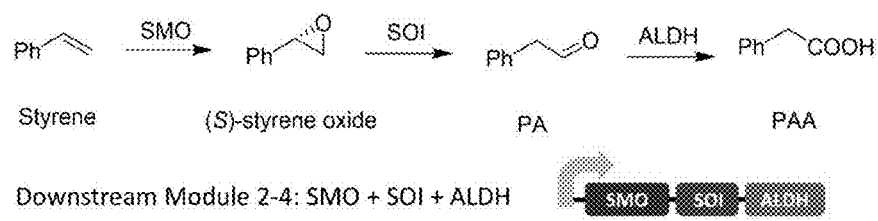
FIG. 6
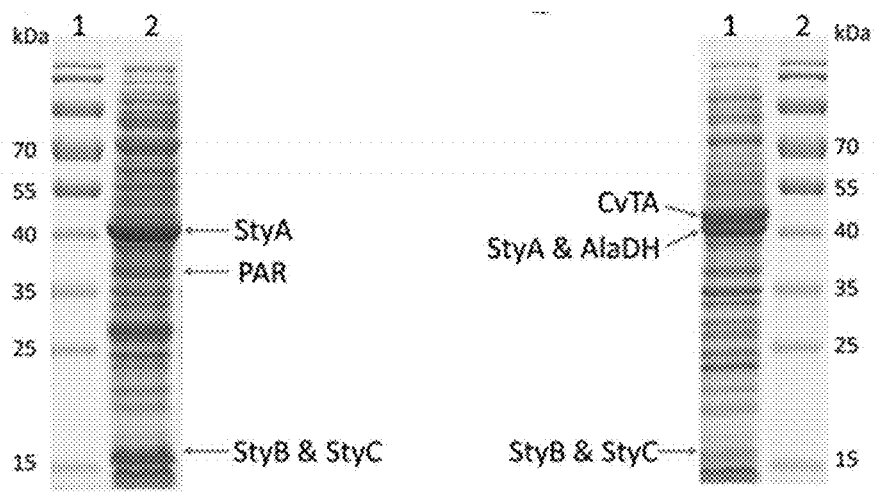
FIG. 7a                    FIG. 7b
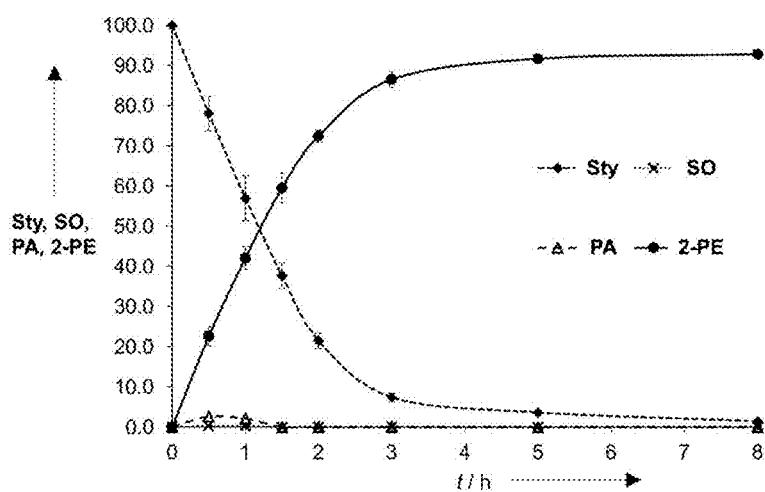
FIG. 8

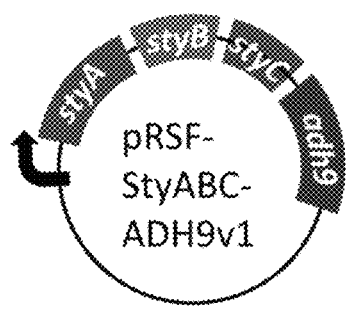
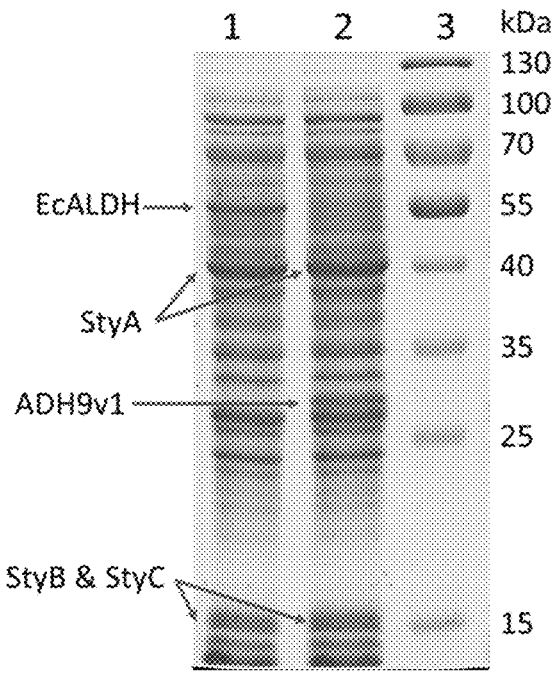
FIG. 13a
FIG. 13b
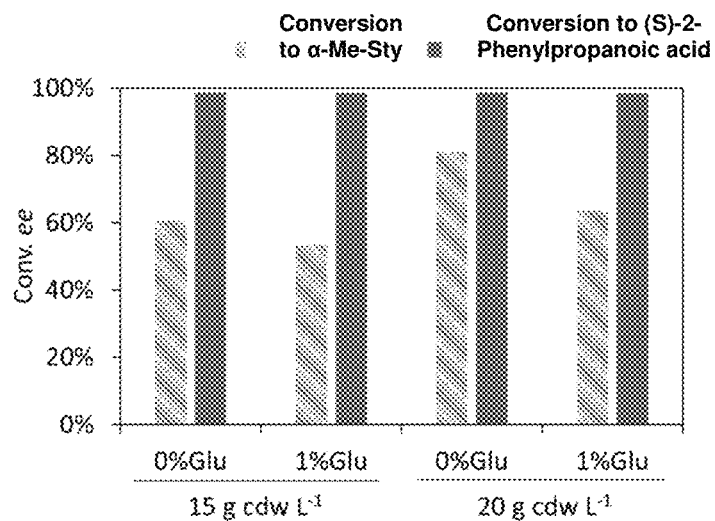
FIG. 14

US 11,597,954 B2

BIOPRODUCTION OF PHENETHYL ALCOHOL, ALDEHYDE, ACID, AMINE, AND RELATED COMPOUNDS

FIELD OF INVENTION

This invention relates to the bioproduction of useful and valuable phenethyl alcohol, aldehyde, acid, amine, and related compounds using novel biocatalysts. More particularly, the present invention provides methods of bioproduction of substituted or unsubstituted phenylacetaldehyde, 2-phenylethanol, phenylacetic acid or phenylethylamine by one or more recombinant microbial cells genetically engineered to overexpress, relative to a wild type cell, at least one enzyme, which method comprises subjecting a starting material to a plurality of enzyme-catalyzed chemical transformations in a one-pot reaction system, wherein the starting material is selected from a group comprising glucose, L-phenylalanine or substituted L-phenylalanine, styrene or substituted styrene.

BACKGROUND

2-Phenylethanol (2-PE), phenylacetaldehyde (PA), phenylacetic acid (PAA), and phenylethylamine (PEA) are widely used in cosmetic, perfume, and food industries. The current industrial methods to produce these compounds depend on traditional chemocatalysis of toxic and "dirty" petro-based chemicals, such as benzene. For food and cosmetic applications, natural 2-PE, PA, PAA, and PEA are preferred by customers. For instance, the natural 2-PE sells at about USD 1000/kg, while the traditional chemical synthesized 2-PE sells at only about USD 5/kg. However, the production process of natural 2-PE, PA, PAA, and PEA, extraction from botanical sources cannot meet the large market demand. Bioproduction of 2-PE, PA, PAA, and PEA from natural bioresources is regarded as a promising alternative way, yet the efficiency of existing bioproduction is limited due to the low efficiency of natural synthesis pathway and the toxicity of products.

2-Phenylethanol (2-PE) is a rose-like fragrance (FEMA-GRAS 2858) with an annual production of 10,000 tonnes and is mainly produced by chemical synthesis from benzene or styrene [Etschmann, M., Bluemke, W., et al., *J. Appl. Microbiol. Biotechnol.* 59: 1-8; (2002); Hua, D., Xu, P. *Biotechnol. Adv.* 29: 654-660 (2011)]. Phenylacetaldehyde (PA) (FEMA-GRAS 2874) is a valuable aroma for food and cosmetic application, and the natural PA is more preferred in these applications. Phenylacetic acid (PAA) (FEMA-GRAS 2878) possesses a honey-like odor in low concentration and thus is used in some perfumes. Phenylethylamine (PEA) is a natural monoamine alkaloid with psychoactive and stimulant effects. It has been widely used as food supplement and nutrition supplement to boost mood and mental performance.

To provide enough supply of natural 2-PE or other related compounds, biotechnological methods from natural origin were developed and the products can be considered natural. Microbial production of 2-PE has been very attractive for producing a "natural" product with high value. The natural Ehrlich pathway in some yeast was employed for microbial production (e.g., by some yeasts, fungi, and very few bacteria) of these natural compounds [Etschmann, M., Bluemke, W., et al., *J. Appl. Microbiol. Biotechnol.* 59: 1-8; (2002); Hua, D., Xu, P. *Biotechnol. Adv.* 29: 654-660 (2011)]. However, these methods only produced the desired products in low to moderate concentration. For example, baker's yeast *Saccharomyces cerevisiae* was recently engineered to produce 4.8 g/L of 2-PE from 10 g/L of Phe via the traditional Ehrlich pathway [Kim, B., Cho, B. R., Hahn, J. S. *Biotechnol. Bioeng.* 111: 115-124 (2014)].

There is a need for improved methods to produce useful and valuable "natural" phenethyl alcohol, aldehyde, acid, amine, and related compounds.

SUMMARY OF INVENTION

In this invention, novel and efficient biosynthesis pathways were engineered into microbial cells for bioproduction of 2-PE, PA, PAA, and PEA from styrene, natural products L-phenylalanine (L-Phe) and glucose, respectively. The metabolic engineering approach disclosed in the present invention can also be applied to the production of other biochemicals in *E. coli* and other microbial strains. The novel synthetic route involves 1) upstream shikimate pathway to produce L-Phe from glucose; 2) midstream deamination-decarboxylation module to convert L-Phe to styrene; 3) downstream modules to functionalize styrene to 2-PE, PA, PAA, and PEA, respectively. The downstream modules alone could be used for conversion of styrene to 2-PE, PA, PAA, and PEA. The midstream and downstream modules could be combined in one recombinant strain to directly convert biobased L-Phe to these products. By further integrated with the upstream pathway, the recombinant biocatalysts enable the fermentative production of these products from biobased glucose. In addition, ring-substituted derivatives of 2-PE, PA, PAA, and PEA were also produced from the corresponding substituted styrenes.

Thus, in a first aspect of the invention, there is provided a method for bioproduction of substituted or unsubstituted phenylacetaldehyde, 2-phenylethanol, phenylacetic acid or phenylethylamine by one or more recombinant microbial cells genetically engineered to overexpress, relative to a wild type cell, at least one enzyme, which method comprises subjecting a starting material to a plurality of enzyme-catalyzed chemical transformations in a one-pot reaction system, wherein the starting material is selected from a group comprising glucose, L-phenylalanine or substituted L-phenylalanine, styrene or substituted styrene.

In some embodiments of the first aspect of the invention, the genetically engineered cells:
(i) overexpress styrene monooxygenase and styrene oxide isomerase for generating substituted or unsubstituted phenylacetaldehyde from styrene or substituted styrene;
(ii) overexpress styrene monooxygenase, styrene oxide isomerase and an aldehyde dehydrogenase for generating substituted or unsubstituted phenylacetic acid from styrene or substituted styrene;
(iii) overexpress styrene monooxygenase, styrene oxide isomerase, an aldehyde reductase and/or an alcohol dehydrogenase for generating substituted or unsubstituted 2-phenylethanol from styrene or substituted styrene; or
(iv) overexpress styrene monooxygenase, styrene oxide isomerase and a transaminase for generating substituted or unsubstituted phenylethylamine from styrene or substituted styrene.

In some embodiments, the styrene monooxygenase comprises an amino acid sequence set forth in SEQ ID NO: 1 and 2, variants, mutants, or fragments thereof; styrene oxide isomerase comprises an amino acid sequence set forth in SEQ ID NO: 3, variants, mutants, or fragments thereof; the aldehyde dehydrogenase comprises an amino acid sequence set forth in SEQ ID NO: 4, variants, mutants, or fragments thereof; the alcohol dehydrogenase comprises an amino acid sequence set forth in SEQ ID NO: 5, variants, mutants, or fragments thereof and the transaminase is ω-transaminase comprises an amino acid sequence set forth in SEQ ID NO: 6, variants, mutants, or fragments thereof.

In some embodiments, the styrene monooxygenase is from *Pseudomonas* sp. VLB120 or its mutants, styrene oxide isomerase is from *Pseudomonas* sp. VLB120 or its mutants, the aldehyde dehydrogenase is from *Escherichia coli* or its mutants, the aldehyde reductase is from *Solanum lycopersicum* or its mutants or is YqhD from *Escherichia coli* or its mutants; the alcohol dehydrogenase is from *Saccharomyces cerevisiae* and the transaminase is ω-transaminase from *Chromobacterium violaceum* or its mutants or *Vibrio fluvialis* or its mutants.

In some embodiments, the styrene monooxygenase is encoded by a nucleic acid sequence set forth in SEQ ID NOs: 7 and 8; styrene oxide isomerase is encoded by a nucleic acid sequence set forth in SEQ ID NO: 9; the aldehyde dehydrogenase is encoded by a nucleic acid sequence set forth in SEQ ID NO: 10; the alcohol dehydrogenase is encoded by a nucleic acid sequence set forth in SEQ ID NO: 11 and the transaminase encoded by a nucleic acid sequence set forth in SEQ ID NO: 12.

It may be advantageous to provide the styrene or substituted styrene from conversion of L-phenylalanine or substituted L-phenylalanine in the same one-pot reaction system.

Accordingly, in some embodiments, the same genetically engineered cells or other genetically engineered cells produce styrene or substituted styrene from L-phenylalanine or substituted L-phenylalanine by a deamination reaction catalyzed by overexpression of an ammonia lyase and a decarboxylation reaction catalyzed by overexpression of a decarboxylase.

In preferred embodiments, the ammonia lyase is phenylalanine ammonia lyase and the decarboxylase is phenylacrylic acid decarboxylase.

In some embodiments, the phenylalanine ammonia lyase comprises an amino acid sequence set forth in SEQ ID NO: 13, variants, mutants, or fragments thereof and phenylacrylic acid decarboxylase comprises an amino acid sequence set forth in SEQ ID NO: 14, variants, mutants, or fragments thereof.

In some embodiments, the phenylalanine ammonia lyase is AtPAL2 from *Arabidopsis thaliana*, encoded by a nucleic acid sequence set forth in SEQ ID NO: 15 and wherein the phenylacrylic acid decarboxylase is AnPAD from *Aspergillus niger*, encoded by a nucleic acid sequence set forth in SEQ ID NO: 16.

It may be advantageous to provide the L-phenylalanine for production of styrene by catalysis of glucose in the same one-pot reaction system.

In some embodiments, the same genetically engineered cells or other genetically engineered cells produce L-phenylalanine from glucose by a reaction catalyzed by overexpression of at least one enzyme selected from a group comprising DAHP synthase (AroG), shikimate kinase (AroK), shikimate dehydrogenase (YdiB), chorismate mutase/prephenate dehydratase (PheA) and tyrosine aminotransferase (TyrB), or mutants thereof.

In some embodiments, AroG comprises an amino acid sequence set forth in SEQ ID NO: 17, variants, mutants, or fragments thereof; AroK comprises an amino acid sequence set forth in SEQ ID NO: 18, variants, mutants, or fragments thereof; YdiB comprises an amino acid sequence set forth in SEQ ID NO: 19, variants, mutants, or fragments thereof; PheA comprises an amino acid sequence set forth in SEQ ID NO: 20, variants, mutants, or fragments thereof and TyrB comprises an amino acid sequence set forth in SEQ ID NO: 21, variants, mutants, or fragments thereof.

In some embodiments, AroG is encoded by a nucleic acid comprising SEQ ID NO: 22; AroK is encoded by a nucleic acid comprising SEQ ID NO: 23; YdiB is encoded by a nucleic acid comprising SEQ ID NO: 24; PheA is encoded by a nucleic acid comprising SEQ ID NO: 25 and TyrB is encoded by a nucleic acid comprising SEQ ID NO: 26.

According to an embodiment of the invention, glucose can be catalyzed to 2-PE in the one-pot reaction system.

In some embodiments, the genetically engineered cells produce 2-PE from glucose by a reaction catalyzed by overexpression of DAHP synthase (AroG), shikimate kinase (AroK), shikimate dehydrogenase (YdiB), chorismate mutase/prephenate dehydratase (PheA) and tyrosine aminotransferase (TyrB), phenylalanine ammonia lyase (AtPAL2), phenylacrylic acid decarboxylase (AnPAD), styrene monooxygenase, styrene oxide isomerase, an aldehyde reductase and/or an alcohol dehydrogenase, variants, mutants, or fragments thereof.

In some embodiments, AroG is replaced by a feedback inhibition resistant mutant AroG* encoded by a nucleic acid comprising SEQ ID NO: 27 and/or PheA is replaced by a feedback inhibition resistant mutant PheA* encoded by a nucleic acid comprising SEQ ID NO: 28.

In some embodiments, the method according to any aspect of the invention further comprises deletion or inactivation of crr and/or prephenate dehydrogenase (tyrA) genes.

In some embodiments, the crr gene and/or tyrA gene are/is deleted and replaced with a short 10-20 bp length double stranded DNA, an example of which is shown in SEQ ID NO: 52 and SEQ ID NO: 53, respectively. In some embodiments, the at least one overexpressed enzyme is located on one or more plasmids. An example of suitable plasmids are T7 expression plasmids.

In some embodiments of the method of the invention, the one-pot reaction system comprises use of an aqueous medium.

It was found that 2-PE production above a certain concentration becomes toxic to the genetically engineered cells and sequestration and/or removal of 2-PE from the fermentation medium is desired. This may be effected by use of a bi-phasic medium.

In some embodiments, the one-pot reaction system comprises the use of a bi-phasic medium.

In some embodiments, the bi-phasic medium is an aqueous: solid resin medium.

In some embodiments, the bi-phasic medium is an aqueous: organic solvent medium.

In some embodiments, the one-pot reaction system comprises the use of a tri-phasic medium comprising an aqueous: organic solvent: solid resin medium.

In some embodiments, the one-pot reaction system comprises the use of a tri-phasic medium comprising an aqueous: organic solvent: functionalized nanoparticles medium.

In one aspect of the invention there is provided one or more genetically engineered/recombinant prokaryotic or eukaryotic cells selected from the group comprising bacterial cells, yeast cells, mammalian cells and insect cells, wherein said cells comprise at least one expression construct and/or heterologous nucleic acid molecule that encodes at least one catalytic enzyme required in the pathway from glucose to substituted or unsubstituted phenylacetaldehyde, 2-phenylethanol, phenylacetic acid or phenylethylamine.

According to a second aspect of the invention there is provided an isolated strain of genetically engineered cells capable of increased bioproduction of substituted or unsubstituted phenylacetaldehyde, 2-phenylethanol, phenylacetic acid or phenylethylamine in a one-pot reaction system compared to wild type cells, wherein the cells overexpress a combination of enzymes selected from groups (i)-(iv), which comprise:
(i) styrene monooxygenase and styrene oxide isomerase for generating substituted or unsubstituted phenylacetaldehyde from styrene or substituted styrene;
(ii) styrene monooxygenase, styrene oxide isomerase and an aldehyde dehydrogenase for generating substituted or unsubstituted phenylacetic acid from styrene or substituted styrene;
(iii) styrene monooxygenase, styrene oxide isomerase, an aldehyde reductase and/or an alcohol dehydrogenase for generating substituted or unsubstituted 2-phenylethanol from styrene or substituted styrene; and
(iv) styrene monooxygenase, styrene oxide isomerase and a transaminase for generating substituted or unsubstituted phenylethylamine from styrene or substituted styrene.

In some embodiments, the styrene monooxygenase is from *Pseudomonas* sp. VLB120 or its mutants, styrene oxide isomerase is from *Pseudomonas* sp. VLB120 or its mutants, the aldehyde dehydrogenase is from *Escherichia coli* or its mutants, the alcohol dehydrogenase is from *Saccharomyces cerevisiae* and the transaminase is ω-transaminase from *Chromobacterium violaceum* or its mutants.

In some embodiments, the styrene monooxygenase is encoded by a nucleic acid sequence set forth in SEQ ID NOs: 7 and 8; styrene oxide isomerase is encoded by a nucleic acid sequence set forth in SEQ ID NO: 9; the aldehyde dehydrogenase is encoded by a nucleic acid sequence set forth in SEQ ID NO: 10; the alcohol dehydrogenase is encoded by a nucleic acid sequence set forth in SEQ ID NO: 11 and the transaminase is ω-transaminase encoded by a nucleic acid sequence set forth in SEQ ID NO: 12.

It may be advantageous to provide the styrene or substituted styrene from conversion of L-phenylalanine or substituted L-phenylalanine in the same one-pot reaction system.

Accordingly, in some embodiments, the same or different genetically engineered cells produce styrene or substituted styrene from L-phenylalanine or substituted L-phenylalanine by a deamination reaction catalyzed by overexpression of an ammonia lyase and a decarboxylation reaction catalyzed by overexpression of a decarboxylase.

In preferred embodiments, the ammonia lyase is phenylalanine ammonia lyase and the decarboxylase is phenylacrylic acid decarboxylase.

In some embodiments, the phenylalanine ammonia lyase is AtPAL2 from *Arabidopsis thaliana*, encoded by a nucleic acid sequence set forth in SEQ ID NO: 15 and wherein the phenylacrylic acid decarboxylase is AnPAD from *Aspergillus niger*, encoded by a nucleic acid sequence set forth in SEQ ID NO: 16.

It may be advantageous to provide the L-phenylalanine for production of styrene by catalysis of glucose in the same one-pot reaction system.

In some embodiments, the same or different genetically engineered cells produce L-phenylalanine from glucose by a reaction catalyzed by overexpression of at least one enzyme selected from a group comprising DAHP synthase (AroG), shikimate kinase (AroK), shikimate dehydrogenase (YdiB), chorismate mutase/prephenate dehydratase (PheA) and tyrosine aminotransferase (TyrB), or mutants thereof.

In some embodiments, AroG is encoded by a nucleic acid comprising SEQ ID NO: 22; AroK is encoded by a nucleic acid comprising SEQ ID NO: 23; YdiB is encoded by a nucleic acid comprising SEQ ID NO: 24; PheA is encoded by a nucleic acid comprising SEQ ID NO: 25 and TyrB is encoded by a nucleic acid comprising SEQ ID NO: 26.

According to an embodiment of the invention, glucose can be catalyzed to 2-PE in the one-pot reaction system.

In some embodiments, the genetically engineered cells produce 2-PE from glucose by a reaction catalyzed by overexpression of DAHP synthase (AroG), shikimate kinase (AroK), shikimate dehydrogenase (YdiB), chorismate mutase/prephenate dehydratase (PheA) and tyrosine aminotransferase (TyrB), phenylalanine ammonia lyase (AtPAL2), phenylacrylic acid decarboxylase (AnPAD), styrene monooxygenase, styrene oxide isomerase, an aldehyde reductase and/or an alcohol dehydrogenase, variants, mutants, or fragments thereof.

In some embodiments, AroG is replaced by a feedback inhibition resistant mutant AroG* encoded by a nucleic acid comprising SEQ ID NO: 27 and/or PheA is replaced by a feedback inhibition resistant mutant PheA* encoded by a nucleic acid comprising SEQ ID NO: 28.

In further embodiments, the isolated strain according to any aspect of the invention further comprises a deletion or otherwise inactivation of crr and/or prephenate dehydrogenase (tyrA) genes. In some embodiments, the crr gene and/or tyrA gene are/is deleted and replaced with a short 10-20 bp length double stranded DNA, an example of which is shown in SEQ ID NO: 52 and SEQ ID NO: 53, respectively.

In some embodiments, the isolated strain of genetically engineered cells of the invention are wild type strains containing the necessary enzymes. Preferably said cells are genetically engineered bacterial cells. More preferably said cells are *Escherichia coli*.

In some embodiments, the isolated strain of genetically engineered cells are recombinant *E. coli* strains co-expressing multiple enzymes.

It will be appreciated that the method outlined above works by the combination of particular enzymes into a single reaction system.

According to an aspect of the present invention, there is provided an isolated nucleic acid molecule encoding at least one catalytic enzyme, according to any aspect of the present invention. More particularly, in some embodiments the present invention provides an isolated nucleic acid molecule encoding at least one heterologous catalytic enzyme selected from groups (i)-(iv), which comprise:
(i) a nucleic acid encoding styrene monooxygenase and styrene oxide isomerase for generating substituted or unsubstituted phenylacetaldehyde from styrene or substituted styrene;
(ii) a nucleic acid encoding styrene monooxygenase, styrene oxide isomerase and an aldehyde dehydrogenase for generating substituted or unsubstituted phenylacetic acid from styrene or substituted styrene;
(iii) a nucleic acid encoding styrene monooxygenase, styrene oxide isomerase, an aldehyde reductase and/or an alcohol dehydrogenase for generating substituted or unsubstituted 2-phenylethanol from styrene or substituted styrene; and (v) a nucleic acid encoding styrene monooxygenase, styrene oxide isomerase and a transaminase for generating substituted or unsubstituted phenylethylamine from styrene or substituted styrene.

In some embodiments the isolated nucleic acid molecule encodes at least one heterologous catalytic enzyme selected from phenylalanine ammonia lyase and phenylacrylic acid decarboxylase for generating styrene or substituted styrene from L-phenylalanine or substituted L-phenylalanine.

In some embodiments the isolated nucleic acid molecule encodes at least one heterologous catalytic enzyme selected from a group comprising DAHP synthase (AroG), shikimate kinase (AroK), shikimate dehydrogenase (YdiB), chorismate mutase/prephenate dehydratase (PheA) and tyrosine aminotransferase (TyrB), or mutants thereof for generating L-phenylalanine from glucose. In some embodiments AroG is replaced by a feedback inhibition resistant mutant AroG* encoded by a nucleic acid comprising SEQ ID NO: 27 and/or PheA is replaced by a feedback inhibition resistant mutant PheA* encoded by a nucleic acid comprising SEQ ID NO: 28.

It will be appreciated that the isolated nucleic acid of this aspect of the invention may encode a plurality of catalytic enzymes of which at least one is heterologous. For example, the plurality of catalytic enzymes is arranged as at least one module selected from the groups of modules (i)-(viii), which comprise:

i) a module comprising heterologous nucleic acid sequences that, when expressed, enzymatically transforms a styrene or substituted styrene to substituted or unsubstituted phenylacetaldehyde;

ii) a module comprising heterologous nucleic acid sequences that, when expressed, enzymatically transforms a styrene or substituted styrene to substituted or unsubstituted phenylacetic acid;

iii) a module comprising heterologous nucleic acid sequences that, when expressed, enzymatically transforms a styrene or substituted styrene to substituted or unsubstituted 2-phenylethanol;

iv) a module comprising heterologous nucleic acid sequences that, when expressed, enzymatically transforms a styrene or substituted styrene to substituted or unsubstituted phenylethylamine;

v) a module comprising heterologous nucleic acid sequences that, when expressed, enzymatically transforms a L-phenylalanine or substituted L-phenylalanine to a styrene or substituted styrene;

vi) a module comprising heterologous nucleic acid sequences that, when expressed, enzymatically transforms a L-phenylalanine or substituted L-phenylalanine to a substituted or unsubstituted 2-phenylethanol;

vii) a module comprising heterologous nucleic acid sequences that, when expressed, enzymatically transforms glucose to L-phenylalanine or substituted L-phenylalanine;

viii) a module comprising heterologous nucleic acid sequences that, when expressed, enzymatically transforms glucose to a substituted or unsubstituted 2-phenylethanol.

In particular, the isolated nucleic acid molecule may encode:

i) at least one of SEQ ID NOs: 1, 2, 3 and 4, variants, mutants, or fragments thereof to transform a to a styrene or substituted styrene to substituted or unsubstituted phenylacetic acid; and/or ii) at least one of SEQ ID NOs: 1, 2 and 3, variants, mutants, or fragments thereof to transform a styrene or substituted styrene to substituted or unsubstituted phenylacetaldehyde; and/or iii) at least one of SEQ ID NOs: 1, 2, 3 and 5, variants, mutants, or fragments thereof to transform a styrene or substituted styrene to substituted or unsubstituted 2-phenylethanol; and/or iv) at least one of SEQ ID NOs: 1, 2, 3 and 6, variants, mutants, or fragments thereof to transform a styrene or substituted styrene to substituted or unsubstituted phenylethylamine and/or v) at least one of SEQ ID NOs: 13 and 14, variants, mutants, or fragments thereof to transform a L-phenylalanine or substituted L-phenylalanine to a styrene or substituted styrene; and/or vi) at least one of SEQ ID NOs: 1, 2, 3, 5, 13 and 14, variants, mutants, or fragments thereof to transform a L-phenylalanine or substituted L-phenylalanine to a substituted or unsubstituted 2-phenylethanol; or vii) at least one of SEQ ID NOs: 17, 18, 19, 20, 21, 50 and 51, variants, mutants, or fragments thereof to transform glucose to L-phenylalanine; or viii) at least one of SEQ ID NOs: 1, 2, 3, 5, 13, 14, 17, 18, 19, 20, 21, 50 and 51, variants, mutants, or fragments thereof to transform glucose to a substituted or unsubstituted 2-phenylethanol.

According to another aspect of the invention there is provided a kit comprising at least one genetically engineered cell, expression construct or isolated nucleic acid according to any aspect of the invention.

BRIEF DESCRIPTION OF DRAWINGS

FIG. 6 shows a cascade transformation of styrene to 2-phenylethanol (2-PE) and genetic construction of downstream module 2-4 to co-express SMO, SOI, and ALDH.

FIGS. 7a and 7b show a SDS-PAGE analysis of whole-cell protein of (FIG. 7a) E. coli (StyABC-PAR) and (b) E. coli (StyABC-CvTA-AlaDH).

FIG. 8 shows a time course of biocatalytic hydration of 60 mM Sty to 2-PE with E. coli (StyABC-PAR) cells (10 g cdw $L^{-1}$) in KP buffer (200 mM, pH 8, 2% glucose) and n-hexadecane (1:1).

(FIG. 11a) biotransformation using different organic phase; (FIG. 11b) biotransformation using different aqueous buffer; (FIG. 11c) biotransformation using different glucose concentration; (FIG. 11d) biotransformation under different temperature; (FIG. 11e) biotransformation using different ratio of organic phase: aqueous buffer.

FIGS. 13a and 13b show the (FIG. 13a) Genetic construct of plasmid pRSF-StyABC-ADH9v1 and (FIG. 13b) SDS-PAGE analysis of cell protein of *E. coli* (StyABC-EcALDH) (lane 1) and *E. coli* (StyABC-ADH9v1) (lane 2).

FIG. 14 shows asymmetric cascade oxidation of α-methylstyrene (20 mM) to (S)-2-Phenylpropanoic acid using different amount of *E. coli* (StyABC-ADH9v1) resting cells in a two-liquid phase system of KP buffer (200 mM, pH 8.0) containing various amount of glucose and n-hexadecane (5:1) at 30° C.

(FIG. 21c) Repeated batch of 2-PE biotransformation from 100 mM L-phenylalanine with tri-phasic in-situ product removal via extraction and XAD4 resins adsorption in one pot. Cells (10 g/l) were resuspended in fresh buffer containing 0.5% glucose and 100 mM initial substrate concentration, then mixed with a new organic solvent and adsorbent to carry on the biotransformation.

(FIG. 25a) Cell growth profile with different ratio of M9 media and oleic acid in biphasic media and (FIG. 25b) the metabolites of the cultures at 24 h.

DESCRIPTION

Figure 1:
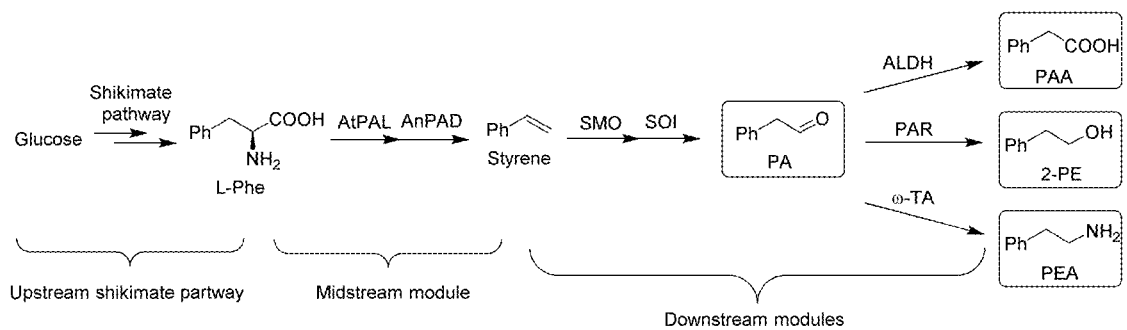
FIG. 1 shows an overall novel artificial pathway to produce 2-phenylethanol (2-PE), phenylacetaldehyde (PA), phenylacetic acid (PAA), and phenylethylamine (PEA) from glucose.

Bibliographic references mentioned in the present specification are for convenience listed in the form of a list of references and added at the end of the examples. The whole content of such bibliographic references is herein incorporated by reference.

Definitions

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extra-chromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In the context of the invention, "fragments" refers to those nucleic acid sequences which are greater than about 60 nucleotides in length, and most preferably are at least about 100 nucleotides, at least about 1000 nucleotides, or at least about 10,000 nucleotides in length which are not full-length native sequence but retain catalytic enzyme activity.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

The terms 'variant' and 'mutant' are used interchangeably herein. The at least one nucleic acids encoding at least one catalytic enzyme may encode a variant or mutant of the exemplified catalytic enzyme which retains activity. A "variant" of a catalytic enzyme, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing catalytic activity may be found using computer programs well known in the art, for example, DNASTAR software. In some embodiments, variant enzymes are at least 60%, 65%, 70%, 75%, 80%, 85%, 90%, 95%, 96%, 97%, 98%, 99%, or more, preferably at least 90%, homologous or identical at the amino acid level to an exemplary amino acid sequence described herein (e.g., alcohol dehydrogenase, ω-transaminase) or a functional fragment thereof—e.g., over a length of about: 50, 55, 60, 65, 70, 75, 80, 85, 90, 95, or 100%, preferably at least 90%, of the length of the mature reference sequence, yet retain catalytic activity. Preferably said variant enzymes have at least 90% identity at the amino acid level and retain catalytic activity. An exemplary alcohol dehydrogenase is represented by SEQ ID NO: 5, and an exemplary ω-transaminase is represented by SEQ ID NO: 6.

The terms 'phenylacetaldehyde reductase' (PAR) and 'alcohol dehydrogenase' (ADH), as referred to herein, are used interchangeably.

A vector can include one or more catalytic enzyme nucleic acid(s) in a form suitable for expression of the nucleic acid(s) in a host cell. Preferably the recombinant expression vector includes one or more regulatory sequences operatively linked to the nucleic acid sequence(s) to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences such as the T7 IPTG-inducible promoters disclosed in the Examples herein. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., catalytic enzyme proteins, fusion proteins, and the like).

The recombinant expression vectors of the invention can be designed for expression of catalytic enzyme proteins in prokaryotic or eukaryotic cells. For example, polypeptides of the invention can be expressed in bacteria (e.g., E. coli), insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector(s) can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein.

To maximize recombinant protein expression in E. coli is to express the protein in a host bacterium with an impaired capacity to proteolytically cleave the recombinant protein (Gottesman, S., (1990) Gene Expression Technology: Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by known DNA synthesis techniques and is described in the Examples.

The catalytic enzyme expression vector can be a yeast expression vector, a vector for expression in insect cells, e.g., a baculovirus expression vector, a vector for expression in bacterial cells, e.g. a plasmid vector, or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

The methods described hereinbefore make use of enzymes to catalyse a sequence of reactions. While these reactions may be performed individually or, more particularly, two or more of them in combination, it is particularly preferred that all of the reactions are combined into a cascade reaction sequence that provides the product from the initial starting material in one pot, thereby eliminating the need for isolation of the intermediates and, potentially, increasing the overall yield of the reaction sequence. These cascade reactions may involve the use of one or more reactive components selected from the group consisting of cells, immobilized cells, cell extracts, isolated enzymes and immobilized enzymes in said reaction vessel.

In this invention, we proposed a novel biocatalytic route (pathway) to produce "natural" 2-PE, PA, PAA, and PEA from the easy available biobased L-phenylalanine and glucose (FIG. 1). The route (pathway) is novel and clearly different from natural pathway. More importantly, the enzymes in the new pathway are known to be very efficient. For example, we had demonstrated the deamination-decarboxylation of L-phenylalanine by lyase and decarboxylase to produce styrene (the key intermediate) with up to 15 g/L. The further conversion of styrene into 2-PE, PA, PAA, and PEA are similar to natural styrene degradation pathway, which is known to be high efficiency. Recombinant *E. coli* strains were engineered to express the enzymes in high amount and optimal ratio, thus being efficient whole-cell catalysts for bioproduction of 2-PE, PA, PAA, and PEA. In addition, further process engineering will reduce the product toxicity and increase the final product concentration. In summary, our method will be a cost-effective way to produce valuable natural 2-PE, PA, PAA, and PEA from biobased resources.

Figure 2:
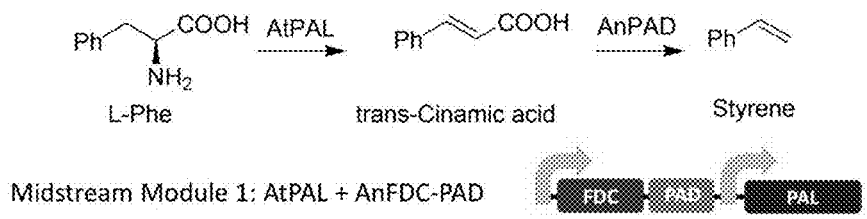
FIG. 2 shows a cascade transformation of L-Phe to styrene and genetic construction of midstream module 1 to co-express AtPAL and AnPAD.

The whole route was divided into three parts: 1) upstream shikimate pathway to produce L-Phe from glucose (FIG. 1); 2) midstream deamination-decarboxylation module to convert L-Phe to styrene (FIG. 2); 3) downstream modules to functionalize styrene to 2-PE, PA, PAA, and PEA, respectively (FIGS. 3-6). The upstream shikimate pathway to produce L-Phe is well-known and has been engineered to produce L-Phe in high concentration (>50 g/L). We recently demonstrated the midstream module of converting L-Phe to styrene (Sty) by co-expression of phenylalanine ammonia lyase (AtPAL2) from *Arabidopsis thaliana* and phenylacrylic acid decarboxylase (AnPAD) from *Aspergillus niger* [Zhou, Y., Wu, S., Li, Z. Angew. Chem. Int. Ed. 55: 11647-11650 (2016)]. In the downstream modules, Sty was converted to styrene oxide (SO) by styrene monooxygenase (SMO) with consumption of oxygen. Styrene oxide isomerase (SOI) was employed for conversion of SO to give aldehydes PA. In the last step, PA could be oxidized to PAA by an aldehyde dehydrogenase (ALDH), reduced to 2-PE by aldehyde reductase (e.g. PAR)/alcohol dehydrogenase (ADH), or aminated to PEA by ω-transaminase (ω-TA). Preferably, these multiple reactions are performed simultaneously or sequentially in one reaction vessel, allowing for green, efficient, and economical production of 2-PE, PA, PAA, and PEA, directly from biobased L-Phe or glucose. Thus one-pot cascade reactions could avoid the expensive and energy-consuming isolation and purification of intermediates, minimize wastes generation, and overcome the possible thermodynamic hurdles in traditional multi-step synthesis. Preferably, multiple enzymes are co-expressed inside one recombinant microbe strain, and the whole cells of the strain are directly applied as catalysts for directly fermentative production of 2-PE, PA, PAA, and PEA. Alternatively, these enzymes or modules could be separately expressed in several cells, purified individually, or immobilized and the biocatalyst (enzymes, cells, immobilized enzymes, and immobilized cells) can be mixed together in one pot to carry out the reaction. For example, a recombinant strain for fermentative production of L-Phe, and other strains for directly convert L-Phe to 2-PE, PA, PAA, and PEA respectively through the designed pathway (midstream and downstream modules).

In an embodiment of the invention, all the enzymes responsible for the reactions are co-expressed in one recombinant *E. coli* strain. In this case, all the chemical reactions are taken place inside a single cell. To construct the recombinant biocatalyst, the enzymes are cloned as several artificial operons or separately on one plasmid or several compatible plasmids. After transforming the plasmids into the *E. coli* strain, the multiple enzymes are co-expressed and the whole recombinant cells are served as a biocatalyst for the cascade reactions. The expression level of multiple enzymes could be adjusted and optimized for efficient cascade transformation without significant accumulation of intermediates. There are many methods to achieve tuning the expression level of multiple enzymes: using different plasmids, inducer, promoters or ribosome binding sites with different strength.

In a preferred embodiment, the cascade transformations are better performed in aqueous phase. For low concentration biotransformation, aqueous one phase system fulfills the requirement and can achieve the final product easily. However, the intermediate Sty and SO are generally hydrophobic (limited solubility in aqueous phase) and toxic for the cell and enzyme (may have substrate inhibition). Thus, an organic: aqueous two-phase reaction system is a better choice for high-concentration biotransformation. The Sty and SO are better soluble in organic phase, while the diols, amino alcohols, amino acids, cells, and enzymes are mostly in the aqueous phase. By applying the two-phase reaction system, the problems of low solubility and inhibition of Sty and SO are solved.

Other forms of biocatalyst could also be applied to synthesize 2-PE, PA, PAA, and PEA. They include isolated enzyme, enzymes immobilized on nano or micro size support (such as magnetic nano particles) to increase their stability and re-usability, wild type microbial cells, and recombinant cells immobilized on some carriers. By utilizing isolated enzymes, immobilized enzymes or immobilized cells, the cascade biocatalysis can be performed to produce 2-PE, PA, PAA, and PEA from biobased L-Phe or glucose. A mixture of different forms of biocatalyst is also a suitable system to carry out the cascade biocatalysis.

EXAMPLES

Standard molecular biology techniques known in the art and not specifically described were generally followed as described in Green and Sambrook, *Molecular Cloning: A Laboratory Manual*, Cold Springs Harbor Laboratory, New York (2012).

Strain, Biochemicals, and Culture Medium

*Escherichia coli* T7 expression cells were purchased from New England Biolabs. Primers (DNA oligos) were synthesized from IDT. Phusion DNA polymerase, fast digest restriction enzymes, and T4 DNA ligase were bought from Thermo Scientific. LB medium, tryptone, yeast extract, and agar were obtained from Biomed Diagnostics. Chloramphenicol, streptomycin, ampicillin, kanamycin, and glucose were purchased from Sigma-Aldrich. IPTG (Isopropyl β-D-1-thiogalactopyranoside) was obtained from Gold Biotechnology.

The culture medium used in this study is standard M9 medium supplemented with glucose (20 g/L), yeast extract (6 g/L). The M9 medium contains 6 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$, and 1 mL/L $l^{-1}$ trace metal solution. The trace metal solution contains 8.3 g/L $FeCl_3.6H_2O$, 0.84 g/L $ZnCl_2$, 0.13 g/L $CuCl_2.2H_2O$, 0.1 g/L $CoCl_2.2H_2O$, 0.1 g/L $H_3BO_3$, 0.016 g/L $MnCl_2.4H_2O$, and 0.1 g/L $Na_2MoO_4.2H_2O$ in 1 M HCl.

SDS-PAGE Analysis and Quantification

Freshly prepared *E. coli* whole cells were centrifuged and resuspended in DI water to a density of 8 g cdw/L ($OD_{600}$=20). The cell suspension (60 μL) was mixed with 20 μl of SDS sample buffer (4× Laemmli Sample Buffer with DTT, Bio-Rad) and heated to 98° C. for 15 min. 60 μl of 0.2 g/L, 0.1 g/L, and 0.05 g/L of BSA standards were also mixed with 20 μL of SDS sample buffer and heated to 98° C. for 15 min. Then the mixture was centrifuged (13000 g) for 10 min. 10 μL of the supernatant was used to load into the sample well of 12% SDS-PAGE gel (hand cast). The electrophoresis was run in a setup of Mini-Protean tetra cell at 100 V for 15 min and 150 V for 75 min. After running, the PAGE gel was washed with water and then stained with Bio-Safe Coomassie Stain (Bio-Rad) according to the instruction. The figure was obtained with GS-900 calibrated densitometer (Bio-Rad), and quantification analysis was done with the volume tools in the Image Lab software (Bio-Rad).

General Procedures for Culturing *E. coli* Cells for Biotransformation

*E. coli* strain was initially inoculated in LB medium (1 mL) containing appropriate antibiotics (50 mg/L kanamycin, 50 mg/L chloramphenicol, 50 mg/L streptomycin, 50 mg/L ampicillin) for 8-10 h (280 rpm) at 37° C. and then were transferred to a 250 mL tribaffled flask with 50 mL of M9 medium supplemented with glucose (20 g $L^{-1}$), yeast extract (6 g $L^{-1}$), and appropriate antibiotics. The cells continued to grow at 37° C. and 250 rpm for about 2 h to reach an $OD_{600}$ of 0.6, and then IPTG (0.5 mM final concentration) was added to induce the enzyme expression. The cells were further grown at 22° C. overnight (12-13 h), and harvested by centrifugation (4000 g, 10 min).

Chemical and Materials

The following chemicals were purchased from Sigma-Aldrich: Sty-m-OMe-Sty, α-Me-Sty, p-Me-α-Me-Sty, Sty oxide, PA, PAA-p-OMe-PAA, rac-2-Phenylpropanoic acid-α, 4-Dimethylphenylacetic acid, (S)-2-Phenylpropanoic acid, acetic acid, ethyl oleate, n-hexadecane, kanamycin, glucose, NaCl, $Na_2SO_4$, $Na_2HPO_4$, $NH_4Cl$, $KH_2PO_4$, $K_2HPO_4$, TFA, phenethylamine, and benzyl alcohol. p-OMe-Sty was from Alfa Asear. Oleic acid, p-F-α-Me-Sty and p-Cl-α-Me-Sty were from TCI chemical. Acetonitrile, ethyl acetate, 2-propanol and n-hexane were purchased from Tedia. n-Heptane, silica gel 60 and TLC plates were purchased from Merck. LB medium, yeast extract, and agar were purchased from Biomed Diagnostics. DNA polymerase, ligase, and restriction enzymes were purchased from Thermo Fisher.

Analytical Methods

Cell growth was monitored by spectrophotometry (Nano-Drop™, Thermo Fisher Scientific Inc., Massachusetts, USA) measurement of the optical density ($OD_{600}$) at 600 nm. Metabolites such as L-Phe and 2-PE were measured by high-performance liquid chromatography (Prominence, Shimadzu Corporation) equipped with photodiode array (DAD) detectors. The media samples were centrifuged and filtered, and eluted through Agilent Poroshell 120 SB-C18 column (150×4.6 mm, 2.7 μm) under reversed phase condition with 30% acetonitrile and 70% ultrapure water containing 0.1% TFA. Flowrate: 0.4 ml/min, temperature: 25° C. Detector: photodiode array detector. Wavelength: 210 nm. 2-PE extracted in the oleic acid was eluted through Agilent ZORBAX RX-SIL column (150×4.6 mm, 5 μm) with 2% acetonitrile and hexane. Glucose levels during fed-batch fermentation was monitored by HPLC equipped with refractive index detector. The samples were eluted using Aminex-HPX87P column (Biorad, USA) with ultrapure water as mobile phase.

2-PE (organic phase) and styrene were analyzed using Agilent 7890A Gas Chromatography (GC). Column: Agilent HP-5 (30 m×0.32 mm×0.25 mm). Temperature programme: initial temperature at 70° C., increase 25° C./min until it reached 200° C.; subsequently increase to 250° C. at 50° C./min, then hold for 1 minute; Lastly, increase to 270° C. at 20° C./min.

Size and morphology of synthesized-MNPs were determined using JEOL JEM 2010 Transmission Electron Microscope (TEM-JEOL, USA). Hydrodynamic diameter and size distribution were characterized using zetasizer (Molvern).

HPLC analysis of Sty-p-OMe-Sty was performed on a Shimadzu prominence HPLC system with a photodiode array detector and a reverse-phase Agilent Poroshell 120 SB-C18 column (150×4.6 mm, 2.7 mm) at 25° C. Mobile phase: 50% water with 0.1% TFA: 50% acetonitrile. Flow rate: 0.5 $mLmin^{-1}$. The concentration was determined by comparison of peak areas at 210 nm to those on the calibration curve of the authentic compound. Retention times: phenethylamine (internal standard) 3.2 min, PAA 4.8 min, o-F-PAA 5.0 min, m-F-PAA 5.1 min, p-F-PAA 5.0 min, m-CI-PAA 6.0 min, p-CI-PAA 6.1 min, m-Br-PAA 6.4 min, p-Br-PAA 6.5 min, m-Me-PAA 5.7 min, p-Me-PAA 5.7 min, m-OMe-PAA 4.8 min, p-OMe-PAA 4.7 min.

GC-FID analysis of Sty-p-OMe-Sty, Sty oxide and PA was performed on an Agilent 7890A gas chromatograph system with an FID detector. Column: Agilent HP-5 (30 m×0.32 mm×0.25 mm). Temperature program: start at 70° C., increase to 200° C. at 25° C. $min^{-1}$, increase to 250° C. at 50° C. $min^{-1}$, hold for 1 min, and then increase to 270° C. at 20° C. $min^{-1}$. The concentration was determined by comparison of peak areas to those on the calibration curve of the authentic compound. Retention times: benzyl alcohol (internal standard) 2.8 min, Sty 2.2 min, o-F-Sty 2.2 min, m-F-Sty 2.2 min, p-F-Sty 2.2 min, m-CI-Sty 3.1 min, p-Cl-Sty 3.1 min, m-Br-Sty 3.5 min, p-Br-Sty 3.5 min, m-Me-Sty 2.6 min, p-Me-Sty 2.6 min, m-OMe-Sty 3.4 min, p-OMe-Sty 3.4 min.

Chiral HPLC analysis of α-Me-Sty-p-Me-α-Me-Sty (concentration) was performed on the same HPLC system with a reverse-phase Daicel Chiralpak AD-3R column (150×4.6 mm, 3 mm) at 15° C. The concentration was determined by comparison of peak areas at 210 nm to those on the calibration curve of authentic compound.

Method A: mobile phase consisting of 80% water with 0.1% TFA: 20% acetonitrile was delivered at 1.0 mLmin$^{-1}$. Retention times: benzyl alcohol (internal standard) 5.8 min, (R)-2-Phenylpropanoic acid 13.9 min, (S)-2-Phenylpropanoic acid 14.6 min, (R)-p-F-α-Me-PAA 19.2 min, (S)-p-F-α-Me-PAA 19.9 min, (R)-p-Me-α-Me-PAA 32.3 min, (S)-p-Me-α-Me-PAA 33.4 min.

Method B: mobile phase consisting of 70% water with 0.1% TFA: 30% acetonitrile was delivered at 1.0 mLmin$^{-1}$. Retention times: benzyl alcohol (internal standard) 3.8 min, (R)-p-Me-α-Me-PAA 12.2 min, (S)-p-Me-α-Me-PAA 13.0 min.

The ee values of (S)-2-Phenylpropanoic acid-(S)-p-Me-α-Me-PAA were measured with another chiral HPLC analysis method using a Daicel Chiralpak ADH column (250×4.6 mm, 5 mm) at 25° C. Mobile phase consisting of 90% n-hexane with 0.1% TFA: 10% 2-propanol was delivered at 1.0 mLmin$^{-1}$. Retention times: (R)-2-Phenylpropanoic acid 5.7 min, (S)-2-Phenylpropanoic acid 6.3 min, (R)-p-F-α-Me-PAA 5.7 min, (S)-p-F-α-Me-PAA 6.3 min, (R)-p-CI-α-Me-PAA 6.0 min, (S)-p-CI-α-Me-PAA 6.6 min, (R)-p-Me-α-Me-PAA 5.7 min, (S)-p-Me-α-Me-PAA 6.4 min.

Conversion of Styrene and Substituted Styrene to 2-Phenylethanols (2-PEs), Phenylacetaldehydes (PAs), Phenylacetic Acids (PAAs), and Phenylethylamines (PEAs)

Figure 3:
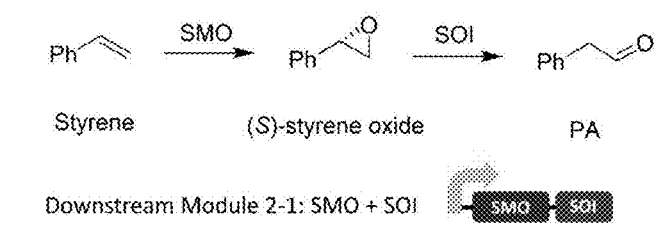
FIG. 3 shows a cascade transformation of styrene to phenylacetaldehyde (PA) and genetic construction of downstream module 2-1 to co-express SMO and SOI.
Figure 4:
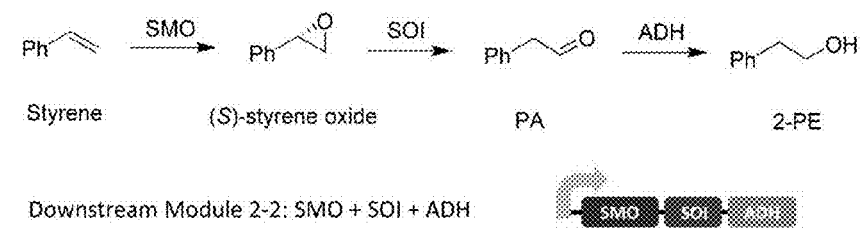
FIG. 4 shows a cascade transformation of styrene to 2-phenylethanol (2-PE) and genetic construction of downstream module 2-2 to co-express SMO, SOI, and ADH.
Figure 5:
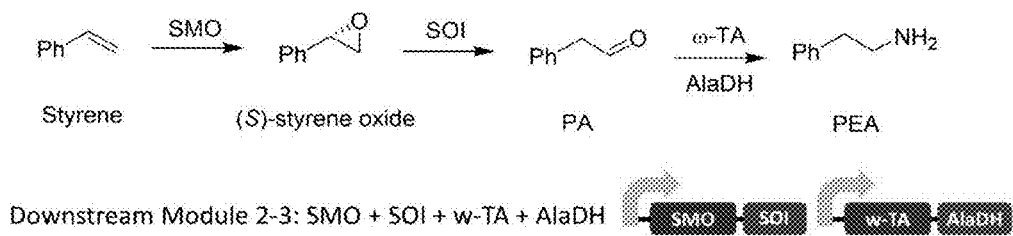
FIG. 5 shows a cascade transformation of styrene to phenylethylamine (PEA) and genetic construction of downstream module 2-3 to co-express SMO, SOI, ω-TA, and AlaDH.

A representative example was demonstration of converting (substituted) styrene to (substituted) 2-PE. Previously, we had engineered *E. coli* co-expressing SMO from styrene degradation *Pseudomonas* sp. VLB120 [Wu, S., Chen, Y., et al., *ACS Catal.* 4: 409-420 (2014)]. The gene of SOI was amplified and constructed together with SMO to give an artificial operon as module 2-1 on plasmid pRSFduet-1 (FIG. 3). In addition, the gene of phenylacetaldehyde reductase (PAR) from tomato [Tieman, D. M., Loucas, H. M., et al., *Phytochemistry* 68: 2660 (2007)] was engineered together with SMO-SOI to give an artificial operon as module 2-2 in this project (FIG. 4). The plasmid containing module 2-2 was transformed to give *E. coli* (StyABC-PAR) strain, which was used as the whole-cell biocatalyst for converting Sty to 2-PE. The expression of the enzymes was examined by a SDS-PAGE analysis, and all the enzymes were clearly visible (FIG. 7a). By using 10 g cdw/L of resting cells of *E. coli* (StyABC-PAR), 60 mM of Sty was quickly converted to 2-PE in the initial 3 h, and only a very small amount of SO (0.3%) and PA (3%) were accumulated at initial 1 h (FIG. 8). At end of reaction (8 h), the desired 2-PE was formed in 93% analytical yield with little Sty (2%) was remained. Importantly, another isomer of 2-PE, 1-phenyethanol, was not produced in the biotransformation. The *E. coli* (StyABC-PAR) was employed for converting substituted Sty to substituted 2-PE (Table 1). Many substituted 2-PEs were produced in very high conversion (≥90%): fluoro substituted 2-PEs (entries 2-4), methyl substituted 2-PEs (entries 9, 10), and methoxy substituted 2-PEs (entries 11, 12). 2-PEs with a chloro (entries 5, 6) or bromo (entries 7, 8) substituent were formed in good conversion of 89-62%. Importantly, 1-phenyethanols were not produced in the biotransformation. This demonstrated the efficient conversion of Sty to 2-PE via the novel pathway.

Figure 9:
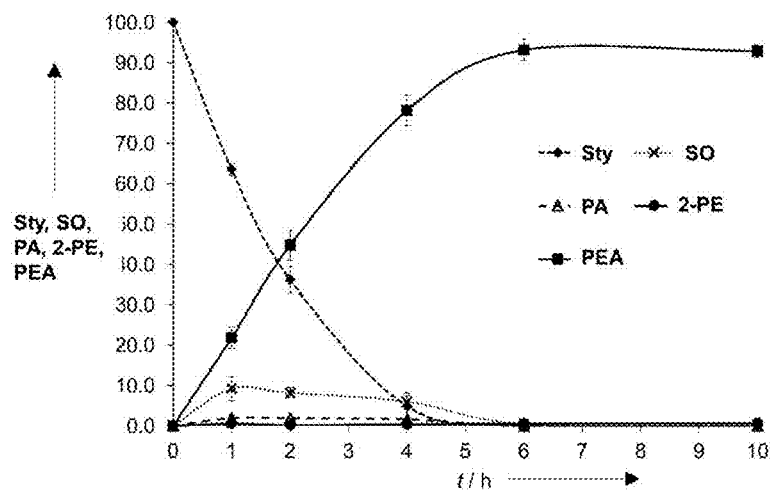
FIG. 9 shows a time course of biocatalytic hydroamination of 80 mM Sty to PEA with E. coli (StyABC-CvTA-AlaDH) cells (10 g cdw/L) in NaP buffer (200 mM, pH 8, 2% glucose, 200 mM $NH_3/NH_4Cl$) and n-hexadecane (1:1).

To achieve conversion of (substituted) Sty to (substituted) PEA (FIG. 5), an artificial operon containing ω-TA and AlaDH was constructed. The genes of CvTA from *Chromobacterium violaceum* [Kaulmann, U., Smithies, K., et al., *Enzyme Microb. Technol.* 41: 628-637 (2007)] and AlaDH from *Bacillus subtilis* were combined to give CvTA-AlaDH on plasmid pCDFduet-1. The SMO-SOI on plasmid pACYCduet-1 was co-transformed with the above plasmid into *E. coli* (RARE) strain [11] to give the recombiant strain *E. coli* (StyABC-CvTA-AlaDH) co-expressing the four enzymes, SMO, SOI, CvTA, and AlaDH as module 2-3. Transformation of Sty at various concentration was performed with resting cells of *E. coli* (StyABC-CvTA-AlaDH), and high conversion to PEA was achieved for 75 mM Sty. 80 mM Sty was quickly converted to PEA in the first 4 h, and some SO (up to 9%) and PA (up to 2%) was accumulated and converted (FIG. 9). At end of reaction (10 h), the amine PEA was produced in 93% conversion. Notably, alcohol byproduct 2-PE was detected in trivial amount (0.6%), indicating a very high chemo selectivity. In addition, another isomer of PEA, 1-phenyethylamine, was not observed, demonstrating an excellent regioselectivity. The *E. coli* (StyABC-CvTA-AlaDH) was employed for converting substituted Sty to substituted PEA (Table 2). Fluoro-substituted PEAs (entries 2-4), methyl-substituted PEAs (entries 9, 10) and methoxy-substituted PEAs (entries 11, 12) were produced in very high conversion of 94-99%. Chloro-substituted PEAs (entries 5, 6) and bromo-substituted PEAs (entries 7, 8) were formed in good to moderate conversion of 86-45%. The chemo-selectivity of amine over alcohol was also very high (all >20:1), and the regioselectivity was excellent. The current system could be improved by further optimization of reaction conditions or using more efficient enzymes.

Figure 10A:
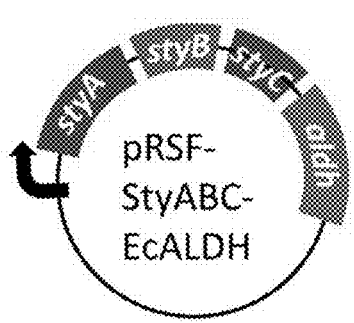
FIGS. 10a and 10b show (FIG. 10a) Genetic construct of plasmid pRSF-StyABC-EcALDH and (FIG. 10b) SDS-PAGE analysis of whole-cell protein of E. coli (StyABC-EcALDH) co-expressing SMO (StyA & StyB), SOI (StyC), and EcALDH.
Figure 10B:
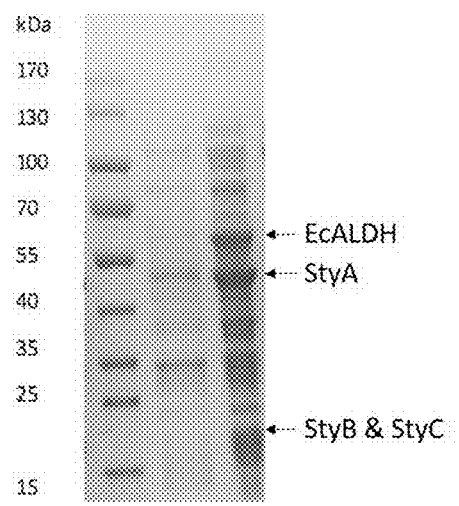
Figure 11A:
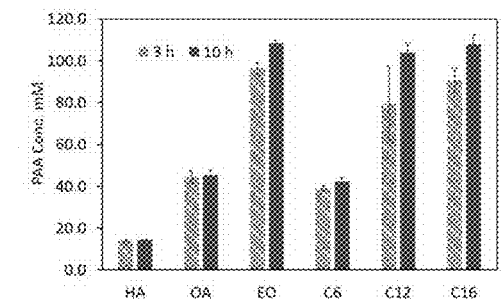
FIGS. 11a to 11e show optimization of reaction conditions for biotransformation of Sty to PAA with *E. coli* (StyABC-EcALDH) cells (10 g cdw/L).
Figure 11B:
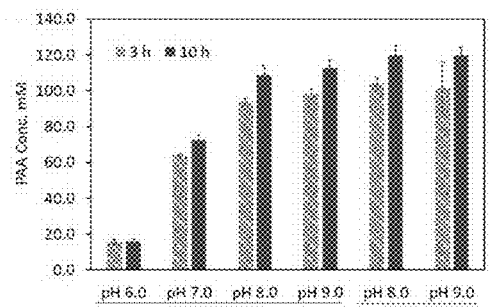
Figure 11C:
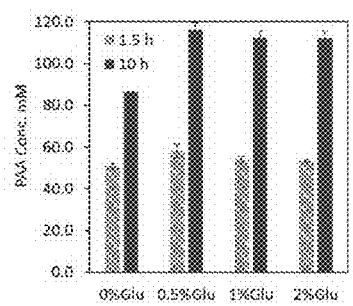
Figure 11D:
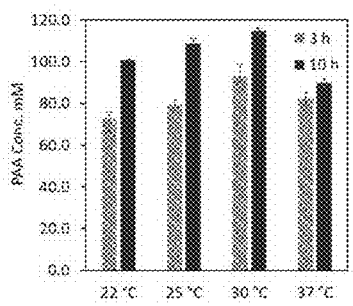
Figure 11E:
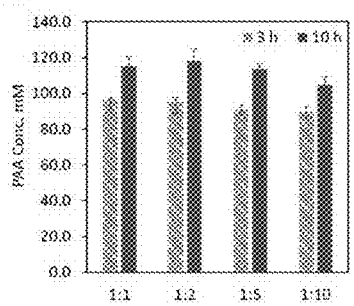
Figure 12:
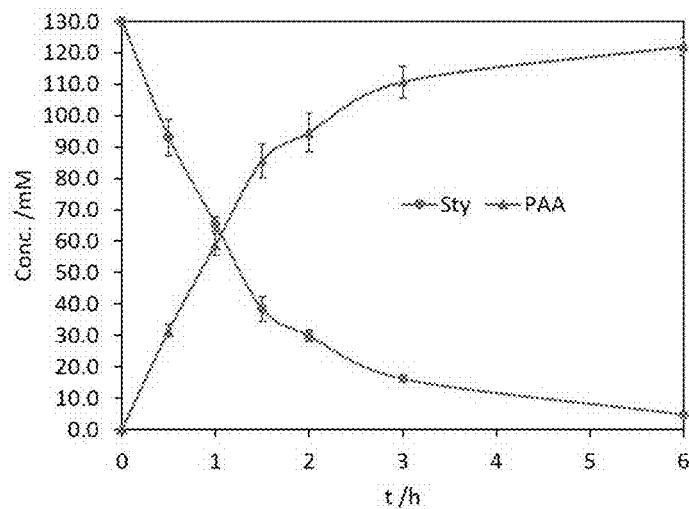
FIG. 12 shows a time course of biocatalytic hydroamination of 1300 mM Sty to PAA with *E. coli* (StyABC-EcALDH) cells (15 g cdw/L) in KP buffer (400 mM, pH 8, 0.5% glucose) and ethyl oleate (1:1).

Another representative example was demonstration of converting (substituted) styrene to (substituted) PAA. The gene of phenylacetaldehyde dehydrogenase (EcALDH) from *E. coli* [Ferrandez, A., Prieto, M. A., et al., *FEBS Lett.* 406: 23 (1997)] was engineered together with SMO-SOI to give an artificial operon as module 2-4 (FIG. 6). The plasmid containing module 2-4 was transformed to give *E. coli* (StyABC-EcALDH) strain, which was used as the whole-cell biocatalyst for converting Sty to PAA. The expression of the enzymes was examined by a SDS-PAGE analysis, and all the enzymes were clearly visible (FIG. 10 (*b*) and FIG. 13 (*b*)). The best biotransformation condition was found by exploring different organic phase, buffer, glucose concentration, temperature, and ratio of the two phases (FIG. 11). Under the optimal condition, 15 g cdw/L of resting cells of *E. coli* (StyABC-EcALDH) successfully converted 130 mM of Sty to 122 mM of PAA (94% overall yield) in 6 h, and no intermediate was accumulated during the reaction (FIG. 12). The *E. coli* (StyABC-EcALDH) was employed for converting substituted Sty to substituted 2-PE (Table 3). Many substituted PAAs were produced in very high conversion (≥90%): fluoro-substituted PAAs (entries 2-4), methyl-substituted PAAs (entries 9, 10), and methoxy-substituted PAAs (entries 11, 12). PAAs with a chloro (entries 5, 6) or bromo (entries 7, 8) substituent were formed in good conversion of 87-78%. This demonstrated the efficient conversion of Sty to PAA by the recombinant *E. coli*.

To produce (S)-PAA in very high ee, alcohol dehydrogenase ADH9v1, as reported in [P. Könst, H. Merkens, et al., *Angew. Chem. Int. Ed.* 51: 9914-9917 (2012)] with S-selectivity for the enantioselective oxidation of racemic PA was cloned. The gene of ADH9v1 was synthesized and constructed together with styC and pRSF-StyAB to form a recombinant plasmid pRSF-StyABC-ADH9v1 (FIG. 13 (*a*)). This plasmid was transformed into *E. coli* T7 express strain to give *E. coli* (StyABC-ADH9v1). The strain was grown and induced under the same cultivation procedure for *E. coli* (StyABC-EcALDH). SDS-PAGE analysis of the cell protein confirmed the expression of StyA, StyB, StyC, and ADH9v1 (lane 2 in FIG. 13 (*b*)).

Further description of exemplary embodiments are provided below.

Example 1. Genetic Engineering of E. coli Containing Module 2-1 and Expressing SMO and SOI The styC gene coding SOI (SEQ ID NO: 9) from Pseudomonas sp. VLB120 was first synthesized and codon optimized for E. coli according the published sequence. Then it was amplified using primers StyC-Kpnl-RBS-F (CGGGTACCTAAGGAGATATATAATGTTACACGCGT-TTGAACGTA AAATG; SEQ ID NO: 29) and StyC-HindIII-Xhol-R (ACTGCTCGAGAAGCTTACTCGGCT-GCCGCG TGTGGAACGGCTTTACG; SEQ ID NO: 30) and Phusion DNA polymerase (available from Thermo). The PCR products were double-digested with Kpnl and Xhol, and then ligated to same digested pRSF-SMO plasmid [Wu, S., Chen, Y., et al., ACS Catal. 4: 409-420 (2014)] with T4 DNA ligase. The ligation product was transformed (heat shock) into E. coli T7 Expression competent cells (available from New England Biolabs) to give pRSF-SMO-SOI. This module 2-1 was sub-cloned to other three vectors by the following procedures. Module 2-1 operon was amplified with primers StyA-BspHI-F (ACTGTC ATGAAAAAG-CGTATCGGTATTGTTGG; SEQ ID NO: 31) and StyC-HindIII-Xhol-R (ACTGCTCGAG AAGCTTACTCG-GCTGCCGCGTGTGGAACGGCTTTACG; SEQ ID NO: 30), digested with BspHI and Xhol, and then ligated to double digested pACYCduet, pCDFduet, and pETduet (available from Novagen). The transformation of these products gave pACYC-SMO-SOI, pCDF-SMO-SOI, and pET-SMO-SOI respectively.

Example 2. Genetic Engineering of E. coli Containing Module 2-2 and Expressing SMO, SOI, and PAR The pad gene coding ADH (alcohol dehydrogenase; SEQ ID NO: 11) from tomato Saccharomyces cerevisiae was first synthesized and codon optimized for E. coli according the published sequence. Then it was amplified using primers PAR-HindIII-RBS-F (ACTGAAGCTTTAAGGAGA-TATATAATGAGCGTGAC CGCGAAAACCGTG; SEQ ID NO: 32) and PAR-Xhol-R (ACTGCTCGAGTCA-CATGCTTGAACTCCCG CCGAAA; SEQ ID NO: 33) and Phusion DNA polymerase (available from Thermo). The PCR products were double digested with HindIII and Xhol, and then ligated to same digested pRSF-SMO-SOI plasmid (see example 1) with T4 DNA ligase. The ligation product was transformed (heat shock) into E. coli T7 Expression competent cells (available from New England Biolabs) to give pRSF-SMO-SOI-PAR. This module 2-2 was sub-cloned to other three vectors by the following procedures. Module 2-2 operon was amplified with primers StyA-BspHI-F (ACTGTC ATGAAAAAGCGTATCGGTAT-TGTTGG; SEQ ID NO: 31) and PAR-Xhol-R (ACTGCTCGAGTCACAT GCTTGAACTCCCG CCGAAA; SEQ ID NO: 33), digested with BspHI and Xhol, and then ligated to double digested pACYCduet, pCDFduet, and pETduet (available from Novagen). The transformation of these products gave pACYC-SMO-SOI-PAR, pCDF-SMO-SOI-PAR, and pET-SMO-SOI-PAR respectively.

Example 3. Production of 2-PE From Sty via Cascade Biocatalysis by Using E. coli Containing Module 2-2 and Expressing SMO, SOI, and PAR The recombinant E. coli (StyABC-PAR) containing the plasmid pRSF-SMO-SOI-PAR was grown in 1 mL LB medium containing 50 mg/L kanamycin at 37° C. and then inoculated into 50 mL M9 medium containing glucose (20 g/L), yeast extract (6 g/L), and 50 mg/L kanamycin. When $OD_{600}$ reached 0.6, 0.5 mM IPTG was added to induce the expressing of enzymes. The cells continued to grow and expressed protein for 12 hours at 22° C. before they were harvested by centrifuge (4000 g, 10 mins). The cells were resuspended in 200 mM KPB buffer (pH=8.0) to 10 g cdw/L with 2% glucose (for cofactor regeneration). To a 2 mL of aqueous system, a 2 mL n-hexadecane containing 60 mM Sty was added to the reaction system to form a second phase. The reaction was conducted at 30° C. and 300 rpm in a 100-mL flask for 8 hours. 100 μL of aqueous phase samples were taken during the reaction and analyzed by reverse phase HPLC (Agilent poroshell 120 EC-C18 column, acetonitrile:water=50:50, and flow rate 0.5 mL/min) to quantify the production of 2-PE in aqueous phase. 100 μL of organic phase samples were taken during the reaction and analyzed by GC-FID (Agilent HP-5 column, 70° C. increase to 200° C. at 25° C./min, increase to 250° C. at 50° C./min, hold for 1 min, and then increase to 270° C. at 20° C./min) to quantify Sty, SO, PA, 2-PE in the organic phase. 2-PE was produced from Sty, with a best result of about 56 mM (93% yield) obtained in 8 h (FIG. 8). This result showed that the constructed recombinant strain is a powerful catalyst for the cascade biotransformation of Sty to 2-PE.

Example 4. Efficient Production of Substituted 2-PE From Substituted Sty via Cascade Biocatalysis by Using E. coli (StyABC-PAR)

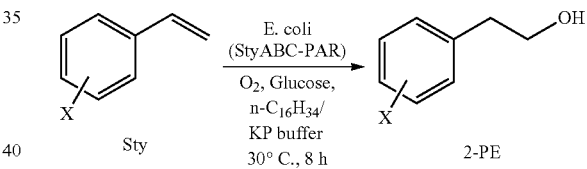

E. coli (StyABC-PAR) was grown in 1 mL LB medium containing 50 mg/L kanamycin at 37° C. and then inoculated into 50 mL M9 medium containing glucose (20 g/L), yeast extract (6 g/L), and 50 mg/L kanamycin. When $OD_{600}$ reached 0.6, 0.5 mM IPTG was added to induce the expressing of enzymes. The cells continued to grow and expressed protein for 12 h at 22° C. before they were harvested by centrifuge (4000 g, 10 mins). The cells were resuspended in 200 mM KPB buffer (pH=8.0) to 10 g cdw/L with 2% glucose (for cofactor regeneration). To a 2 mL of aqueous system, a 2-mL n-hexadecane containing 20 mM of substituted Sty was added to the reaction system to form a second phase. The reaction was conducted at 30° C. and 300 rpm in a 100-mL flask for 8 hours. 100 μL of aqueous phase samples were taken during the reaction and analyzed by reverse phase HPLC (Agilent poroshell 120 EC-C18 column, acetonitrile:water=50:50, and flow rate 0.5 mL/min) to quantify the production of substituted 2-PE in aqueous phase. 100 μL of organic phase samples were taken during the reaction and analyzed by GC-FID (Agilent HP-5 column, 70° C. increase to 200° C. at 25° C./min, increase to 250° C. at 50° C./min, hold for 1 min, and then increase to 270° C. at 20° C./min) to quantify substituted Sty, SO, PA, 2-PE in organic phase. As shown in Table 1, all the 12 substituted 2-PEs were produced in good to excellent yield 62-99% in 8 h. This prove the relative broad scope of the cascade biotransformation system.

TABLE 1

Conversion of substituted styrene to substituted 2-PEs with *E. coli* (StyABC-PAR).

| Entry | Substrate | Product | Conv. to 2-PE [%][b] | Regioselectivity 2-OH:1-OH [c] |
|---|---|---|---|---|
| 1 | Sty | H | >99 | >99:1 |
| 2 | o-F-Sty | o-F-2-PE | 90 | >99:1 |
| 3 | m-F-Sty | m-F-2-PE | 94 | >99:1 |
| 4 | p-F-Sty | p-F-2-PE | 98 | >99:1 |
| 5 | m-Cl-Sty | m-Cl-2-PE | 89 | >99:1 |
| 6 | p-Cl-Sty | p-Cl-2-PE | 80 | 98:2 |
| 7 | m-Br-Sty | m-Br-2-PE | 83 | 99:1 |
| 8 | p-Br-Sty | p-Br-2-PE | 62 | 98:2 |
| 9 | m-Me-Sty | m-Me-2-PE | 99 | >99:1 |
| 10 | p-Me-Sty | p-Me-2-PE | 96 | >99:1 |
| 11 | m-OMe-Sty | m-OMe-2-PE | >99 | >99:1 |
| 12 | p-OMe-Sty | p-OMe-2-PE | 96 | 98:2 |

[a] Sty (20 mM in organic phase) was transformed with resting cells (10 g cdw L$^{-1}$) in KP buffer (200 mM, pH 8, 2% glucose) and n-hexadecane (1:1) at 30° C. and 250 rpm for 8 h.
[b] Determined by HPLC analysis of aqueous phase and GC-FID analysis of organic phase.
[c] Measured by GC-FID analysis.

Example 5. Preparation of (Substituted) 2-PE From (Substituted) Sty by Using *E. coli* (StyABC-PAR) in a 100 mL System

*E. coli* (StyABC-PAR) was grown in 1 mL LB medium containing 50 mg/L kanamycin at 37° C. and then inoculated into 50 mL M9 medium containing glucose (20 g/L), yeast extract (6 g/L), and 50 mg/L kanamycin. After 5 h growth at 37° C., the 50 mL culture was expanded into 2 L M9 medium containing glucose (20 g/L), yeast extract (6 g/L), and 50 mg/L kanamycin and continue culture at 37° C. When OD$_{600}$ reached 0.6, 0.5 mM IPTG was added to induce the expressing of enzymes. The cells continued to grow and expressed protein for 12 hours at 22° C. before they were harvested by centrifuge (4000 g, 10 mins). The cells were resuspended in 200 mM KPB buffer (pH=8.0) containing 2% glucose to 10 g cdw/L. To a 50 mL of aqueous system, a 50-mL n-hexadecane containing 50 mM of Sty was added to the reaction system to form a second phase. The reaction was conducted at 30° C. and 300 rpm in a 1-L flask for 24 hours. After reaction, the two phase was separated by centrifugation (4000 g, 15 mins). The aqueous phase was extracted with 50 mL ethyl acetate for three times, and the hexadecane phase was wash with 50 mL water for three times. The wash water was combined and extracted with 100 mL ethyl acetate for two times. All the ethyl acetate was combined, dried over Na$_2$SO$_4$ and evaporated. The residue was further purified by flash chromatography with n-hexane: ethyl acetate=5:1. The fractions were combined and evaporated to get 253 mg of pure 2-PE with 83% isolated yield. Using the similar process, p-fluoro-2-PE, p-methyl-2-PE, and m-methyoxyl-2-PE were also isolated in 74%, 66%, and 78% yield, respectively.

Example 6. Genetic Engineering of *E. coli* Containing Module 2-3 and Expressing SMO, SOI, CvTA, and AlaDH The cvTA gene (coding CvTA; SEQ ID NO: 12) and aid gene (coding for AlaDH; SEQ ID NO: 34) was amplified together from the previous template pRSF-AlkJ-CvTA-AlaDH [Wu, S., Zhou, Y., et al., *Nat. Commun.* 7: 11917 (2016)] using primers CvTA-BamHI-BspHI-F (ACTGG-GATCCGATCATGATGCAAAAACAACGCACCACCT-CAC; SEQ ID NO: 35) and AlaDH-XhoI-R (ACTGCTC-GAGTTAAGCACCCGCCACAGATGATTCA; SEQ ID NO: 36). The PCR product was double digested with BspHI and XhoI, and then ligated to pCDF (digested with NcoI and XhoI) with T4 DNA ligase. The ligation product was transformed (heat shock) into *E. coli* T7 Expression competent cells to give pCDF-CvTA-AlaDH. The pCDF-CvTA-AlaDH and pACYC-SMO-SOI plasmids were co-transformed into competent cells of *E. coli* RARE strain [Kunjapur, A. M., Tarasova, Y., Prather, K. L. *J. Am. Chem. Soc.* 136: 11644-11654 (2014)] to give *E. coli* (StyABC-CvTA-AlaDH) co-expressing SMO, SOI, CvTA, and AlaDH. The competent cells of *E. coli* RARE strain were made according to the following protocol: it was grown in 1 mL LB media at 37° C. for overnight; then 100 μL culture was inoculated into 5 mL fresh LB media containing appropriate antibiotic at 37° C. until OD$_{600}$ reached 0.5 (about 2 h); then the cells were harvested by centrifugation (2500 g, 10 min, 4° C.) and resuspended in 1 mL cold CaCl$_2$ solution (0.1 M) on ice. The cell suspension was kept on ice and shaken at 90 rpm for 2 h, and then harvested by centrifugation (2500 g, 8 min, 4° C.) and resuspended in 0.2-0.5 mL cold CaCl$_2$ solution (0.1 M) to obtain the competent cells.

Example 7. Production of PEA From Sty via Cascade Biocatalysis by Using *E. coli* Containing Module 2-3 and Expressing SMO, SOI, CvTA and AlaDH The recombinant *E. coli* (StyABC-CvTA-AlaDH) was grown in 1 mL LB medium containing 50 mg/L chloramphenicol and 50 mg/L streptomycin at 37° C. and then inoculated into 50 mL M9 medium containing glucose (20 g/L), yeast extract (6 g/L), 50 mg/L chloramphenicol and 50 mg/L streptomycin. When OD$_{600}$ reached 0.6, 0.5 mM IPTG was added to induce the expressing of enzymes. The cells continued to grow and expressed protein for 12 h at 22° C. before they were harvested by centrifuge (4000 g, 10 mins). The cells were resuspended in 200 mM NaPB buffer (pH=8.0) to 10 g cdw/L with 2% glucose (for cofactor regeneration) and 200 mM NH$_3$—NH$_4$Cl (pH 8.25). To a 2 mL of aqueous system, a 2-mL n-hexadecane containing 80 mM Sty was added to the reaction system to form a second phase. The reaction was conducted at 30° C. and 300 rpm in a 100-mL flask for 10 h. 100 μL of aqueous phase samples were taken during the reaction and analyzed by reverse phase HPLC (Agilent Poroshell 120 EC-C18 column, acetonitrile:water: TFA=30:70:0.1, and flow rate 0.5 mL/min) to quantify the production of PEA in aqueous phase. 100 μL of organic phase samples were taken during the reaction and analyzed by GC-FID (Agilent HP-5 column, 70° C. increase to 200° C. at 25° C./min, increase to 250° C. at 50° C./min, hold for 1 min, and then increase to 270° C. at 20° C./min) to quantify Sty, SO, PA, 2-PE in organic phase. PEA was produced from Sty, and the best result is about 74 mM (93% yield) obtained in 10 h (FIG. 9). This result showed that our constructed recombinant strain is powerful catalyst for the cascade biotransformation of Sty to PEA.

Example 8. Efficient Production of Substituted PEA From Substituted Sty via Cascade Biocatalysis by Using *E. coli* (StyABC-CvTA-AlaDH)

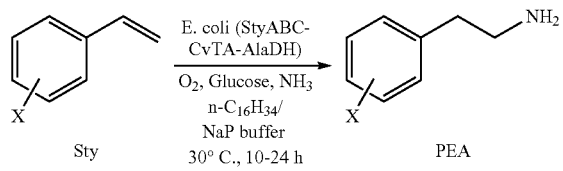

*E. coli* (StyABC-CvTA-AlaDH) was grown in 1 mL LB medium containing 50 mg/L chloramphenicol and 50 mg/L streptomycin at 37° C. and then inoculated into 50 mL M9 medium containing glucose (20 g/L), yeast extract (6 g/L), and 50 mg/L chloramphenicol and 50 mg/L streptomycin. When $OD_{600}$ reached 0.6, 0.5 mM IPTG was added to induce the expressing of enzymes. The cells continued to grow and expressed protein for 12 h at 22° C. before they were harvested by centrifuge (4000 g, 10 mins). The cells were resuspended in 200 mM NaPB buffer (pH=8.0) to 10 g cdw/L with 2% glucose (for cofactor regeneration) and 200 mM $NH_3$—$NH_4Cl$ (pH 8.25). To a 2 mL of aqueous system, a 2-mL n-hexadecane containing 20 mM of substituted Sty was added to the reaction system to form a second phase. The reaction was conducted at 30° C. and 300 rpm in a 100-mL flask for 10-24 hours. 100 μL of aqueous phase samples were taken during the reaction and analyzed by reverse phase HPLC (Agilent poroshell 120 EC-C18 column, acetonitrile:water: TFA=30:70:0.1, and flow rate 0.5 mL/min) to quantify the production of substituted PEA in aqueous phase. 100 μL of organic phase samples were taken during the reaction and analyzed by GC-FID (Agilent HP-5 column, 70° C. increase to 200° C. at 25° C./min, increase to 250° C. at 50° C./min, hold for 1 min, and then increase to 270° C. at 20° C./min) to quantify substituted Sty, SO, and PA in organic phase. As shown in Table 2, all the 12 substituted PEAs were produced in good to excellent yield 45-99% in 10-24 h. This prove the relative broad scope of the cascade biotransformation.

Example 9. Preparation of (Substituted) PEA From (Substituted) Sty by Using *E. coli* (StyABC-CvTA-AlaDH) in a 60 mL System

*E. coli* (StyABC-CvTA-AlaDH) was grown in 1 mL LB medium containing 50 mg/L chloramphenicol and 50 mg/L streptomycin at 37° C. and then inoculated into 50 mL M9 medium containing glucose (20 g/L), yeast extract (6 g/L), and 50 mg/L chloramphenicol and 50 mg/L streptomycin. After 5 h growth at 37° C., the 50-mL culture was expanded into 2 L M9 medium containing glucose (20 g/L), yeast extract (6 g/L), and 50 mg/L chloramphenicol and 50 mg/L streptomycin and continue culture at 37° C. When $OD_{600}$ reached 0.6, 0.5 mM IPTG was added to induce the expressing of enzymes. The cells continued to grow and expressed protein for 12 h at 22° C. before they were harvested by centrifuge (4000 g, 10 mins). The cells were resuspended in 200 mM NaPB buffer (pH=8.0) to 10 g cdw/L with 2% glucose (for cofactor regeneration) and 200 mM $NH_3$—$NH_4Cl$ (pH 8.25). To a 50 mL of aqueous system, a 10-mL n-hexadecane containing 50 mM Sty was added to the reaction system to form a second phase. The reaction was conducted at 30° C. and 300 rpm in a 1-L flask for 24 h. After reaction, the two phase was separated by centrifugation (4000 g, 15 mins). The aqueous phase was adjusted to pH=13 with NaOH and extracted with 50 mL ethyl acetate for three times. All the ethyl acetate was combined, dried over $Na_2SO_4$ and evaporated. The residue was further purified by flash chromatography with dichloromethane: methanol: triethylamine=100:5:1. The fractions were combined and evaporated to get 236 mg of pure PEA with 78% isolated yield. Using the similar process, p-fluoro-PEA, p-methyl-PEA, and m-methyoxyl-PEA were also isolated in 68%, 71%, and 82% yield, respectively.

Example 10. Genetic Engineering of *E. coli* Containing Module 2-4 and Expressing SMO, SOI, and EcALDH The padA gene coding EcALDH (phenylacetaldehyde reductase; SEQ ID NO: 10) from *E. coli* was amplified using primers EcALDH-Notl-RBS-F (ACTGCGGCCGCTAA-GGAGATATATAATGAC AGAGCCGCATGTAGCA-GTAT; SEQ ID NO: 37) and EcALDH-Xhol-R (ACTG

TABLE 2

Conversion of substituted styrene to substituted PEAs with *E. coli* (StyABC- CvTA-AlaDH).

| Entry | Substrate | Product | Conv. to PEA [%][b] | Chemoselectivity $NH_2$:OH[b] | Regioselectivity 2-$NH_2$:1-$NH_2$[c] |
|---|---|---|---|---|---|
| 1 | Sty | H | 98 | 96:4 | >99:1 |
| 2 | o-F-Sty | o-F-PEA | 94 | 99:1 | >99:1 |
| 3 | m-F-Sty | m-F-PEA | >99 | 99:1 | >99:1 |
| 4 | p-F-Sty | p-F-PEA | 96 | 98:2 | >99:1 |
| 5 | m-Cl-Sty | m-Cl-PEA | 86 | 98:2 | >99:1 |
| 6 | p-Cl-Sty | p-Cl-PEA | 76 | 98:2 | >99:1 |
| 7 | m-Br-Sty | m-Br-PEA | 45 | 97:3 | >99:1 |
| 8 | p-Br-Sty | p-Br-PEA | 60 | 98:2 | >99:1 |
| 9 | m-Me-Sty | m-Me-PEA | 93 | 97:3 | >99:1 |
| 10 | p-Me-Sty | p-Me-PEA | 99 | 98:2 | >99:1 |
| 11 | m-OMe-Sty | m-OMe-PEA | >99 | 99:1 | >99:1 |
| 12 | p-OMe-Sty | p-OMe-PEA | 94 | 96:4 | >99:1 |

[a] Sty (20 mM in organic phase) was transformed with resting cells (10 g cdw/L) in NaP buffer (200 mM, pH 8, 2% glucose) and n-hexadecane (1:1) at 30° C. and 250 rpm for 10 h.
[b] Determined by HPLC analysis of aqueous phase and GC-FID analysis of organic phase.
[c] 1-phenylethylamines were not detected.
[d] 24 h reaction time.

CTCGAG TTAATACCGT ACACACACCGACTTAG; SEQ ID NO: 38) and Phusion DNA polymerase (available from Thermo). The PCR product were double digested with NotI and XhoI, and then ligated to same digested pRSF-SMO-SOI plasmid (see example 1) with T4 DNA ligase. The ligation product was transformed (heat shock) into *E. coli* T7 Expression competent cells (available from New England Biolabs) to give pRSF-SMO-SOI-EcALDH. This module 2-4 was sub-cloned to other three vectors by the following procedures. Module 2-4 operon was amplified with primers StyA-BspHI-F (ACTGTC ATGAAAAAGCGTATCGGT-ATTGTTGG; SEQ ID NO: 31) and EcALDH-XhoI-R (ACTGCTCGAGTTAATACCGTACACACACCGACT-TAG; SEQ ID NO: 38), digested with BspHI and XhoI, and then ligated to double digested pACYCduet, pCDFduet, and pETduet (available from Novagen). The transformation of these products gave pACYC-SMO-SOI-EcALDH, pCDF-SMO-SOI-EcALDH, and pET-SMO-SOI-EcALDH respectively.

Example 11. Production of PAA From Sty via Cascade Biocatalysis by Using *E. coli* Containing Module 2-4 and Expressing SMO, SOI, and EcALDH The recombinant *E. coli* (StyABC-EcALDH) containing the plasmid pRSF-SMO-SOI-EcALDH was grown in 1 mL LB medium containing 50 mg/L kanamycin at 37° C. and then inoculated into 50 mL M9 medium containing glucose (20 g/L), yeast extract (6 g/L), and 50 mg/L kanamycin. When $OD_{600}$ reached 0.6, 0.5 mM IPTG was added to induce the expressing of enzymes. The cells continued to grow and expressed protein for 12 hr at 22° C. before they were harvested by centrifuge (4000 g, 10 mins). The cells were resuspended in 400 mM KPB buffer (pH=8.0) to 15 g cdw/L with 0.5% glucose (for cofactor regeneration). To a 2 mL of aqueous system, a 2 mL ethyl oleate containing 130 mM Sty was added to the reaction system to form a second phase. The reaction was conducted at 30° C. and 300 rpm in a 100-mL flask for 6 h. 100 μL of aqueous phase samples were taken during the reaction and analyzed by reverse phase HPLC (Agilent poroshell 120 EC-C18 column, acetonitrile: water=50:50, and flow rate 0.5 mL/min) to quantify the production of PAA in aqueous phase. 100 μL of organic phase samples were taken during the reaction and analyzed by GC-FID (Agilent HP-5 column, 70° C. increase to 200° C. at 25° C./min, increase to 250° C. at 50° C./min, hold for 1 min, and then increase to 270° C. at 20° C./min) to quantify Sty, SO, PA in organic phase. PAA was produced from Sty, and the best result is about 122 mM (94% yield) obtained in 6 h (FIG. 12). This result showed that our constructed recombinant strain is powerful catalyst for the cascade biotransformation of Sty to PAA.

Example 12. Preparation of (Substituted) PAA From (Substituted) Sty by Using *E. coli* (StyABC-EcALDH) in a 48 mL System

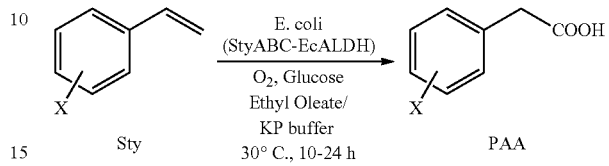

*E. coli* (StyABC-EcALDH) was grown in 1 mL LB medium containing 50 mg/L kanamycin at 37° C. and then inoculated into 50 mL M9 medium containing glucose (20 g/L), yeast extract (6 g/L), and 50 mg/L kanamycin. After 5 h growth at 37° C., the 50-mL culture was expanded into 2 L M9 medium containing glucose (20 g/L), yeast extract (6 g/L), and 50 mg/L kanamycin and continue culture at 37° C. When $OD_{600}$ reached 0.6, 0.5 mM IPTG was added to induce the expressing of enzymes. The cells continued to grow and expressed protein for 12 hours at 22° C. before they were harvested by centrifuge (4000 g, 10 mins). The cells were resuspended in 400 mM KPB buffer (pH=8.0) to 15 g cdw/L with 0.5% glucose (for cofactor regeneration). To a 40-mL of aqueous system, an 8-mL ethyl oleate containing 25-100 mM of substituted Sty was added to the reaction system to form a second phase. The reaction was conducted at 30° C. and 300 rpm in a 250-mL tri-baffled flask for 10 hours. 100 μL of aqueous phase samples were taken during the reaction and analyzed by reverse phase HPLC (Agilent poroshell 120 EC-C18 column, acetonitrile: water=50:50, and flow rate 0.5 mL/min) to quantify the production of substituted PAA in aqueous phase. As shown in Table 3, all the 12 substituted 2-PEs were produced in good to excellent yield 85-99% in 10 h. This proved the relative broad scope of the cascade biotransformation. After reaction, the two phases were separated by centrifugation (4000 g, 15 mins). The aqueous phase was adjusted to pH=2 with HCl and extracted with 100 mL ethyl acetate for two times. The ethyl acetate fractions were combined, dried over $Na_2SO_4$ and evaporated. The PAAs were purified by flash chromatography. Pure PAA was obtained at 82% isolated yield (Table 3).

TABLE 3

Conversion of substituted styrene to substituted PAAs with *E. coli* (StyABC-EcALDH).

| Entry | Substrate | Scale KPB + EO [mL] | Substrate Conc. [mM] | Product | Conv. to PAA [%] | Isolated yield [%] |
|---|---|---|---|---|---|---|
| 1 | Sty | 100 + 20 | 100 | PAA | 96 | 82 |
| 2 | o-F-Sty | 40 + 8 | 50 | o-F-PAA | 98 | 71 |
| 3 | m-F-Sty | 40 + 8 | 50 | m-F-PAA | >99 | 73 |
| 4 | p-F-Sty | 40 + 8 | 50 | p-F-PAA | 98 | 76 |
| 5 | m-Cl-Sty | 40 + 8 | 50 | m-Cl-PAA | 94 | 81 |
| 6 | p-Cl-Sty | 40 + 8 | 50 | p-Cl-PAA | 85 | 75 |
| 7 | m-Br-Sty | 40 + 8 | 25 | m-Br-PAA | 91 | 77 |
| 8 | p-Br-Sty | 40 + 8 | 25 | p-Br-PAA | 87 | 71 |
| 9 | m-Me-Sty | 40 + 8 | 50 | m-Me-PAA | 99 | 67 |
| 10 | p-Me-Sty | 40 + 8 | 50 | p-Me-PAA | 98 | 56 |
| 11 | m-OMe-Sty | 40 + 8 | 50 | m-OMe-PAA | >99 | 66 |
| 12 | p-OMe-Sty | 40 + 8 | 50 | p-OMe-PAA | >99 | 52 |

Example 13. Genetic Engineering of E. coli Expressing SMO, SOI and ADH9v1 (StyABC-ADH9v1)

Gene coding ADH9v1 (SEQ ID NO: 39), as reported in [P. Könst, H. Merkens, et al., *Angew. Chem. Int. Ed.* 51: 9914-9917 (2012)], was amplified using the primers ADH9v1-Hindll-RBS-F: ACTGAAGCTTTAAGGAGA-TATATCATGAAAAATCGTGTTGC CTTTGTTAC (SEQ ID NO: 40) and ADH9v1-Xhol-R: ACTGCTCGAGTTAGT-TAAACACCATACCACCAT (SEQ ID NO: 41) and Phusion DNA polymerase (available from Thermo). The PCR product were double digested with HindIII and Xhol, and then ligated to same digested pRSF-SMO-SOI plasmid (see Example 1) with T4 DNA ligase. The ligation product was transformed (heat shock) into *E. coli* T7 Expression competent cells (available from New England Biolabs) to give *E. coli* (StyABC-ADH9v1) or (pRSF-SMO-SOI-ADH9v1).

Example 14. Preparation of (S)-2-Arylpropionic Acids From α-Methylstyrene Derivatives With *E. coli* (StyABC-ADH9v1)

Freshly prepared *E. coli* (StyABC-ADH9v1) cells were resuspended to 20 g cdw/L in KP buffer (200 mM, pH 8.0). 100 mL of the cell suspension were mixed with 10 mL of n-hexadecane in a tri-baffled flask (500 mL). α-Me-Sty (2 mmol), or p-F-α-Me-STy-p-Me-α-Me-Sty (0.5 mmol) was added to start the reaction at 300 rpm and 30 8° C. for 24 h. Aqueous phase samples (100 mL) were separated by centrifugation (13000 g, 3 min), diluted with 400 mL TFA solution (0.5%) and 500 mL acetonitrile (with 2 mM benzyl alcohol), and analyzed by chiral HPLC to quantify the concentration and ee of 2-Phenylpropanoic acid-p-Me-α-Me-paa. At the end of the reaction, the mixture was subjected to centrifugation (4000 g, 15 min) to collect the aqueous phase. The reaction flask, the cells and n-hexadecane were washed with water (20 mL). The aqueous phase and washed water were combined, adjusted to pH≤2 with HCl, saturated with NaCl, and then extracted with ethyl acetate (3×100 mL). The ethyl acetate was collected, dried over $Na_2SO_4$, and subjected to evaporation by using a rotary evaporator. The crude product was purified by flash chromatography on a silica gel column with an eluent consisting of n-hexane: ethyl acetate of 5:1 and acetic acid (0.5% as additive) ($R_f$=0.2-0.3). The collected fractions were subjected to GC-FID analysis to confirm the purity. The desired fractions were combined, subjected to evaporation (n-heptane was added to remove acetic acid by forming azeotrope), and dried overnight under vacuum.

Example 15. One-Pot Synthesis of (S)-Arylpropionic Acids From α-Methylstyrene Derivatives With *E. coli* (StyABC-ADH9v1)

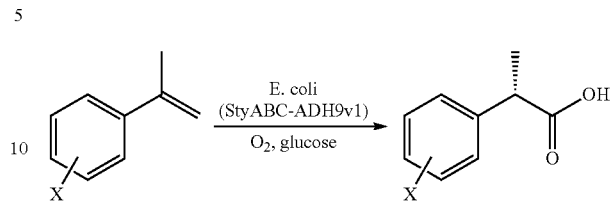

Asymmetric cascade oxidation of α-methylstyrene (20 mM) was examined with resting cells of *E. coli* (StyABC-ADH9v1) under different conditions on a small scale (FIG. 14). The ee of (S)-2-Phenylpropanoic acid was excellent (98-99%) under all these conditions, and high conversion (80%) was achieved with resting cells (20 g cdw/L) and no glucose.

To demonstrate the cascade oxidation for asymmetric synthesis of 2-arylpropionic acid, *E. coli* (StyABC-ADH9v1) resting cells (20 g cdw/L) were employed to transform α-Methylstyrene (20 mM) in a larger system consisting of 100 mL KP buffer and 10 mL n-hexadecane. After reacting for 24 hours, (S)-2-Phenylpropanoic acid was produced in 82% conversion (Table 4). Work-up, extraction with ethyl acetate, and purification by flash chromatography gave 195 mg of pure (S)-2-Phenylpropanoic acid in 65% isolated yield. The ee of (S)-2-Phenylpropanoic acid is excellent (98%). The cascade biooxidation was further applied to transform ring-substituted α-methylstyrenes (S)-p-F-α-Me-PAA-(S)-p-Me-α-Me-PAA (5 mM) in the same system of 100 mL KP buffer and 10 mL n-hexadecane. (S)-p-F-α-Me-PAA-(S)-α, 4-Dimethylphenylacetic acid were successfully produced in 67-75% conversion, and similar work-up, extraction, and purification afforded pure (S)-p-F-α-Me-PAA-(S)-p-Me-α-Me-PAA in 46-52% isolated yield. The ees of (S)-4-F-α-Me-PAA and (S)-p-Me-α-Me-PAA were also excellent (97-98%), while the ee of (S)-p-Cl-α-Me-PAA is slightly lower (92%). These results clearly demonstrated that the epoxidation-isomerization-oxidation cascade is highly regio- and stereo-selective for the conversion of 2-arylpropenes to give (S)-2-arylpropionic acids. This unique one-pot asymmetric oxidation has no chemical counterpart thus far.

TABLE 4

One-Pot Synthesis of (S)-Arylpropionic Acids from α-Methylstyrene Derivatives with *E. coli* (StyABC-ADH9v1)

| Entry | Substrate | Conc. [mM] | Product | Conversion to Product [%] | ee [%] | Isolated yield [%] |
|---|---|---|---|---|---|---|
| 1 | α-Me-Sty | 20 | (S)-2-Phenylpropanoic acid | 82 | 98 | 65 |
| 2 | p-F-α-Me-Sty | 5 | (S)-p-F-α-Me-PAA | 75 | 97 | 49 |
| 3 | p-Cl-α-Me-Sty | 5 | (S)-p-Cl-α-Me-PAA | 67 | 92 | 46 |
| 4 | p-Me-α-Me-Sty | 5 | (S)-p-Me-α-Me-PAA | 73 | 98 | 52 |

Conversion to 4 [%] and ee [%] are determined by chiral HPLC analysis.

One-Pot Production of Natural 2-PE From L-Phe

Example 16. Genetic Engineering of *E. coli* Containing Module 1 and Module 2-2 and Expressing PAL, PAD, SMO, SOI, and PAR AtPAL2 from *Arabidopsis thaliana* was chosen for the deamination of L-phenylalanine, while AnPAD (fdc1 and pad1) from *Aspergillus niger* was selected for decarboxylation of cinnamic acid. Both genes were subsequently cloned together in compatible plasmids to provide the first cascade containing Module 1.

The synthesized gene of AnFDC (fdc1) with nucleic acid sequence (SEQ ID NO: 42) encoding AnPAD protein sequence (SEQ ID NO: 43) was amplified using primers "AnFDC-BspHI-F: ACTGTCATGAGCGCGCAACCTGC-GCACCTG" (SEQ ID NO: 44) and "AnFDC-EcoRI-R: ACTGGAATTCTTAGTTACTGAAGCCCATTTTGGTC" (SEQ ID NO: 45) with Phusion DNA polymerase. The PCR product was double-digested with BspHI and EcoRI, and then ligated to the NcoI and EcoRI digested pRSFDuet-1 with T4 DNA ligase. The ligation product was transformed into *E. coli* T7 Expression competent cells to give pRSF-AnFDC. On the other hand, the synthesized gene of AnPAD (pad1) with nucleic acid sequence (SEQ ID NO: 16) encoding AnPAD protein sequence (SEQ ID NO: 14) was amplified using primers "AnPAD-EcoRI—RBS-F: ACTG GAATTCTAAGGAGATATATCATGTTCAACTCACTT-CTGTCCGGC" (SEQ ID NO: 46) and "AnPAD-PstI-R: ACTGCTGCAGTTATTTTTCCCAACCATTCCAACG" (SEQ ID NO: 47). The PCR product was double digested with EcoRI and PstI, and then ligated to the same digested pRSF-AnFDC with T4 DNA ligase. The ligation product was transformed into *E. coli* T7 Expression competent cells to give pRSF-PAD plasmid. Then, the gene of AtPAL2 with nucleic acid sequence (SEQ ID NO: 15) encoding PAL protein sequence (SEQ ID NO: 13) was amplified from the cDNA library of *Arabidopsis thaliana* (purchased from ATCC 77500) using primers "AtPAL-NdeI-F: ACTG CATATGGATCAAATCGAAGCAATGTTGTG" (SEQ ID NO: 48) and "AtPAL-XhoI-R: ACTGCTCGAGTTATTT-TTCCCAACCATTCCAACG" (SEQ ID NO: 49). The PCR product was double digested with NdeI and XhoI, and then ligated to the same digested pRSF-PAD with T4 DNA ligase. The ligation product was transformed into *E. coli* T7 Expression competent cells to give pRSF-PAD-PAL plasmid. PAD-PAL was also sub-cloned to the other three vectors by the following procedure. PAD-PAL was amplified with primers "AnFDC-BspHI-F: ACTGTCATGAGCGCGCAACCTG-CGCACCTG" (SEQ ID NO: 44) and "AtPAL-XhoI-R: ACTGCTCGAGTTATTTTTCCCAACCATTCCAACG" (SEQ ID NO: 49), digested with BspHI and XhoI, and then ligated to NcoI and XhoI digested pACYCDuet-1, pCDF-Duet-1, and pETDuet-1. The transformation of these products gave pACYC-PAD-PAL, pCDF-PAD-PAL, and pET-PAD-PAL, respectively.

For the second cascade containing Module 2-2, pRSF-SMO-SOI-PAR, pACYC-SMO-SOI-PAR, pCDF-SMO-SOI-PAR, and pET-SMO-SOI-PAR were produced according to Example 2.

In order to achieve an equal enzyme expression in the *E. coli* strain, all 5 main enzymes were divided into 2 different modules, PAL-PAD and SMO-SOI-PAR using 4 different plasmids each, pACYC, pCDF, pET, and pRSF, respectively. The twelve recombinant plasmids were then transformed to *E. coli* T7 competent cells to provide 12 *E. coli* strains, each co-expressing PAL, PAD, SMO, SOI, and PAR. Plasmids for Module 1 and Module 2-2 combined plasmids for Module 1 and Module 2-2 are shown in Table 5.

TABLE 5

Engineering of recombinant *E. coli* expressing PAL, PAD, SMO, SOI, and PAR using two modules (PAL_PAD and SMO_SOI_PAR) with different plasmids

| Plasmid for PAL_PAD (M1) | Plasmid for SMO_SOI_PAR (M2-2) | Combined plasmids for Module 1 and Module 2-2 |
|---|---|---|
| pACYC (M1) | pACYC (M2-2) | pACYC (M1)_pCDF (M2-2) (AC) |
| pCDF (M1) | pCDF (M2-2) | pACYC (M1)_pET (M2-2) (AE) |
| pET (M1) | pET (M2-2) | pACYC (M1)_pRSF (M2-2) (AR) |
| pRSF (M1) | pRSF (M2-2) | pCDF (M1)_pACYC (M2-2) (CA) |
| | | pCDF (M1)_pET (M2-2) (CE) |
| | | pCDF (M1)_pRSF(M2-2) (CR) |
| | | pET (M1)_pACYC (M2-2) (EA) |
| | | pET (M1)_pCDF (M2-2) (EC) |
| | | pET (M1)_pRSF (M2-2) (ER) |
| | | pRSF (M1)_pACYC (M2-2) (RA) |
| | | pRSF (M1)_pCDF (M2-2) (RC) |
| | | pRSF (M1)_pET (M2-2) (RE) |

Example 17. Screening of Recombinant *E. coli* Strains for 2-PE Production

Figure 15:
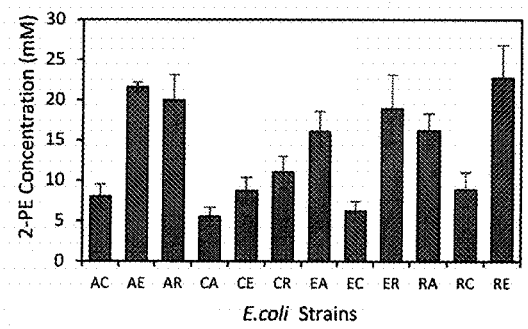
FIG. 15 shows the screening of 12 constructed *E. coli* recombinant strains (10 g cdw/L for 2-PE production from L-phenylalanine (50 mM) in 2 h in biphasic system (n-hexadecane as organic solvent).

One-pot synthesis of 2-PE production via resting cells biotransformation was conducted in furtherance to test the activity of all those 12 strains (Table 5). KP buffer (potassium phosphate, 100 mM, pH 8) in 10 g cdw/L cell density containing 50 mM of L-phenylalanine was used as initial substrate, together with n-hexadecane as the organic phase, in a total volume of 4 ml (1:1). Glucose (0.5%) was added to the reaction mixture for the purpose of NADH regeneration via cellular metabolism. As shown in FIG. 15, all 12 strains was successfully produced 2-PE with different concentrations due to the difference in gene dosage effect which will cause on the difference on the plasmid copy number during the replication within cell growth. The *E. coli* strains containing pRSF-PAL-PAD_pET-SMO—SOI-PAR gave the best conversion among all other 11 strains, hence it was selected for further investigation.

Example 18. 2-PE Product Inhibition

Apart from the achievements that have been reported so far, most of the 2-PE production is hindered by the product toxicity. Concentrations of 2-PE higher than 2-3 gr/L will inhibit the cells, causing a low conversion of the product in the end of the biotransformation. [Etschmann, M., Bluemke, W., et al., *J. Appl. Microbiol. Biotechnol.* 59: 1-8; (2002); Hua, D., Xu, P. *Biotechnol. Adv.* 29: 654-660 (2011); Hua, D. L, Liang, X. H., et al., *Asian J. Chem.* 25(11): 5951-5954 (2013); Stark, D., Zala, D., et al., *Enzyme Microb. Technol.* 32: 212-223 (2003)] 2-PE will aim the cell membrane once it is formed during the biotransformation, hence enlarging the membrane fluidity and deflating both glucose and substrate uptake [Seward, R., Willets, J. C., Dinsdale, M. G., and Lloyd, D. *J Inst Brew.* 102: 439-443 (1996)]. Protein and RNA inhibitions towards *E. coli* were also reported before due to the exceeding concentration of 2-PE [Luchini, J. J., Corre, J., and Cremieux, A. *Res. Microbiol.* 141: 499-510 (1990)].

The product inhibition was investigated by adding different concentration of 2-PE to the cell suspension (10 g cdw/L) of *E. coli* (pRSF-PAL-PAD_pET-SMO-SOI-PAR) in KP buffer (100 mM, pH 8.0) containing 0.5% glucose in aqueous phase with n-hexadecane as the organic phase, followed by the incubation at 30° C. and 250 rpm for 3 h.

Figure 17A:
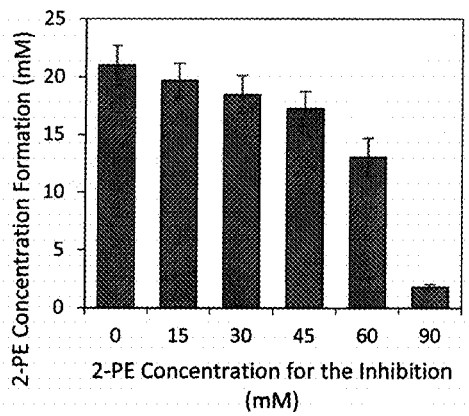
FIGS. 17a and 17b show (FIG. 17a) 2-PE product inhibition test with *E. coli* cells (R-PAL-PAD_E-SMO-SOI-PAR) treated with 2-PE in different concentrations for 3 hours before performing the reaction and (FIG. 17b) shows the Apparent Kinetics of the whole-cell *E. coli* (R-PAL-PAD_E-SMO-SOI-PAR). The reaction for FIG. 17b was done at 30° C. and 250 rpm in 2 ml KP buffer (100 mM, pH 8.0) containing 0.5% (w/v) glucose, 5 g cdw/L of cell suspension, 10 mM L-phenylalanine, and (•) 0 or (▲) 3 mM of 2-PE in the aqueous phase, with n-hexadecane in the organic phase.
Figure 17B:
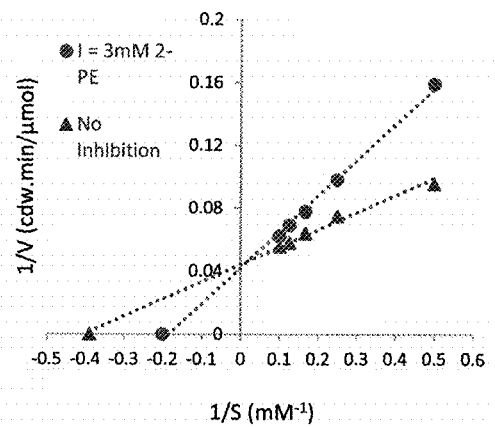

Referring to FIG. 17(a), the results clearly demonstrated that 2-PE was toxic to the cells and hindered the production of 2-PE. 2-PE concentrations above 30 mM in the aqueous phase started to inhibit the biotransformation, while almost no activity was observed when the cells were pretreated with 90 mM 2-PE before performing the biotransformation. Biotransformation was done in aqueous phase with KP buffer (100 mM, pH 8.0) containing cell suspension (10 g cdw/l), 0.5% glucose, and 50 mM L-phenylalanine as initial substrate while n-hexadecane as the organic phase (250 rpm, 2 h, 30° C.)

Figure 16:
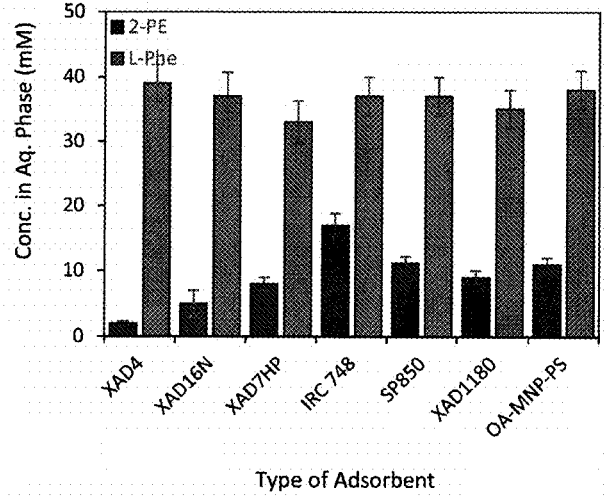
FIG. 16 shows the adsorption of 2-PE and L-phenylalanine by different resins. All resins were used in 10% (w/v). Initial concentration of 2-PE and L-phenylalanine were each set in 50 mM inside the KP buffer (100 mM, pH 8.0) in 30° C. for 2 h. Values are the mean of triplicate and the error bars indicate the standard deviation value.

To further investigate the product inhibition, the apparent kinetics of the whole-cells was measured and determined using Lineweaver-Burk plot. 2-PE concentration of 3 mM was used for 15 minutes in order to determine the kinetic, thus the product toxicity towards the cells could be neglected. Competitive inhibition was shown (FIG. 16), with the apparent Ki value of 4.8 mM for 2-PE. Apparent Vmax value was found to be 22.8 µmol/min/g CDW, while the apparent Km value was 2.57.

Example 19. Screening and Selection of Organic Solvent for Partitioning 2-PE

In-situ product removal technique via extraction have been conducted to remove the obtained 2-PE from the aqueous phase and make its concentration below the inhibitory level. We investigated different type of organic solvents and ionic liquids to perform the extractive biotransformation for 2-PE production via styrene-derived pathway from L-phenylalanine, starting from the analysis of their partition coefficients in the biphasic system. Product and substrate coefficient partitions in organic and aqueous phase were determined by adding different concentration of 2-PE and L-phenylalanine, respectively, into KP buffer (100 mM, pH 8.0) together with the respective organic solvents. Reaction mixtures were incubated for 1 h (280 rpm, 30° C.).

Figure 18A:
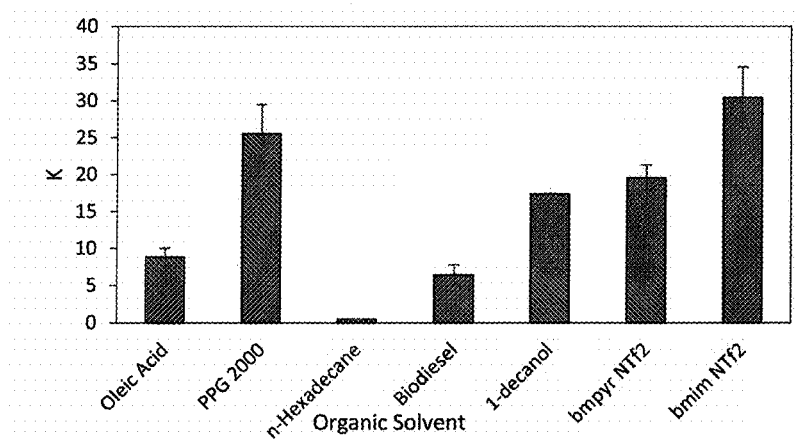
FIGS. 18a and 18b show (FIG. 18a) partition coefficient of 2-PE in aqueous-organic biphasic system. Partition coefficient measured at a phase ratio of 1:1. KP buffer (100 mM, pH 8.0) was utilized as the aqueous buffer. All data were obtained from the mean values of triplicate with standard deviations through HPLC analysis. K value for L-phenylalanine was observed as ~0 in all the respective organic solvents mentioned and (FIG. 18b) screening of 7 different organic solvent for the one-pot production of 2-PE from L-phenylalanine with the KP buffer (100 mM, pH 8.0) containing 0.5% glucose and 50 mM L-phenylalanine.
Figure 18B:
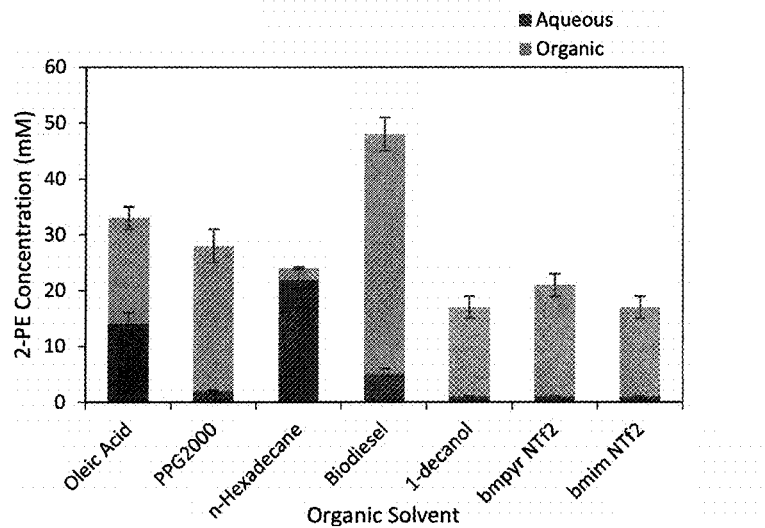

Results in FIG. 18 (a) show that most of the organic solvents used were able to extract 2-PE from the aqueous phase. It is shown through the K value which is >>>1, which indicated that most of the 2-PE was extracted to the organic phase. However, n-hexadecane appeared to have much lower partition coefficient, hence reducing the extraction efficiency.

Further investigation was conducted in order to determine the biocompatibility of the organic solvents towards the biocatalyst. The E. coli cell pellets (pRSF-PAL-PAD_pET-SMO—SOI-PAR, 10 g cdw/L) in KP buffer (100 mM, pH 8.0) containing 0.5% glucose and 50 mM L-Phe were used to perform the biotransformation by utilizing the respective organic solvents for 24 h (280 rpm, 30° C.). From FIG. 18(b), it is shown that all of organic solvents used in the biotransformation were biocompatible and could enhance 2-PE production up to 150%. Biodiesel was proven as the best organic solvent and this can clearly be seen from the highest 2-PE obtained after 24 h of biotransformation. Apart from n-hexadecane, all organic solvents used were also still be able to extract 2-PE while the biocatalysts performed the reaction. This clearly demonstrated that extractive biotransformation enables to significantly improve the 2-PE productivity.

Example 20. Preparation and Characterization of Nano-Solid Adsorbent

The use of a magnetic adsorbent consisting of iron oxide core and benzene ring functional groups on the surface was investigated. Polystyrene was employed to coat the OA-MNP in order to protect the iron oxide cores.

Figure 19A:
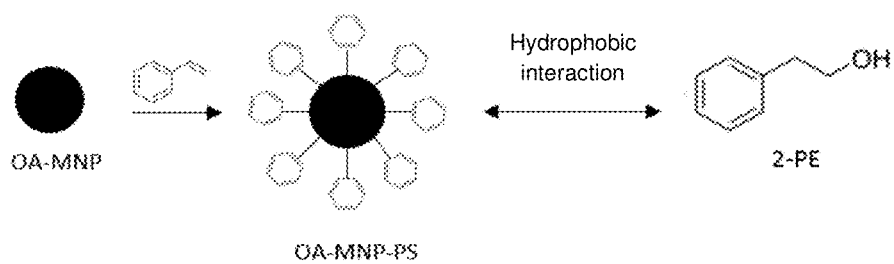
FIGS. 19a to 19e show (FIG. 19a) synthesis of OA-MNP-PS, (FIG. 19b and FIG. 19c) TEM and DLS, respectively, of OA-MNP and (FIG. 19d and FIG. 19e) TEM and DLS, respectively, of OA-MNP-PS.
Figure 19B:
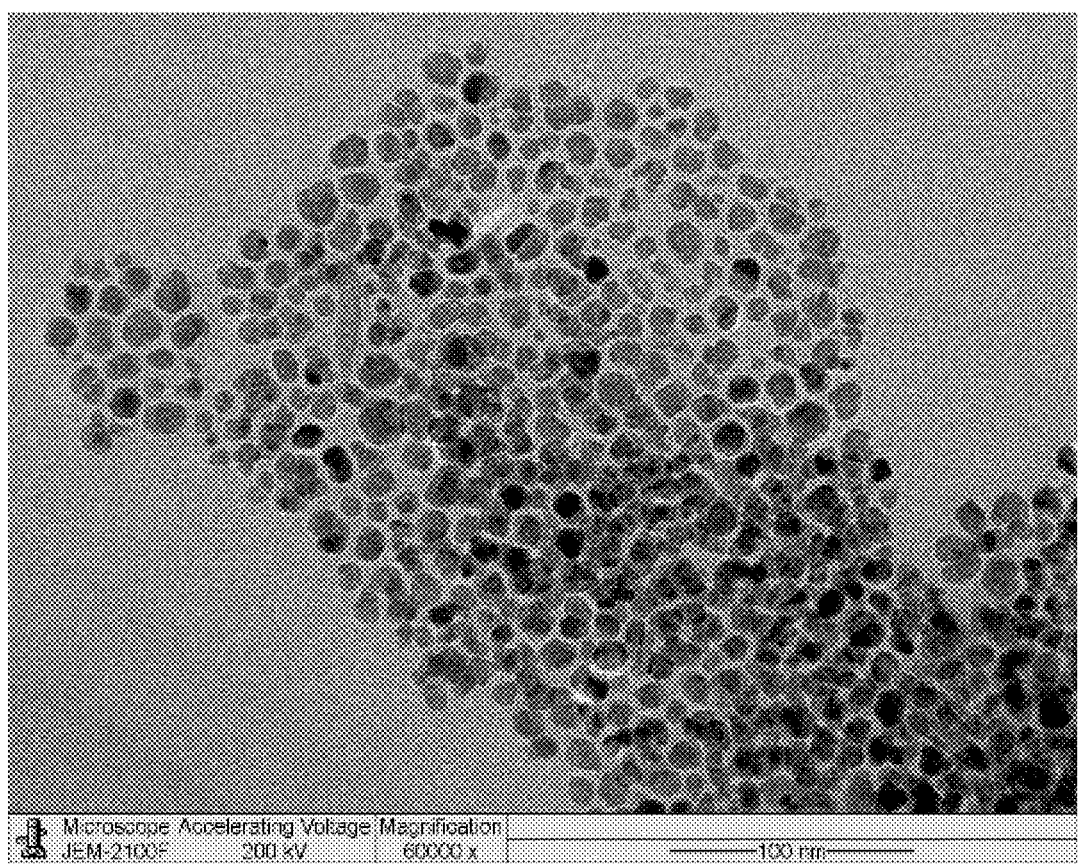
Figure 19C:
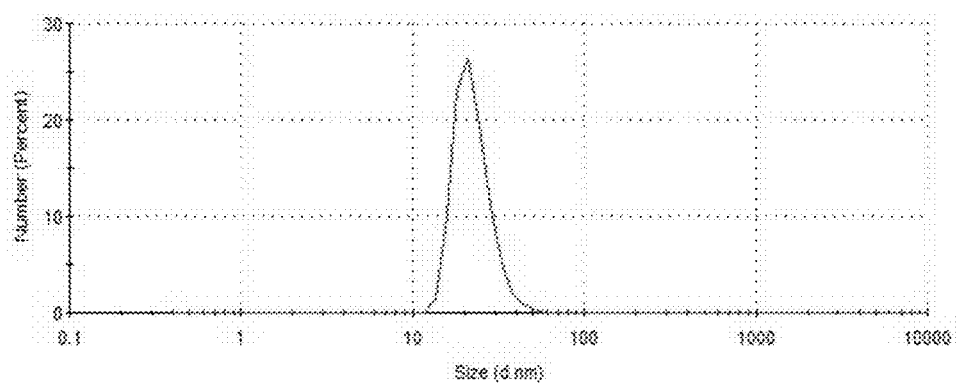
Figure 19D:
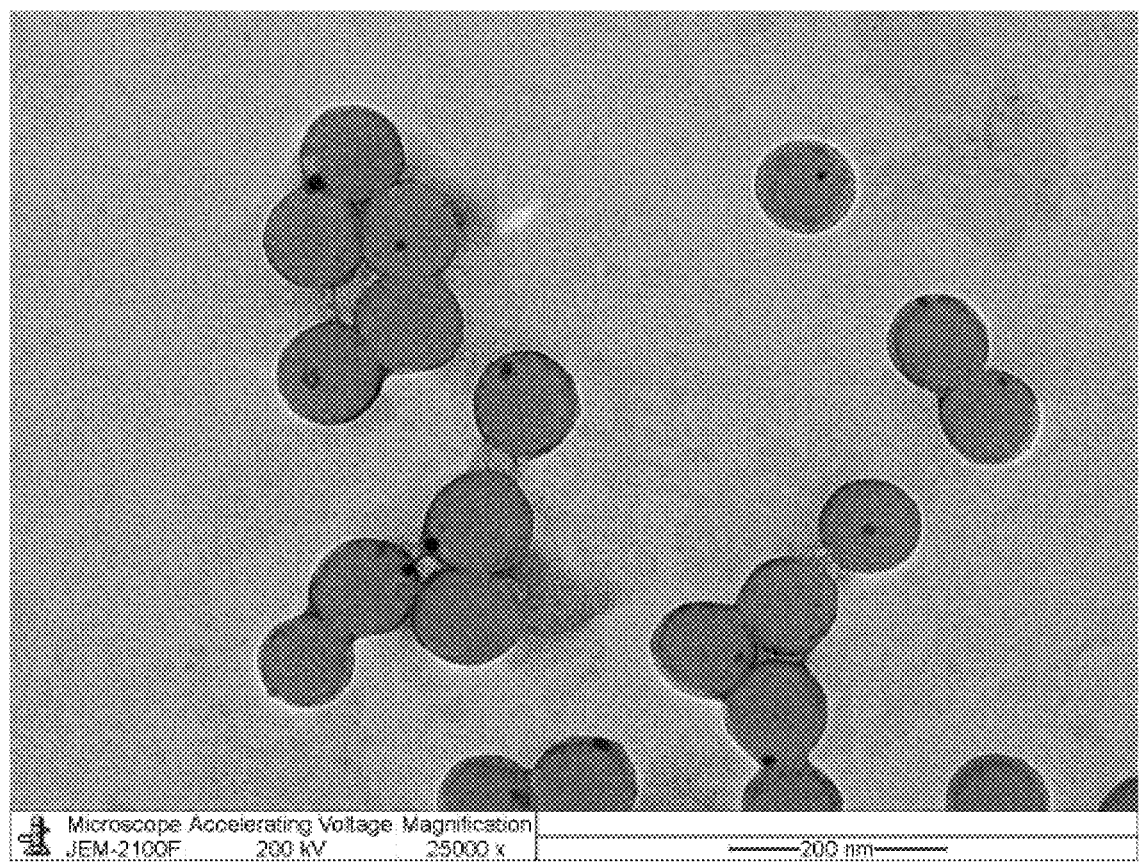
Figure 19E:
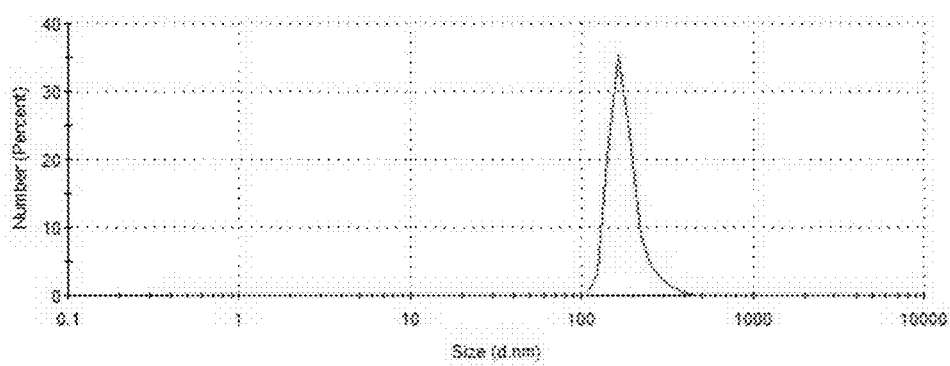

The synthesis of the OA-MNP-PS is shown in FIG. 19a. The OA-MNP and OA-MNP-PS were found to have a diameter of 12 nm and 118 nm, respectively, as well as a hydrodynamic size of 23 nm and 180 nm, respectively (FIGS. 19c and 19e). Separation was done by magnetic force or centrifugation (30 min, 13 000 g). The investigation was performed by analysing the product adsorption towards the synthesized MNP through the hydrophobic interactions.

Example 21. Adsorbent Screening

In-situ product adsorption (ISPA) can be applied as an in-situ product removal (ISPR) alternative technique, where resins or other adsorption media are implemented to minimize the 2-PE product inhibition. Product concentration increased up to 6.2 g/l when macroporous resin D101 was applied during the biotransformation. However, ISPA also suffers from limitation, such as a low specificity and adsorption capacity for 2-PE [Mei, J., Min, H., and Lu, Z. *Process Biochemistry*. 44: 886-890 (2009)].

Figure 20:
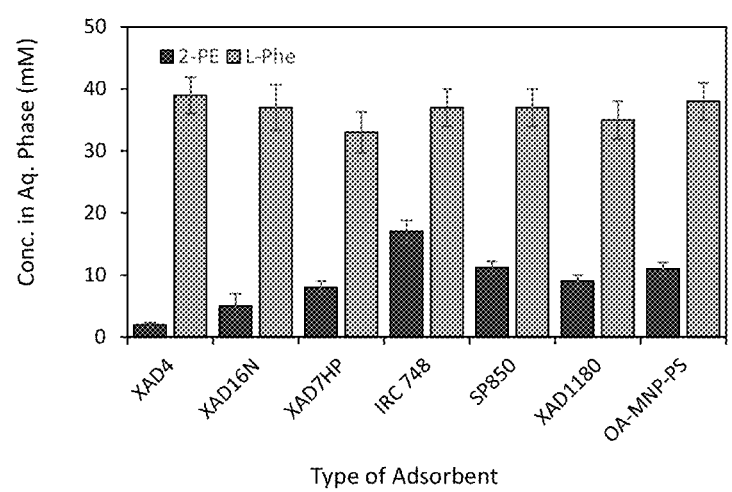
FIG. 20 shows the adsorption of 2-PE and L-phenylalanine by different resins. All resins were used in 10% (w/v). Initial concentration of 2-PE and L-phenylalanine were each set in 50 mM inside the KP buffer (100 mM, pH 8.0) in 30° C. for 2 h. Values are the mean of triplicate and the error bars indicate the standard deviation value.

Seven different adsorbents were used, including OA-MNP-PS. As shown in FIG. 20, the 2-PE concentration in the aqueous phase remains low below the inhibitory level, which clearly demonstrated that most of the 2-PE was adsorbed into the adsorbent surface through hydrophobic interactions. The adsorption capacity for L-phenylalanine was significantly lower than 2-PE due to its hydrophilic structure. XAD4 resins gave the best performance among all the other 5 micro-size resins tested due to its cross-linked hydrophobic polystyrene structure, higher surface area, low porosity, as well as its application to remove hydrophobic compounds in pharmaceuticals. Surprisingly, the use of MNPs enables good selectivity towards 2-PE as a nano-scale adsorbent.

Figure 21A:
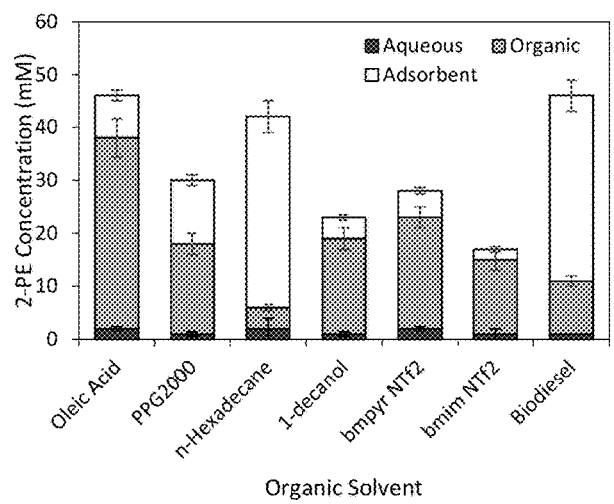
FIGS. 21a to 21c show (FIG. 21a) biotransformation of L-phenylalanine (50 mM) to 2-PE with tri-phasic in-situ product removal via extraction and MNPs adsorption in 1 pot, (FIG. 21b) biotransformation of L-phenylalanine (50 mM) to 2-PE with tri-phasic in-situ product removal via extraction and XAD4 resins adsorption in 1 pot. Two ml aqueous phase containing 10 g cdw/L of resuspended cells, 50 mM of L-phenylalanine, and 0.5% glucose inside the KP Buffer (100 mM, pH 8) were reacted with 2 ml organic phase. Different type of resins (0.36 g) or MNPs (5 mg/ml) was added for the biotransformation, followed by the reaction for 24 h and subsequent separation of adsorbent, organic phase, and aqueous phase.
Figure 21B:
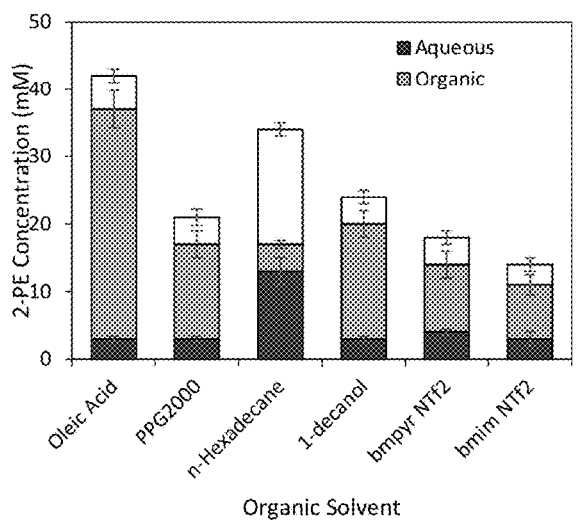

Example 22. Tri-Phasic Cascade Biotransformation of L-Phenylalanine to 2-PE With In-Situ Product Removal (ISPR) via Extraction and Adsorption in 1 Pot XAD4 resin (0.36 g) or OA-MNP-PS (5 mg/ml) was selected as the adsorbent, together with oleic acid, which was proven to give the best extractive biotransformation in the biphasic system (Example 18). Tri-phasic biotransformation was carried out with resting cells E. coli (pRSF-PAL-PAD_pET-SMO-SOI-PAR, 10 g cdw/L) resuspended in KP buffer (100 mM, pH 8.0) containing 0.5% glucose and 50 mM L-phenylalanine with aqueous to organic ratio of 1:1 in a total volume of 4 ml. As shown in FIGS. 21(a) and 21(b), oleic acid gave the highest product conversion among all the other organic solvents tested after 24 h of biotransformation. Addition of XAD4 resin and OA-MNP-PS to the system further enhanced the 2-PE productivity, where 45 mM (=5.5 g/l) and 40 mM (~4.9 g/l) of 2-PE were obtained, respectively. When the initial substrate was increased to 100 mM, 70 mM (~8.6 g/1) and 65 mM (~8 g/l) of 2-PE was produced, respectively, using the same system within a single batch (not shown). These results were 2-fold times higher than the previous biotransformation performed without the addition of adsorbent. The existence of oleic acid was also proven to improve the MNPs-tri-phasic system although the specificity of OA-MNP-PS towards 2-PE was not as high as XAD4.

Figure 21C:
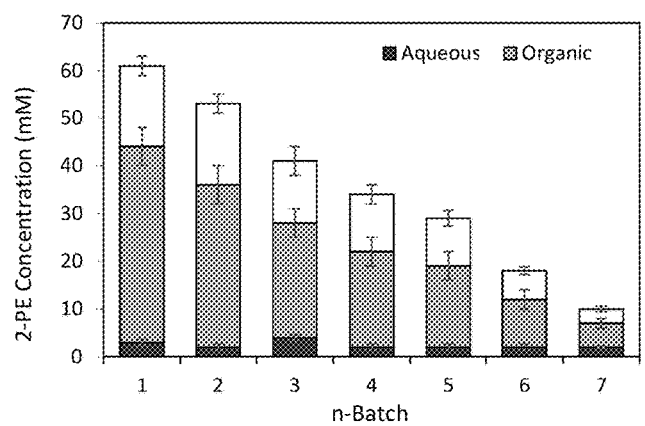
Figure 22:
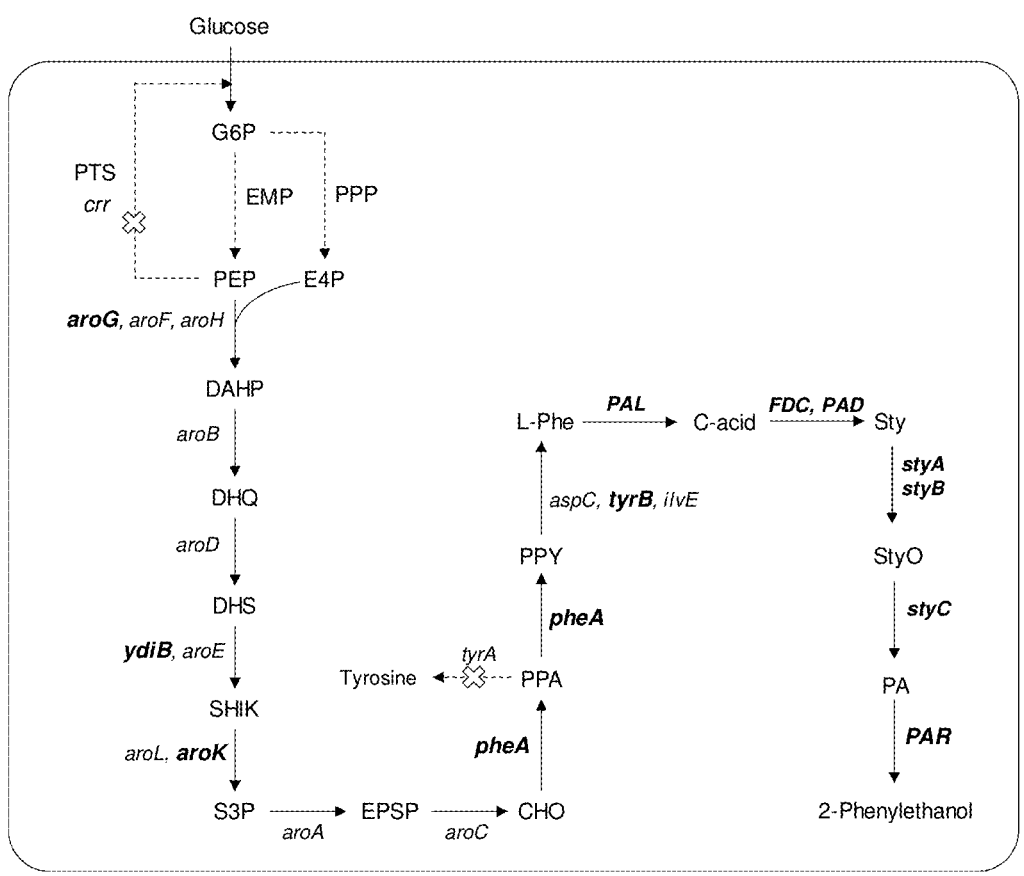
FIG. 22 shows a schematic representation of the approach for 2-phenylethanol production from glucose in *E. coli*. The genes highlighted in bold were overexpressed and the cross-marked pathways were deleted by deleting crr or tyrA. Abbreviations: PTS, phosphotransferase system; EMP, Embden-Meyerhof-Parnas pathway; PPP, pentose phosphate pathway; G6P, glucose-6-phosphate; PEP, phosphoenolpyruvate; E4P, erythrose-4-phosphate; DAHP, 3-deoxy-d-arabino-heptulosonate-7-phosphate; DHQ, 5-dehydroquinate; DHS, 5-dehydro-shikimate; SHIK, shikimate; S3P, shikimate-5-phosphate; EPSP, 3-enolpyruvylshikimate-5-phosphate; CHO, chorismate; PPA, prephenate; PPY, phenylpyruvate; L-Phe, L-phenylalanine; C-acid, trans-cinnamic acid; Sty, styrene; StyO, styrene oxide; PA, phenylacetaldehyde.

In order to perform the repeated batch biotransformation, cells were resuspended in fresh buffer containing 0.5% glucose and same initial substrate concentration, and mixed with a new organic solvent and adsorbent to carry on the biotransformation. As shown in FIG. 21(c), the system could retain up to 83% from its previous batch to produce 2-PE (12 h per-batch). Cumulatively, 250 mM of 2-PE (~31 g/l) was obtained within 7 batches (84 h), marking one of the highest 2-PE production that has been achieved so far.
Microbial Production of 2-PE From Glucose Example 23. Engineering of Native Biosynthetic Pathway for L-Phe Overproduction A scheme for the production of 2-PE from glucose is shown in FIG. 22. The key enzymes for improving L-Phe production were identified as DAHP synthase (AroG), shikimate kinase (AroK), shikimate dehydrogenase (YdiB), chorismate mutase/prephenate dehydratase (PheA) and tyrosine aminotransferase (TyrB). The activities of AroG and PheA were reported to be inhibited in the presence of L-Phe and/or L-tyrosine and feedback inhibition resistant mutants (AroG15 renamed as AroG*, PheA$^{fbr}$ renamed as PheA*) were reported for both enzymes [Liu, S.-P., et al. *Process Biochemistry*. 48(3): 413-419 (2013)]. Also, the expression of all these key enzymes are feedback regulated.

AroG* (SEQ ID NO: 27), aroK, ydiB, pheA* (SEQ ID NO: 28), and tyrB were cloned and overexpressed using strong promoter in T7 strain (T7-Phe).

The genes for overexpression and deletion for overproduction of L-Phe were amplified by PCR from *E. coli* MG1655 genomic DNA. pCDFDuet was used for overexpression of aroG*, aroK, ydiB, pheA* and tyrB genes. The genes aroG*, aroK, ydiB were cloned in multiple cloning site-1 and pheA* and tyrB were cloned in multiple cloning site-2. Two overexpression plasmids were used for the styrene-mediated pathway genes. pRSFDuet was used for the overexpression of PAL, FDC and PAD and pETDuet was used for the overexpression of styABC and PAR, as described in Example 15.

Gene Deletion Methodology:

The crr and tyrA chromosomal deletions were performed using homologous recombination and the pKOV vector invented by Link et al. [Link, A. J., Phillips, D., & Church, G. M. *Journal of bacteriology*, 179(20): 6228-6237 (1997)]. The pKOV plasmid was obtained as a gift from George Church (Addgene plasmid #25769). Briefly, ~600 bp of upstream and downstream DNA base pairs of the target gene were used to provide sufficient homology for gene replacement. The target genes were replaced by random 10-20 bp length double stranded DNA. The crr gene and tyrA gene deletion sequences, comprising the short double stranded DNA flanked by the 600 bp upstream and downstream gene nucleotide sequences are shown in SEQ ID NO: 52 and SEQ ID NO: 53, respectively. The replacement '10-20 bp' length double stranded DNA inserts are at nucleotide positions 619-635 and 598-610, respectively of SEQ ID NO: 52 and 53.

The integration of the recombinant pKOV plasmid into chromosome was performed by growing the *E. coli* T7 strain containing recombinant pKOV plasmid at 42° C. using chloramphenicol as selection marker. After successful replacement of target DNA with insertion fragment, the deletion was confirmed using PCR. Further, the plasmid sequence was removed from the chromosome using sucrose as selection pressure and the deletion was confirmed by PCR and DNA sequencing. Similar approach was performed in single mutants to delete additional gene and create double mutants.

TABLE 6

List of strains and plasmids constructed in Example 23 to Example 26

| Strain/plasmid | Description |
|---|---|
| Strain | |
| T7 | *Escherichia coli* T7 express |
| T7ΔC | T7Δcrr |
| T7ΔT | T7ΔtyrA |
| T7ΔΔ | T7ΔcrrΔtyrA |
| Plasmid | |
| Phe | pCDFDuet-aroG*-aroK-ydiB-pheA*-tyrB |
| Sty | pRSFDuet-PAL-FDC-PAD, pETDuet-styABC-AR |
| pKOV-crr | pKOV plasmid for crr deletion |
| pKOV-tyrA | pKOV plasmid for tyrA deletion |

Figure 23A:
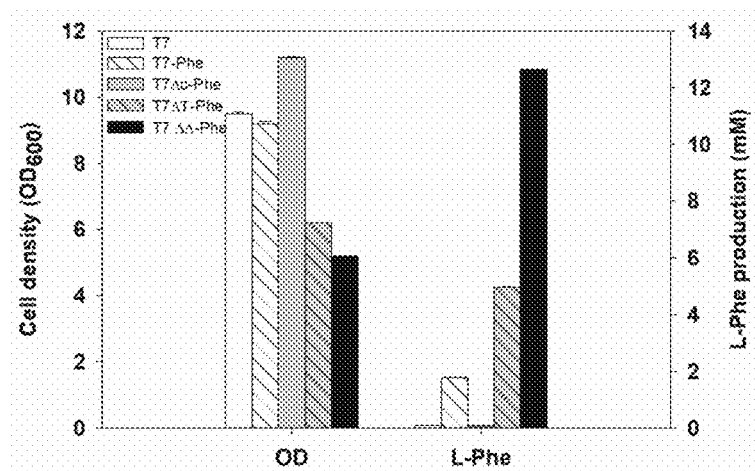
FIGS. 23a and 23b show L-phenylalanine production from glucose by *E. coli* mutants overexpressing L-phenylalanine production pathway. The cell density and L-phenylalanine production of (FIG. 23a) growing cells of all mutants at 24 h and (FIG. 23b) high cell density growing cells of T7-Phe and T7ΔΔ-Phe at 12 h is shown.

Overexpression of the key enzymes resulted in increased L-Phe production by T7-Phe strain (FIG. 23(a)). ~2 mM L-Phe was produced in 24 h whereas T7 strain containing empty plasmid (T7) did not produce any detectable amounts of L-Phe. Also, no significant difference in growth was observed.

To further improve L-Phe production, efforts to improve precursor availability was attempted. One approach was limiting the usage of PEP in PTS system by the deletion of crr. As shown in FIG. 22 (a), deletion of crr significantly improved the cell growth but decreased the L-Phe production. It was believed that decreased glucose uptake rate is the reason for reduced L-Phe production.

Figure 23B:
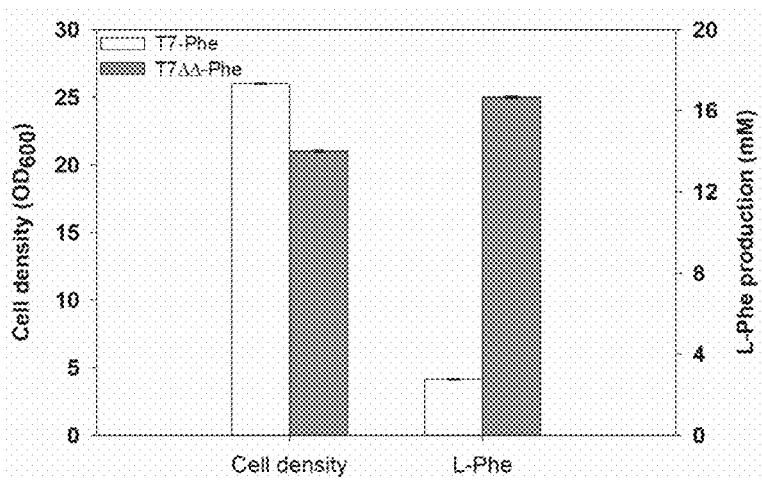

The second target to improve precursor availability was prephenate dehydrogenase (TyrA). TyrA converts prephenate the precursor of L-Phe to tyrosine. Therefore, tyrA was deleted (T7ΔT) and L-Phe production was studied in T7ΔT-Phe. As shown in FIG. 23 (a), there was significant increase in L-Phe production up to 5 mM was observed even with decrease in cell growth.

Surprisingly, the double mutant T7ΔΔ-Phe could produce ~13 mM L-Phe which is ~6-fold higher than T7-Phe (FIG. 23 (a)).

As T7ΔΔ-Phe cell growth was relatively low, a brief experiment was performed by growing T7-Phe and T7ΔΔ-Phe in rich media (LB broth) for 6 h to increase the cell density and shifted to M9 media with a start OD$_{600}$ of ~5 (FIG. 23 (b)). Cell density of 20 OD$_{600}$ could be reached within 12 h in this experiment which is ~4 fold higher than the previous experiment and 16 mM of L-Phe could be obtained within 12 h of fermentation. This promising result also suggests that optimization of media and culture conditions to increase cell growth could improve the L-Phe productivity.

Example 24. Overexpression of Styrene-Mediated 2-PE Production Pathway in L-Phe Producer After the successful overproduction of L-Phe from glucose, the conversion of L-Phe to 2-PE was attempted using the styrene-mediated pathway enzymes (FIG. 22). Recombinant plasmids pRSFDuet-PAL-FDC-PAD and pETDuet-styABC-PAR, prepared according to Example 2, were transformed into the L-Phe producer strain (T7ΔΔ-Phe) and the resultant recombinant strain was named as T7ΔΔ-Phe-Sty.

2-PE production from glucose by T7ΔΔ-Phe-Sty was conducted in a shake flask for 24 h. T7ΔΔ-Phe-Sty could produce 1.3 mM 2-PE directly from glucose and 2.5 mM of unconverted L-Phe was also present at the end of fermentation (FIG. 24).

Example 25. Improvement of 2-PE Production Using In-Situ Product Removal

The low production of 2-PE and L-Phe and accumulation of L-Phe could be also due to the toxicity of 2-PE seen in Example 23. Therefore, 2-PE production from glucose by T7ΔΔ-Phe-Sty in biphasic media with different ratios of M9 media and oleic acid (v:v) such as 1:0.25, 1:0.5 and 1:1 were tested for in-situ 2-PE removal.

Figure 24:
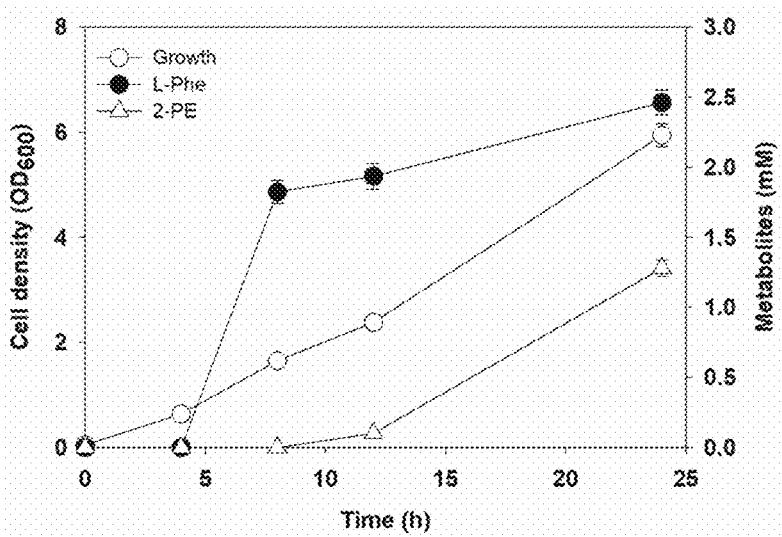
FIG. 24 shows a time course profile of 2-PE production from glucose by T7ΔΔ-Phe-Sty.

As shown in FIG. 24, introduction of biphasic media showed increased growth rate confirming the inhibitory effects of 2-PE during cell growth. All three cultures with biphasic media showed increased growth rate during the exponential phase compared to the control (M9 media only) (FIG. 24 (a)). However, only 1:0.25 showed increased cell density at the end of fermentation, suggesting that oleic acid could also inhibit the cell growth probably due to its surfactant properties or by interfering in oxygen transfer.

Figure 25A:
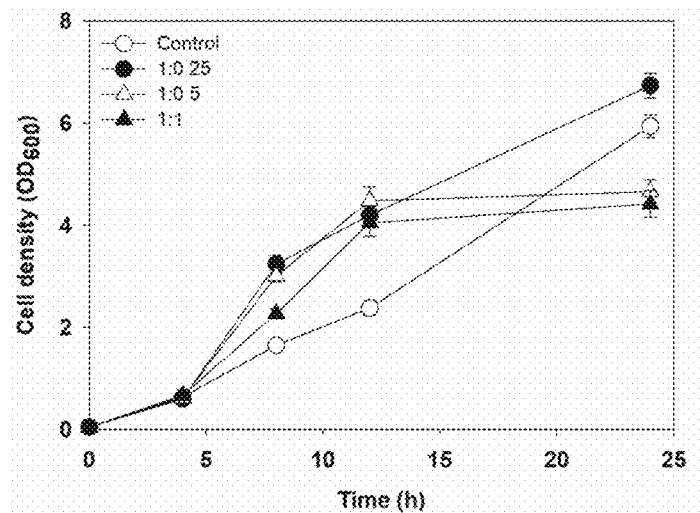
FIGS. 25a and 25b show 2-PE production from glucose in biphasic media by T7ΔΔ-Phe-Sty.
Figure 25B:
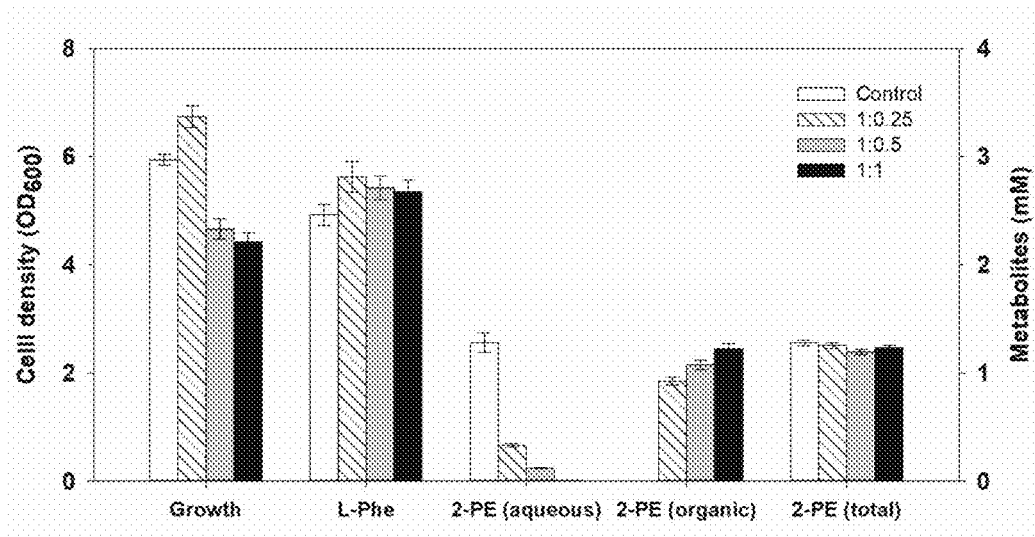

As shown in FIG. 25 (b), metabolites analysis revealed that all four cultures produced similar amounts of L-Phe and 2-PE but the distribution of 2-PE in the aqueous and organic phases were different. The 1:1 culture showed complete extraction of 2-PE from media whereas in 1:0.25 and 1:0.5 cultures there was 0.4 and 0.2 mM 2-PE present in the aqueous phase. This result suggests that a trade-off between cell growth and 2-PE extraction should be considered while choosing the ratio of organic phase in a biphasic system. Addition of small volumes of organic phase at different time points could be a better strategy to remove 2-PE without affecting the cell growth.

Example 26. Evaluation of Engineered Strains for 2-PE Production in Bioreactor Scale To understand the potential of T7ΔΔ-Phe-Sty for 2-PE production from glucose, a bioreactor-scale fermentation with biphasic media was performed. The bioreactor could facilitate a high cell density necessary for reaching higher titers.

A bioreactor-scale fermentation was performed with 1 L of 2×M9 media in a 3 L bioreactor. Glucose was maintained between 50-200 mM by intermittent feeding of 500 g L$^{-1}$ glucose solution. 0.1 mM IPTG was added at 6 h and 100 mL oleic acid was added every 8 h starting from 10 h of fermentation. The growth temperature was shifted to 22° C. from 30° C. after induction.

Figure 26:
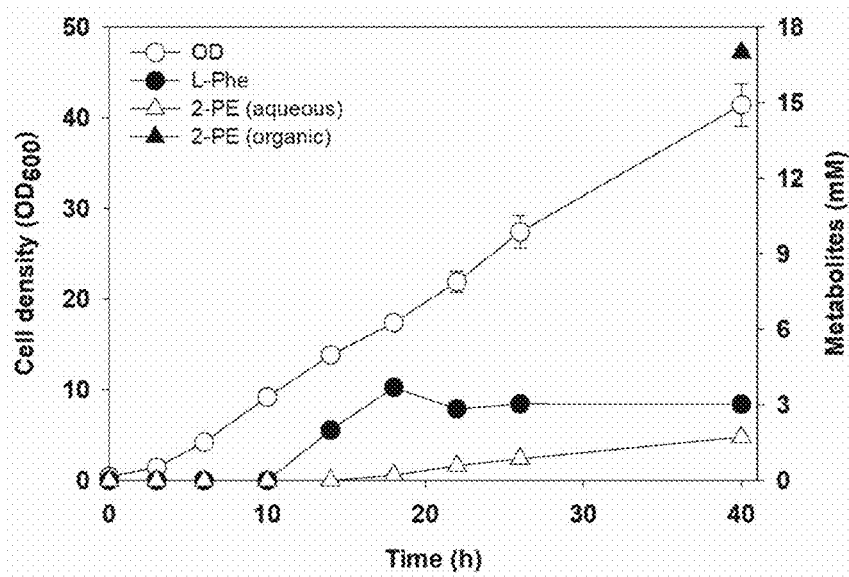
FIG. 26 shows results from a bioreactor scale production of 2-PE from glucose in biphasic media by T7ΔΔ-Phe-Sty. 2-PE concentration in the organic phase was measured only at 40 h.

As shown in FIG. 26, cell growth increased linearly and continued to grow until the end of fermentation probably due to the continuous removal of 2-PE from the media. L-Phe concentration started to increase after induction and maintained at ~3 mM from 18 h whereas 2-PE concentration started to increase from the same time point. The 2-PE concentration in the aqueous and organic phase were 2 and 17 mM, respectively, at 40 h of fermentation. The presence of only 2 mM 2-PE in the aqueous phase shows the efficient in-situ 2-PE removal by oleic acid. A total of 19 mM 2-PE (2.3 g/L) was produced from glucose at the end of 40 h fermentation under non-optimized conditions.

REFERENCES

Any listing or discussion of an apparently prior-published document in this specification should not necessarily be taken as an acknowledgement that such document is part of the state of the art or is common general knowledge.

1. Etschmann, M., Bluemke, W., Sell, D., Schrader, *J. Appl. Microbiol. Biotechnol.* 2002, 59: 1-8.
2. Ferrandez, A., Prieto, M. A., Garcia, J. L., Diaz, E. *FEBS Lett.* 1997, 406: 23.
3. Hua, D., Xu, P. *Biotechnol. Adv.* 2011, 29: 654-660.
4. Kaulmann, U., Smithies, K., Smith, M. E. B., Hailes, H. C., Ward, J. M. *Enzyme Microb. Technol.* 2007, 41: 628-637.
5. Kim, B., Cho, B. R., Hahn, J. S. *Biotechnol. Bioeng.* 2014, 111: 115-124.
6. P. Könst, H. Merkens, S. Kara, S. Kochius, A. Vogel, R. Zuhse, D. Holtmann, I. W. Arends, F. Hollmann, *Angew. Chem. Int. Ed.* 2012, 51: 9914-9917.
7. Hua, D. L, Liang, X. H., Che, C. C., Zhang, X. D., Zhang, J., Li, Y., and Xu, P. *Asian J. Chem.* 2013, 25(11): 5951-5954.
8. Kunjapur, A. M., Tarasova, Y., Prather, K. L. *J. Am. Chem. Soc.* 2014, 136: 11644-11654.
9. Link, A. J., Phillips, D., & Church, G. M. *Journal of bacteriology.* 1997, 179(20): 6228-6237.
10. Liu, S.-P., et al. *Process Biochemistry.* 2013, 48(3): 413-419.
11. Luchini, J. J., Corre, J., and Cremieux, A. *Res. Microbiol.* 1990, 141: 499-510.
12. Mei, J., Min, H., and Lu, Z. *Process Biochemistry.* 2009, 44: 886-890.
13. Seward, R., Willets, J. C., Dinsdale, M. G., and Lloyd, D. *J Inst Brew.* 1996, 102: 439-443.
14. Stark, D., Zala, D., Munch, T., Sonnleitner, B., Marison, I. W., and Stockar, U. V. *Enzyme Microb Technol.* 2003, 32: 212-223.
15. Tieman, D. M., Loucas, H. M., Kim, J. Y., Clark, D. G., Klee, H. J. *Phytochemistry* 2007, 68: 2660
16. Wu, S., Chen, Y., Xu, Y., Li, A., Xu, Q., Glieder, A., Li, Z. *ACS Catal.* 2014, 4: 409-420.
17. Wu, S., Zhou, Y., Wang, T., Too, H. P., Wang, D. I., Li, Z. *Nat. Commun.* 2016, 7: 11917.
18. Zhou, Y., Wu, S., Li, Z. *Angew. Chem. Int. Ed.* 2016, 55: 11647-11650.

The invention claimed is:

1. A method for bioproduction of substituted or unsubstituted phenylacetaldehyde, 2-phenylethanol, phenylacetic acid or phenylethylamine by one or more recombinant bacterial or fungal cells genetically engineered to overexpress, relative to a wild type cell, at least one enzyme, which method comprises subjecting a starting material to a plurality of enzyme-catalyzed chemical transformations in an one-pot reaction system, wherein the starting material is selected from the group consisting of glucose, L-phenylalanine, substituted L-phenylalanine, styrene and substituted styrene, wherein the genetically engineered cells:

i) overexpress styrene monooxygenase and styrene oxide isomerase for generating substituted or unsubstituted phenylacetaldehyde from the styrene or the substituted styrene, wherein the styrene monooxygenase comprises an amino acid sequence having at least 90% identity to the sequence set forth in SEQ ID NOs: 1 and 2; and the styrene oxide isomerase comprises an amino acid sequence having at least 90% identity to the sequence set forth in SEQ ID NO: 3; or ii) overexpress styrene monooxygenase, styrene oxide isomerase and an aldehyde dehydrogenase for generating substituted or unsubstituted phenylacetic acid from the styrene or the substituted styrene, wherein the styrene monooxygenase comprises an amino acid sequence having at least 90% identity to the sequence set forth in SEQ ID NOs: 1 and 2; the styrene oxide isomerase comprises an amino acid sequence having at least 90% identity to the sequence set forth in SEQ ID NO: 3; and the aldehyde dehydrogenase comprises an amino acid sequence having at least 90% identity to the sequence set forth in SEQ ID NO: 4; or iii) overexpress styrene monooxygenase, styrene oxide isomerase, an aldehyde reductase and/or an alcohol dehydrogenase for generating substituted or unsubstituted 2-phenylethanol from the styrene or the substituted styrene, wherein the styrene monooxygenase comprises an amino acid sequence having at least 90% identity to the sequence set forth in SEQ ID NOs: 1 and 2; the styrene oxide isomerase comprises an amino acid sequence having at least 90% identity to the sequence set forth in SEQ ID NO: 3; and the alcohol dehydrogenase comprises an amino acid sequence having at least 90% identity to the sequence set forth in SEQ ID NO: 5; or iv) overexpress styrene monooxygenase, styrene oxide isomerase and a transaminase for generating substituted or unsubstituted phenylethylamine from the styrene or the substituted styrene, wherein the styrene monooxygenase comprises an amino acid sequence having at least 90% identity to the sequence set forth in SEQ ID NOs: 1 and 2; the styrene oxide isomerase comprises an amino acid sequence having at least 90% identity to the sequence set forth in SEQ ID NO: 3; and the transaminase is ω-transaminase comprising an amino acid sequence having at least 90% identity to the sequence set forth in SEQ ID NO: 6.

2. The method of claim 1, wherein the styrene monooxygenase is encoded by a nucleic acid sequence having at least 85% identity to the nucleic acid sequence set forth in SEQ ID NO: 7 and 8; the styrene oxide isomerase is encoded by a nucleic acid sequence having at least 85% identity to the nucleic acid sequence set forth in SEQ ID NO: 9; the aldehyde dehydrogenase is encoded by a nucleic acid sequence having at least 85% identity to the nucleic acid sequence set forth in SEQ ID NO: 10; the alcohol dehydrogenase is encoded by a nucleic acid sequence having at least 85% identity to the nucleic acid sequence set forth in SEQ ID NO: 11 and the transaminase is w-transaminase encoded by a nucleic acid sequence having at least 85% identity to the nucleic acid sequence set forth in SEQ NO: 12.

3. The method of claim 1, wherein the genetically engineered cells produce styrene or substituted styrene from L-phenylalanine or substituted L-phenylalanine by a deamination reaction catalyzed by overexpression of an ammonia lyase and a decarboxylation reaction catalyzed by overexpression of a decarboxylase.

4. The method of claim 3, wherein the ammonia lyase comprises the amino acid sequence set forth in SEQ ID NO: 13 and the decarboxylase comprises the amino acid sequence set forth in SEQ ID NO: 14.

5. The method of claim 1, wherein the genetically engineered cells produce L-phenylalanine from glucose by a reaction catalyzed by overexpression of at least one enzyme selected from a group comprising DAHP synthase (AroG), shikimate kinase (AroK), shikimate dehydrogenase (YdiB), chorismate mutase/prephenate dehydratase (PheA) and tyrosine aminotransferase (TyrB), wherein the genetically engineered cells are engineered to produce L-phenylalanine from glucose.

6. The method of claim 5, wherein AroG comprises the amino acid sequence set forth in SEQ ID NO: 17; AroK comprises the amino acid sequence set forth in SEQ ID NO: 18; YdiB comprises the amino acid sequence set forth in SEQ ID NO: 19; PheA comprises the amino acid sequence set forth in SEQ ID NO: 20, and TyrB comprises the amino acid sequence set forth in SEQ ID NO: 21.

7. The method of claim 5, wherein AroG is replaced by a feedback inhibition resistant mutant AroG* encoded by a nucleic acid comprising the nucleotide sequence of SEQ ID NO: 27 and/or PheA is replaced by a feedback inhibition resistant mutant PheA* encoded by a nucleic acid comprising the nucleotide sequence of SEQ ID NO: 28.

8. The method of claim 5, further comprising deletion or inactivation of crr and/or prephenate dehydrogenase (tyrA) genes.

9. The method of claim 1, wherein the one-pot reaction system comprises the use of a tri-phasic medium comprising:
(a) an aqueous: organic solvent: solid resin medium; or
(b) an aqueous: organic solvent: functionalized nanoparticles medium.

10. A method for bioproduction of substituted or unsubstituted 2-phenylethanol or phenylethylamine by one or more recombinant bacterial or fungal cells genetically engineered to overexpress, relative to a wild type cell, at least one enzyme, which method comprises subjecting a starting material to a plurality of enzyme-catalyzed chemical transformations in an one-pot reaction system, wherein the starting material is styrene or substituted styrene, wherein the genetically engineered cells:

iii) overexpress styrene monooxygenase, styrene oxide isomerase, an aldehyde reductase and/or an alcohol dehydrogenase for generating substituted or unsubstituted 2-phenylethanol from the styrene or the substituted styrene, wherein the styrene monooxygenase comprises an amino acid sequence having at least 90% identity to the sequence set forth in SEQ ID NOs: 1 and 2; the styrene oxide isomerase comprises an amino acid sequence having at least 90% identity to the sequence set forth in SEQ ID NO: 3; and the alcohol dehydrogenase comprises an amino acid sequence having at least 90% identity to the sequence set forth in SEQ ID NO: 5; or iv) overexpress styrene monooxygenase, styrene oxide isomerase and a transaminase for generating substituted or unsubstituted phenylethylamine from the styrene or the substituted styrene, wherein the styrene monooxygenase comprises an amino acid sequence having at least 90% identity to the sequence set forth in SEQ ID NOs: 1 and 2; the styrene oxide isomerase comprises an amino acid sequence having at least 90% identity to the sequence set forth in SEQ ID NO: 3; and the transaminase is ω-transaminase comprising an amino acid sequence having at least 90% identity to the sequence set forth in SEQ ID NO: 6.

* * * * *

SEQUENCE LISTING

```
<160> NUMBER OF SEQ ID NOS: 53

<210> SEQ ID NO 1
<211> LENGTH: 415
<212> TYPE: PRT
<213> ORGANISM: pseudomonas sp. VLB120
<220> FEATURE:
<221> NAME/KEY: MISC_FEATURE
<223> OTHER INFORMATION: Amino acid sequence for styrene monooxygenase,
      StyA part

<400> SEQUENCE: 1
```

```
Met Lys Lys Arg Ile Gly Ile Val Gly Ala Gly Thr Ala Gly Leu His
1               5                   10                  15

Leu Gly Leu Phe Leu Arg Gln His Asp Val Asp Val Thr Val Tyr Thr
                20                  25                  30

Asp Arg Lys Pro Asp Glu Tyr Ser Gly Leu Arg Leu Leu Asn Thr Val
            35                  40                  45

Ala His Asn Ala Val Thr Val Gln Arg Glu Val Ala Leu Asp Val Asn
        50                  55                  60

Glu Trp Pro Ser Glu Glu Phe Gly Tyr Phe Gly His Tyr Tyr Tyr Val
65                      70                  75                  80

Gly Gly Pro Gln Pro Met Arg Phe Tyr Gly Asp Leu Lys Ala Pro Ser
                    85                  90                  95

Arg Ala Val Asp Tyr Arg Leu Tyr Gln Pro Met Leu Met Arg Ala Leu
                100                 105                 110

Glu Ala Arg Gly Gly Lys Phe Cys Tyr Asp Ala Val Ser Ala Glu Asp
            115                 120                 125

Leu Glu Gly Leu Ser Glu Gln Tyr Asp Leu Leu Val Val Cys Thr Gly
            130                 135                 140

Lys Tyr Ala Leu Gly Lys Val Phe Glu Lys Gln Ser Glu Asn Ser Pro
145                 150                 155                 160

Phe Glu Lys Pro Gln Arg Ala Leu Cys Val Gly Leu Phe Lys Gly Ile
                165                 170                 175

Lys Glu Ala Pro Ile Arg Ala Val Thr Met Ser Phe Ser Pro Gly His
                180                 185                 190

Gly Glu Leu Ile Glu Ile Pro Thr Leu Ser Phe Asn Gly Met Ser Thr
            195                 200                 205

Ala Leu Val Leu Glu Asn His Ile Gly Ser Asp Leu Glu Val Leu Ala
        210                 215                 220

His Thr Lys Tyr Asp Asp Pro Arg Ala Phe Leu Asp Leu Met Leu
225                 230                 235                 240

Glu Lys Leu Gly Lys His His Pro Ser Val Ala Glu Arg Ile Asp Pro
            245                 250                 255

Ala Glu Phe Asp Leu Ala Asn Ser Ser Leu Asp Ile Leu Gln Gly Gly
                260                 265                 270

Val Val Pro Ala Phe Arg Asp Gly His Ala Thr Leu Asn Asn Gly Lys
                275                 280                 285

Thr Ile Ile Gly Leu Gly Asp Ile Gln Ala Thr Val Asp Pro Val Leu
290                 295                 300

Gly Gln Gly Ala Asn Met Ala Ser Tyr Ala Ala Trp Ile Leu Gly Glu
305                 310                 315                 320

Glu Ile Leu Ala His Ser Val Tyr Asp Leu Arg Phe Ser Glu His Leu
                325                 330                 335

Glu Arg Arg Arg Gln Asp Arg Val Leu Cys Ala Thr Arg Trp Thr Asn
            340                 345                 350

Phe Thr Leu Ser Ala Leu Ser Ala Leu Pro Pro Glu Phe Leu Ala Phe
        355                 360                 365

Leu Gln Ile Leu Ser Gln Ser Arg Glu Met Ala Asp Glu Phe Thr Asp
        370                 375                 380

Asn Phe Asn Tyr Pro Glu Arg Gln Trp Asp Arg Phe Ser Ser Pro Glu
385                 390                 395                 400

Arg Ile Gly Gln Trp Cys Ser Gln Phe Ala Pro Thr Ile Ala Ala
                405                 410                 415
```

<210> SEQ ID NO 2
<211> LENGTH: 170
<212> TYPE: PRT
<213> ORGANISM: pseudomonas sp. VLB120
<220> FEATURE:
<221> NAME/KEY: MISC_FEATURE
<223> OTHER INFORMATION: Amino acid sequence for styrene monooxygenase,
      StyB part

<400> SEQUENCE: 2

Met Thr Leu Lys Lys Asp Met Ala Val Asp Ile Asp Ser Thr Asn Phe
1               5                   10                  15

Arg Gln Ala Val Ala Leu Phe Ala Thr Gly Ile Ala Val Leu Ser Ala
            20                  25                  30

Glu Thr Glu Glu Gly Asp Val His Gly Met Thr Val Asn Ser Phe Thr
        35                  40                  45

Ser Ile Ser Leu Asp Pro Pro Thr Val Met Val Ser Leu Lys Ser Gly
    50                  55                  60

Arg Met His Glu Leu Leu Thr Gln Gly Gly Arg Phe Gly Val Ser Leu
65                  70                  75                  80

Leu Gly Glu Ser Gln Lys Val Phe Ser Ala Phe Ser Lys Arg Ala
                85                  90                  95

Met Asp Asp Thr Pro Pro Ala Phe Thr Ile Gln Ala Gly Leu Pro
            100                 105                 110

Thr Leu Gln Gly Ala Met Ala Trp Phe Glu Cys Glu Val Glu Ser Thr
        115                 120                 125

Val Gln Val His Asp His Thr Leu Phe Ile Ala Arg Val Ser Ala Cys
130                 135                 140

Gly Thr Pro Glu Ala Asn Thr Pro Gln Pro Leu Leu Phe Phe Ala Ser
145                 150                 155                 160

Arg Tyr His Gly Asn Pro Leu Pro Leu Asn
                165                 170

<210> SEQ ID NO 3
<211> LENGTH: 169
<212> TYPE: PRT
<213> ORGANISM: pseudomonas sp. VLB120
<220> FEATURE:
<221> NAME/KEY: MISC_FEATURE
<223> OTHER INFORMATION: Amino acid sequence for styrene oxide
      isomerase, SOI

<400> SEQUENCE: 3

Met Leu His Ala Phe Glu Arg Lys Met Ala Gly His Gly Ile Leu Met
1               5                   10                  15

Ile Phe Cys Thr Leu Leu Phe Gly Val Gly Leu Trp Met Asn Leu Val
            20                  25                  30

Gly Gly Phe Glu Ile Ile Pro Gly Tyr Ile Ile Glu Phe His Val Pro
        35                  40                  45

Gly Ser Pro Glu Gly Trp Ala Arg Ala His Ser Gly Pro Ala Leu Asn
    50                  55                  60

Gly Met Met Val Ile Ala Val Ala Phe Val Leu Pro Ser Leu Gly Phe
65                  70                  75                  80

Ala Asp Lys Thr Ala Arg Leu Leu Gly Ser Ile Ile Val Leu Asp Gly
                85                  90                  95

Trp Ser Asn Val Gly Phe Tyr Leu Phe Ser Asn Phe Ser Pro Asn Arg
            100                 105                 110

Gly Leu Thr Phe Gly Pro Asn Gln Phe Gly Pro Gly Asp Ile Phe Ser

```
                    115                 120                 125
Phe Leu Ala Leu Ala Pro Ala Tyr Leu Phe Gly Val Leu Ala Met Gly
                130                 135                 140

Ala Leu Ala Val Ile Gly Tyr Gln Ala Leu Lys Ser Thr Arg Ser Arg
145                 150                 155                 160

Lys Ala Val Pro His Ala Ala Glu
                165

<210> SEQ ID NO 4
<211> LENGTH: 499
<212> TYPE: PRT
<213> ORGANISM: Escherichia coli
<220> FEATURE:
<221> NAME/KEY: MISC_FEATURE
<223> OTHER INFORMATION: Amino acid sequence for aldehyde dehydrogenase,
      EcALDH

<400> SEQUENCE: 4

Met Thr Glu Pro His Val Ala Val Leu Ser Gln Val Gln Gln Phe Leu
1               5                   10                  15

Asp Arg Gln His Gly Leu Tyr Ile Asp Gly Arg Pro Gly Pro Ala Gln
                20                  25                  30

Ser Glu Lys Arg Leu Ala Ile Phe Asp Pro Ala Thr Gly Gln Glu Ile
            35                  40                  45

Ala Ser Thr Ala Asp Ala Asn Glu Ala Asp Val Asp Asn Ala Val Met
50                  55                  60

Ser Ala Trp Arg Ala Phe Val Ser Arg Arg Trp Ala Gly Arg Leu Pro
65                  70                  75                  80

Ala Glu Arg Glu Arg Ile Leu Leu Arg Phe Ala Asp Leu Val Glu Gln
                85                  90                  95

His Ser Glu Glu Leu Ala Gln Leu Glu Pro Leu Glu Gln Gly Lys Ser
                100                 105                 110

Ile Ala Ile Ser Arg Ala Phe Glu Val Gly Cys Thr Leu Asn Trp Met
            115                 120                 125

Arg Tyr Thr Ala Gly Leu Thr Thr Lys Ile Ala Gly Lys Thr Leu Asp
130                 135                 140

Leu Ser Ile Pro Leu Pro Gln Gly Ala Arg Tyr Gln Ala Trp Thr Arg
145                 150                 155                 160

Lys Glu Pro Val Gly Val Val Ala Gly Ile Val Pro Trp Asn Phe Pro
                165                 170                 175

Leu Met Ile Gly Met Trp Lys Val Met Pro Ala Leu Ala Ala Gly Cys
                180                 185                 190

Ser Ile Val Ile Lys Pro Ser Glu Thr Thr Pro Leu Thr Met Leu Arg
            195                 200                 205

Val Ala Glu Leu Ala Ser Glu Ala Gly Ile Pro Asp Gly Val Phe Asn
210                 215                 220

Val Val Thr Gly Ser Gly Ala Val Cys Gly Ala Ala Leu Thr Ser His
225                 230                 235                 240

Pro His Val Ala Lys Ile Ser Phe Thr Gly Ser Thr Ala Thr Gly Lys
                245                 250                 255

Gly Ile Ala Arg Thr Ala Ala Asp Arg Leu Thr Arg Val Thr Leu Glu
                260                 265                 270

Leu Gly Gly Lys Asn Pro Ala Ile Val Leu Lys Asp Ala Asp Pro Gln
            275                 280                 285

Trp Val Ile Glu Gly Leu Met Thr Gly Ser Phe Leu Asn Gln Gly Gln
290                 295                 300
```

Val Cys Ala Ala Ser Ser Arg Ile Tyr Ile Glu Ala Pro Leu Phe Asp
305                 310                 315                 320

Thr Leu Val Ser Gly Phe Glu Gln Ala Val Lys Ser Leu Gln Val Gly
            325                 330                 335

Pro Gly Met Ser Pro Val Ala Gln Ile Asn Pro Leu Val Ser Arg Ala
        340                 345                 350

His Cys Gly Lys Val Cys Ser Phe Leu Asp Asp Ala Gln Ala Gln Gln
        355                 360                 365

Ala Glu Leu Ile Arg Gly Ser Asn Gly Pro Ala Gly Glu Gly Tyr Tyr
        370                 375                 380

Val Ala Pro Thr Leu Val Val Asn Pro Asp Ala Lys Leu Arg Leu Thr
385                 390                 395                 400

Arg Glu Glu Val Phe Gly Pro Val Val Asn Leu Val Arg Val Ala Asp
                405                 410                 415

Gly Glu Glu Ala Leu Gln Leu Ala Asn Asp Thr Glu Tyr Gly Leu Thr
            420                 425                 430

Ala Ser Val Trp Thr Gln Asn Leu Ser Gln Ala Leu Glu Tyr Ser Asp
        435                 440                 445

Arg Leu Gln Ala Gly Thr Val Trp Val Asn Ser His Thr Leu Ile Asp
450                 455                 460

Ala Asn Leu Pro Phe Gly Gly Met Lys Gln Ser Gly Thr Gly Arg Asp
465                 470                 475                 480

Phe Gly Pro Asp Trp Leu Asp Gly Trp Cys Glu Thr Lys Ser Val Cys
                485                 490                 495

Val Arg Tyr

<210> SEQ ID NO 5
<211> LENGTH: 328
<212> TYPE: PRT
<213> ORGANISM: Saccharomyces cerevisiae
<220> FEATURE:
<221> NAME/KEY: MISC_FEATURE
<223> OTHER INFORMATION: Amino acid sequence for alcohol dehydrogenase

<400> SEQUENCE: 5

Met Ser Val Thr Ala Lys Thr Val Cys Val Thr Gly Ala Ser Gly Tyr
1               5                   10                  15

Ile Ala Ser Trp Leu Val Lys Phe Leu Leu His Ser Gly Tyr Asn Val
            20                  25                  30

Lys Ala Ser Val Arg Asp Pro Asn Asp Pro Lys Lys Thr Gln His Leu
        35                  40                  45

Leu Ser Leu Gly Gly Ala Lys Glu Arg Leu His Leu Phe Lys Ala Asn
    50                  55                  60

Leu Leu Glu Glu Gly Ser Phe Asp Ala Val Val Asp Gly Cys Glu Gly
65                  70                  75                  80

Val Phe His Thr Ala Ser Pro Phe Tyr Tyr Ser Val Thr Asp Pro Gln
                85                  90                  95

Ala Glu Leu Leu Asp Pro Ala Val Lys Gly Thr Leu Asn Leu Leu Gly
            100                 105                 110

Ser Cys Ala Lys Ala Pro Ser Val Lys Arg Val Val Leu Thr Ser Ser
        115                 120                 125

Ile Ala Ala Val Ala Tyr Ser Gly Gln Pro Arg Thr Pro Glu Val Val
    130                 135                 140

Val Asp Glu Ser Trp Trp Thr Ser Pro Asp Tyr Cys Lys Glu Lys Gln
145                 150                 155                 160

```
Leu Trp Tyr Val Leu Ser Lys Thr Leu Ala Glu Asp Ala Ala Trp Lys
                165                 170                 175

Phe Val Lys Glu Lys Gly Ile Asp Met Val Val Asn Pro Ala Met
            180                 185                 190

Val Ile Gly Pro Leu Leu Gln Pro Thr Leu Asn Thr Ser Ser Ala Ala
            195                 200                 205

Val Leu Ser Leu Val Asn Gly Ala Glu Thr Tyr Pro Asn Ser Ser Phe
    210                 215                 220

Gly Trp Val Asn Val Lys Asp Val Ala Asn Ala His Ile Leu Ala Phe
225                 230                 235                 240

Glu Asn Pro Ser Ala Asn Gly Arg Tyr Leu Met Val Glu Arg Val Ala
                245                 250                 255

His Tyr Ser Asp Ile Leu Lys Ile Leu Arg Asp Leu Tyr Pro Thr Met
                260                 265                 270

Gln Leu Pro Glu Lys Cys Ala Asp Asp Asn Pro Leu Met Gln Asn Tyr
            275                 280                 285

Gln Val Ser Lys Glu Lys Ala Lys Ser Leu Gly Ile Glu Phe Thr Thr
    290                 295                 300

Leu Glu Glu Ser Ile Lys Glu Thr Val Glu Ser Leu Lys Glu Lys Lys
305                 310                 315                 320

Phe Phe Gly Gly Ser Ser Ser Met
                325
```

<210> SEQ ID NO 6
<211> LENGTH: 459
<212> TYPE: PRT
<213> ORGANISM: Chromobacterium violaceum
<220> FEATURE:
<221> NAME/KEY: MISC_FEATURE
<223> OTHER INFORMATION: Amino acid sequence for w-transaminase, CvTA

<400> SEQUENCE: 6

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
```

```
                180             185                 190
Lys Asp Met Thr Pro Asp Glu Phe Gly Val Ala Ala Arg Trp Leu
            195                 200                 205
Glu Glu Lys Ile Leu Glu Ile Gly Ala Asp Lys Val Ala Phe Val
            210                 215                 220
Gly Glu Pro Ile Gln Gly Ala Gly Val Ile Val Pro Pro Ala Thr
225                 230                 235                 240
Tyr Trp Pro Glu Ile Glu Arg Ile Cys Arg Lys Tyr Asp Val Leu Leu
                245                 250                 255
Val Ala Asp Glu Val Ile Cys Gly Phe Gly Arg Thr Gly Glu Trp Phe
                260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Lys
            290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Ile
            340                 345                 350
Gly Pro Tyr Met Gln Lys Arg Trp Arg Glu Thr Phe Ser Arg Phe Glu
            355                 360                 365
His Val Asp Asp Val Arg Gly Val Gly Met Val Gln Ala Phe Thr Leu
            370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
                405                 410                 415
Ala Cys Gly Asp His Ile Val Ser Ala Pro Pro Leu Val Met Thr Arg
            420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
    450                 455

<210> SEQ ID NO 7
<211> LENGTH: 1284
<212> TYPE: DNA
<213> ORGANISM: pseudomonas sp. VLB120
<220> FEATURE:
<221> NAME/KEY: misc_feature
<223> OTHER INFORMATION: DNA sequence for styrene monooxygenase, StyA
      part

<400> SEQUENCE: 7
atgaaaaagc gtatcggtat tgttggtgca ggcactgccg cctccatct tggtctcttc      60 cttcgtcagc atgacgtcga cgtcactgtg tacactgatc gtaagcccga tgagtacagc    120
ggactgcgtc tcctgaatac cgttgctcac aacgcggtga cggtgcagcg ggaggttgcc    180
ctcgacgtca atgagtggcc gtctgaggag tttggttatt cggccacta ctactacgta    240 ggtgggccgc agcccatgcg tttctacggt gatctcaagg ctcccagccg tgcagtggac    300
taccgtctct accagccgat gctgatgcgt gcactggaag ccaggggcgg caagttctgc    360
tacgacgcgg tgtctgccga agatctggaa gggctgtcgg agcagtacga tctgctggtt    420
```

```
gtgtgcactg gtaaatacgc cctcggcaag gtgttcgaga agcagtccga aaactcgccc    480
ttcgagaagc cgcaacgggc actgtgcgtt ggtctcttca agggcatcaa ggaagcaccg    540
attcgcgcgg tgactatgtc cttctcgcca gggcatggcg agctgattga gattccaacc    600
ctgtcgttca atggcatgag cacagcgctg gtgctcgaaa accatattgg tagcgatctg    660
gaagttctcg cccacaccaa gtatgacgat gacccgcgtg cgttcctcga tctgatgctg    720
gagaagctgg gtaagcatca tccttccgtt gccgagcgca tcgatccggc tgagttcgac    780
cttgccaaca gttctctgga catcctccag ggtggtgttg tgccggcatt ccgcgacggt    840
catgcgaccc tcaataacgg caaaaccatc attgggctgg cgacatccga gcaactgtc    900 gatccggtct tgggccaggg cgcgaacatg gcgtcctatg cggcatggat ctgggcgag    960 gaaatccttg cgcactctgt ctacgacctg cgcttcagcg aacacctgga gcgtcgccgc    1020
caggatcgcg tgctgtgtgc cacgcgatgg accaacttca ctctgagcgc tctctcggca    1080
cttccgccgg agttcctcgc cttccttcag atcctgagcc agagccgtga aatggctgat    1140
gagttcacgg acaacttcaa ctacccggaa cgtcagtggg atcgcttctc cagcccggaa    1200
cgtatcggac agtggtgcag tcagttcgca cccactatcg cggcctgatg gtgcagtcag    1260
ttcgcaccca ctatcgcggc ctga                                           1284

<210> SEQ ID NO 8
<211> LENGTH: 513
<212> TYPE: DNA
<213> ORGANISM: pseudomonas sp. VLB120
<220> FEATURE:
<221> NAME/KEY: misc_feature
<223> OTHER INFORMATION: DNA sequence for styrene monooxygenase, StyB
      part

<400> SEQUENCE: 8
atgacgttaa aaaaagatat ggcggtggat atcgactcca ccaacttccg ccaggcggtt     60
gcattgttcg cgacgggaat tgcggttctc agcgcggaga ctgaagaggg cgatgtgcac    120
ggcatgaccg tgaacagttt cacctccatc agtctggatc cgccgactgt gatggtttcc    180
ctgaaatcgg gccgtatgca tgagttgctg actcaaggcg gacgcttcgg agttagcctc    240
ttgggtgaaa gccagaaggt gttctcggca ttcttcagca gcgcgcgat ggatgacacg    300 cctccccccg ccttcaccat tcaggccggc cttcccactc tgcagggcgc catggcctgg    360
ttcgaatgcg aggtggagag cacggttcaa gtacacgacc acacgctctt cattgcgcgc    420
gttagcgcct gtggaacgcc tgaggcgaat acccccagc cgctgctgtt ctttgccagc    480
cgttatcacg gcaacccgtt gccactgaat tga                                 513

<210> SEQ ID NO 9
<211> LENGTH: 510
<212> TYPE: DNA
<213> ORGANISM: pseudomonas sp. VLB120
<220> FEATURE:
<221> NAME/KEY: misc_feature
<223> OTHER INFORMATION: DNA sequence for styrene oxide isomerase, SOI

<400> SEQUENCE: 9
atgttacacg cgtttgaacg taaaatggca gggcatggaa ttctgatgat tttttgtaca     60
ctgttgtttg gagtcggcct gtggatgaac cttgtgggcg ggttcgaaat catccccggt    120
tacattatcg aattccatgt tccggggagt cccgaaggtt gggcacgtgc tcatagcggc    180
ccggcactga acggcatgat ggtcattgcc gtcgcgttcg ttctgccatc cctgggcttc    240
```

```
gcagacaaaa ccgcacgtct gctgggttcg atcattgttc tggatggctg gtccaatgtg    300
gggttctacc tgtttagcaa cttttcgcct aaccgtggcc tgacctttgg cccgaaccag    360
tttggaccgg gtgatatttt ctcatttctg ctctcgccc cggcgtacct gttcggcgtg     420
ctggctatgg gcgccctcgc ggtgatcggt tatcaggcgt tgaaatctac ccgcagccgt    480
aaagccgttc cacacgcggc agccgagtaa                                     510
```

```
<210> SEQ ID NO 10
<211> LENGTH: 1500
<212> TYPE: DNA
<213> ORGANISM: Escherichia coli
<220> FEATURE:
<221> NAME/KEY: misc_feature
<223> OTHER INFORMATION: DNA sequence for aldehyde dehydrogenase, EcALDH

<400> SEQUENCE: 10
```

```
atgacagagc cgcatgtagc agtattaagc caggtccaac agtttctcga tcgtcaacac    60
ggtctttata ttgatggtcg tcctggcccc gcacaaagtg aaaaacggtt ggcgatcttt   120
gatccggcca ccgggcaaga aattgcgtct actgctgatg ccaacgaagc ggatgtagat   180
aacgcagtca tgtctgcctg gcgggccttt gtctcgcgtc gctgggccgg gcgattaccc   240
gcagagcgtg aacgtattct gctacgtttt gctgatctgg tggagcagca cagtgaggag   300
ctggcgcaac tggaaaccct ggagcaaggc aagtcaattg ccatttcccg tgcttttgaa   360
gtgggctgta cgctgaactg gatgcgttat accgccgggt aacgaccaa aatcgcgggt    420 aaaacgctgg acttgtcgat tcccttaccc caggggcgc gttatcaggc ctggacgcgt    480
aaagagccgg ttggcgtagt ggcgggaatt gtgccatgga actttccgtt gatgattggt    540
atgtggaagg tgatgccagc actggcagca ggctgttcaa tcgtgattaa gccttcggaa    600
accacgccac tgacgatgtt gcgcgtggcg gaactggcca gcgaggctgg tatccctgat    660
ggcgttttta atgtcgtcac cgggtcaggt gctgtatgcg gcgcggccct gacgtcacat    720
cctcatgttg cgaaaatcag ttttaccggt tcaaccgcga cgggaaaagg tattgccaga    780
actgctgctg atcacttaac gcgtgtaacg ctggaactgg gcggtaaaaa cccggcaatt    840
gtattaaaag atgctgatcc gcaatgggtt attgaaggct tgatgaccgg aagcttcctg    900
aatcaagggc aagtatgcgc cgccagttcg cgaatttata ttgaagcgcc gttgtttgac    960
acgctggtta gtggatttga gcaggcggta aaatcgttgc aagtgggacc ggggatgtca   1020
cctgttgcac agattaaccc tttggtttct cgtgcgcact gcgacaaagt gtgttcattc   1080
ctcgacgatg cgcaggcaca gcaagcagag ctgattcgcg gtcgaatgg accagccgga   1140 gaggggtatt atgttgcgcc aacgctggtg gtaaatcccg atgctaaatt gcgcttaact   1200
cgtgaagagg tgtttggtcc ggtggtaaac ctggtgcgag tagcggatgg agaagaggcg   1260
ttacaactgg caaacgacac ggaatatggc ttaactgcca gtgtctggac gcaaaatctc   1320
tcccaggctc tggaatatag cgatcgctta caggcaggga cggtgtgggt aaacagccat   1380
accttaattg acgctaactt accgtttggt gggatgaagc agtcaggaac gggccgtgat   1440
tttggccccg actggctgga cggttggtgt gaaactaagt cggtgtgtgt acggtattaa   1500
```

```
<210> SEQ ID NO 11
<211> LENGTH: 987
<212> TYPE: DNA
<213> ORGANISM: Saccharomyces cerevisiae
<220> FEATURE:
<221> NAME/KEY: misc_feature
<223> OTHER INFORMATION: DNA sequence for alcohol dehydrogenase
```

<400> SEQUENCE: 11

```
atgagcgtga ccgcgaaaac cgtgtgtgtt accggcgcca gcggctacat cgcctcttgg     60
cttgtaaagt ttctgttgca ctcgggttat aacgttaaag cgtcagtccg cgatccgaac    120
gacccgaaaa aaacgcagca cctgctgtct ctgggcggcg cgaaagaacg gctgcacctg    180
ttcaaagcga atctgctgga agaaggttcg ttcgatgcgg ttgttgacgg ttgcgaaggt    240
gtgttccata ccgcgtcccc tttctactat tctgtaaccg atccgcaggc cgagcttctg    300
gatccggcag taaaaggcac tctgaacctg ctcggttcct gtgctaaagc gccttcagtt    360
aagcgtgtag tgctcaccag cagcatcgct gccgttgcgt actctggtca ccacgtact     420
cctgaagtag tagtggatga atcgtggtgg acgtctcctg attattgtaa agaaaaacag    480
ctgtggtacg tcttaagtaa aacgctggcg gaagatgcgg cttggaaatt tgtgaaagaa    540
aaggggattg acatggtcgt tgtaaatcct gcaatggtca ttggaccgtt actgcagcca    600
accctcaata cgagcagcgc cgcggtgctg tctcttgtaa acggggcgga acatatcct    660
aatagctctt tcggctgggt taatgtcaaa gatgtggcga atgcccacat tcttgccttt    720
gaaaacccaa gcgccaacgg ccgttacttg atggttgaac gtgttgcgca ctatagcgac    780
atcctgaaaa tcctccgcga cctgtaccct actatgcaat gcctgaaaa atgtgcagat    840
gataacccgc tgatgcagaa ttaccaggtc tcaaaagaaa aagcgaaatc actgggcatc    900
gaatttacta ctcttgagga aagtattaaa gaaacagtag aatccttgaa agaaaaaaaa    960
tttttcggcg ggagttcaag catgtga                                         987
```

<210> SEQ ID NO 12
<211> LENGTH: 1380
<212> TYPE: DNA
<213> ORGANISM: Chromobacterium violaceum
<220> FEATURE:
<221> NAME/KEY: misc_feature
<223> OTHER INFORMATION: DNA sequence for w-transaminase, CvTA

<400> SEQUENCE: 12

```
atgcaaaaac aacgcaccac ctcacaatgg cgcgaactgg atgccgcaca ccacctgcac    60
ccgtttaccg acaccgcaag cctgaatcag gccggcgccc gtgttatgac ccgcggcgaa    120
ggtgtgtatc tgtgggattc tgagggtaac aaaattatcg acggcatggc tggtctgtgg    180
tgcgttaatg tcggctatgg tcgtaaagat tttgccgaag cggcccgtcg ccaaatggaa    240
gaactgccgt tctacaacac cttttttcaaa accacgcatc cggcggtggt tgaactgagc    300
agcctgctgg cggaagttac gccggccggc tttgatcgtg tgttctatac caattcaggt    360
tcggaaagcg tggatacgat gatccgcatg gttcgtcgct actgggacgt ccagggcaaa    420
ccggaaaaga aaaccctgat cggtcgttgg aacggctatc atggttctac gattggcggt    480
gcaagtctgg gcggtatgaa atacatgcac gaacagggcg atctgccgat tccgggtatg    540
gcgcatatcg aacaaccgtg gtggtacaaa cacggcaaag atatgacccc ggacgaattt    600
ggtgtcgtgg cagctcgctg gctggaagaa aaaattctgg aaatcggcgc cgataaagtg    660
gcggcctttg ttggcgaacc gattcagggt gcgggcggtg tgattgttcc gccggccacc    720
tattggccgg aaattgaacg tatctgccgc aaatacgatg ttctgctggt cgcagacgaa    780
gttatttgtg gctttggtcg taccggcgaa tggttcggtc atcagcactt tggcttccaa    840
ccggaccgtg ttacggcagc taaaggcctg agttccggtt atctgccgat cggcgccgtc    900
ttcgtgggta acgcgttgc agaaggtctg attgctggcg gtgattttaa tcatggcttc    960
```

```
acctatagcg gtcacccggt ctgtgcggcc gtggcacatg ctaatgtggc agctctgcgt    1020
gacgaaggca tcgtgcagcg cgttaaagat gacattggtc cgtatatgca aaaacgttgg    1080
cgcgaaacgt ttagccgttt cgaacacgtc gatgacgtgc gcggcgttgg tatggtccag    1140
gcatttaccc tggtgaaaaa taaagctaaa cgcgaactgt ttccggattt cggcgaaatt    1200
ggtacgctgt gccgtgacat cttttttccgc aacaatctga ttatgcgtgc gtgtggtgat    1260
cacattgtta gcgccccgcc gctggttatg acccgcgcag aagtcgacga atgctggcc     1320 gtggcggaac gctgcctgga agaatttgaa cagaccctga agctcgtgg cctggcgtaa     1380
```

<210> SEQ ID NO 13
<211> LENGTH: 717
<212> TYPE: PRT
<213> ORGANISM: Arabidopsis thaliana
<220> FEATURE:
<221> NAME/KEY: MISC_FEATURE
<223> OTHER INFORMATION: Amino acid sequence for phenylalanine ammonia
      lyase, AtPAL

<400> SEQUENCE: 13

```
Met Asp Gln Ile Glu Ala Met Leu Cys Gly Gly Gly Glu Lys Thr Lys
1               5                   10                  15

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
        115                 120                 125

Leu Gln Thr Glu Leu Ile Arg Phe Leu Asn Ala Gly Ile Phe Gly Asn
    130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly His Leu Val
        195                 200                 205

Pro Leu Ser Tyr Ile Ala Gly Leu Leu Thr Gly Arg Pro Asn Ser Lys
    210                 215                 220

Ala Thr Gly Pro Asp Gly Glu Ser Leu Thr Glu Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
```

```
            275                 280                 285
Ala Ile Phe Ala Glu Val Met Ser Gly Lys Pro Glu Phe Thr Asp His
290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
                340                 345                 350

Ala Leu Arg Thr Ser Pro Gln Trp Leu Gly Pro Gln Ile Glu Val Ile
                355                 360                 365

Arg Gln Ala Thr Lys Ser Ile Glu Arg Glu Ile Asn Ser Val Asn Asp
                370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
                420                 425                 430

Asn Asp Phe Tyr Asn Asn Gly Leu Pro Ser Asn Leu Thr Ala Ser Ser
                435                 440                 445

Asn Pro Ser Leu Asp Tyr Gly Phe Lys Gly Ala Glu Ile Ala Met Ala
450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
                500                 505                 510

Ser Thr Thr Phe Leu Val Gly Ile Cys Gln Ala Val Asp Leu Arg His
                515                 520                 525

Leu Glu Glu Asn Leu Arg Gln Thr Val Lys Asn Thr Val Ser Gln Val
                530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
                580                 585                 590

Arg Leu Arg Gln Val Ile Val Asp His Ala Leu Ser Asn Gly Glu Thr
                595                 600                 605

Glu Lys Asn Ala Val Thr Ser Ile Phe Gln Lys Ile Gly Ala Phe Glu
                610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
                660                 665                 670

Leu Leu Thr Gly Glu Lys Val Val Ser Pro Gly Glu Glu Phe Asp Lys
                675                 680                 685

Val Phe Thr Ala Met Cys Glu Gly Lys Leu Ile Asp Pro Leu Met Asp
690                 695                 700
```

```
Cys Leu Lys Glu Trp Asn Gly Ala Pro Ile Pro Ile Cys
705                 710                 715
```

```
<210> SEQ ID NO 14
<211> LENGTH: 227
<212> TYPE: PRT
<213> ORGANISM: Aspergillus niger
<220> FEATURE:
<221> NAME/KEY: MISC_FEATURE
<223> OTHER INFORMATION: Amino acid sequence for phenylacrylic acid
      decarboxylase, AnPAD

<400> SEQUENCE: 14
```

```
Met Phe Asn Ser Leu Leu Ser Gly Thr Thr Pro Asn Ser Gly Arg
1               5                   10                  15

Ala Ser Pro Pro Ala Ser Glu Met Pro Ile Asp Asn Asp His Val Ala
                20                  25                  30

Val Ala Arg Pro Ala Pro Arg Arg Arg Ile Val Val Ala Met Thr
            35                  40                  45

Gly Ala Thr Gly Ala Met Leu Gly Ile Lys Val Leu Ile Ala Leu Arg
    50                  55                  60

Arg Leu Asn Val Glu Thr His Leu Val Met Ser Lys Trp Ala Glu Ala
65                  70                  75                  80

Thr Ile Lys Tyr Glu Thr Asp Tyr His Pro Ser Asn Val Arg Ala Leu
                85                  90                  95

Ala Asp Tyr Val His Asn Ile Asn Asp Met Ala Ala Pro Val Ser Ser
                100                 105                 110

Gly Ser Phe Arg Ala Asp Gly Met Ile Val Val Pro Cys Ser Met Lys
            115                 120                 125

Thr Leu Ala Ala Ile His Ser Gly Phe Cys Asp Asp Leu Ile Ser Arg
    130                 135                 140

Thr Ala Asp Val Met Leu Lys Glu Arg Arg Leu Val Leu Val Ala
145                 150                 155                 160

Arg Glu Thr Pro Leu Ser Glu Ile His Leu Arg Asn Met Leu Glu Val
                165                 170                 175

Thr Arg Ala Gly Ala Val Ile Phe Pro Pro Val Pro Ala Phe Tyr Ile
            180                 185                 190

Lys Ala Gly Ser Ile Glu Asp Leu Ile Asp Gln Ser Val Gly Arg Met
        195                 200                 205

Leu Asp Leu Phe Asp Leu Asp Thr Gly Asp Phe Glu Arg Trp Asn Gly
    210                 215                 220

Trp Glu Lys
225
```

```
<210> SEQ ID NO 15
<211> LENGTH: 2154
<212> TYPE: DNA
<213> ORGANISM: Arabidopsis thaliana
<220> FEATURE:
<221> NAME/KEY: misc_feature
<223> OTHER INFORMATION: DNA sequence for phenylalanine ammonia lyase,
      AtPAL

<400> SEQUENCE: 15
```

```
atggatcaaa tcgaagcaat gttgtgcggc ggaggagaga agacaaaagt ggcggttact      60
acgaagactt tggcagatcc attgaattgg ggtttagcag cggatcaaat gaaaggaagt     120
catttagatg aagtgaagaa gatggtcgaa gagtatcgta gaccagtcgt gaatcttggc     180
```

-continued

```
ggagaaacac tgacgatcgg acaagttgct gccatctcca ccgtaggagg cagcgttaag    240
gttgagttag cggagacttc aagagccggt gtgaaagcta gcagtgattg ggttatggag    300
agcatgaaca aaggtactga cagttacgga gtcaccaccg gctttggtgc tacttctcac    360
cggagaacca aaaacggcac cgcattacaa acagaactca ttagatttt gaacgccgga     420 atattcggaa acacgaagga gacatgtcac acactgccgc aatccgccac aagagccgcc    480
atgctcgtca gagtcaacac tcttctccaa ggatactccg ggatccgatt cgagatcctc    540
gaagcgatta caagtctcct caaccacaac atctctccgt cactacctct ccgtggaacc    600
attaccgcct ccgggcatct cgttcctctc tcttacatcg ccggacttct caccggccgt    660
cctaattcca aagccaccgg tcccgacggt gaatcgctaa ccgagaaaga agcttttgag    720
aaagccggaa tcagtactgg attcttcgat ttacaaccta aggaaggttt agctctcgtt    780
aatggcacgg cggttggatc tggaatggcg tcgatggttc tattcgaagc gaatgtccaa    840
gcggtgttag cggaggtttt atcagcgatc ttcgcggagg ttatgagcgg gaaacctgag    900
tttaccgatc atctgactca tcgttaaaa catcatcccg acaaatcga agcggcggcg     960 ataatggagc acatactcga cggaagctca tacatgaaat tagctcaaaa ggttcacgag    1020
atggatccat tgcagaaacc aaaacaagat cgttacgctc ttcgtacatc tcctcaatgg    1080
ctaggtcctc aaattgaagt aatccgtcaa gctacgaaat cgatagagcg tgaaatcaac    1140
tccgttaacg ataatccgtt gatcgatgtt tcgaggaaca aggcgattca cggtggtaac    1200
ttccaaggaa caccaatcgg agtttctatg gataacacga gattggcgat gctgcgatt    1260 gggaagctaa tgtttgctca attctctgag cttgttaatg atttctacaa caatggactt    1320
ccttcgaatc taactgcttc gagtaatcca agtttggatt atggattcaa aggagcagag    1380
attgctatgg cttcttattg ttctgagctt caatacttgg ctaatccagt cacaagccat    1440
gttcaatcag ctgagcaaca taatcaagat gtgaactctc ttggtttgat ctcgtctcgt    1500
aaaacatctg aagctgtgga tattcttaag ctaatgtcaa caacgttcct tgtggggata    1560
tgtcaagctg ttgatttgag acatttggag gagaatctga caaaactgt gaagaacaca    1620 gtttctcaag ttgctaagaa agtgttaacc actggaatca acggtgagtt acatccgtca    1680
aggttttgcg agaaggactt gcttaaggtt gttgatcgtg agcaagtgtt cacgtatgtg    1740
gatgatcctt gtagcgctac gtacccgttg atgcagagac taagacaagt tattgttgat    1800
cacgctttgt ccaacggtga gactgagaag aatgcagtga cttcgatctt tcaaaagatt    1860
ggagcttttg aagaggagct taaggctgtg cttccaaagg aagttgaagc ggctagagcg    1920
gcttatggga atggaactgc gccgattcct aaccggatta aggaatgtag gtcgtatccg    1980
ttgtataggt tcgtgaggga agagcttgga acgaagttgt tgactggaga aaaggttgtg    2040
tctccgggag aggagtttga taaggtcttc actgctatgt gtgaaggtaa acttattgat    2100
ccgttgatgg attgtctcaa ggaatggaac ggagctccga ttccgatttg ctaa          2154
```

<210> SEQ ID NO 16
<211> LENGTH: 687
<212> TYPE: DNA
<213> ORGANISM: Aspergillus niger
<220> FEATURE:
<221> NAME/KEY: misc_feature
<223> OTHER INFORMATION: DNA sequence for phenylacrylic acid
      decarboxylase, AnPAD

<400> SEQUENCE: 16

```
atgatgttca actcacttct gtccggcact actacaccaa actccggccg tgcaagccct    60
```

```
ccggcaagcg aaatgccgat tgataacgac catgttgcag tcgcacgtcc ggcaccgcgt    120
cgccgtcgca tcgtggttgc aatgaccggt gcaacgggtg caatgctggg cattaaagtg    180
ctgatcgccc tgcgtcgcct gaacgtcgaa acccacctgg tgatgagtaa atgggcagaa    240
gctaccatta aatatgaaac ggattaccat ccgtcaaatg tgcgcgcgct ggccgattat    300
gttcacaaca ttaatgacat ggcggcccccg gttagctctg gcagctttcg tgcggatggt    360
atgatcgtcg tgccgtgctc tatgaaaacc ctggcagcta ttcatagtgg cttctgtgat    420
gacctgatct cccgcacggc agatgtcatg ctgaaagaac gtcgccgtct ggtgctggtt    480
gctcgtgaaa ccccgctgtc cgaaatccac ctgcgcaaca tgctggaagt tacgcgtgca    540
ggtgctgtta ttttccgcc ggtcccggca ttctacatca aagctggctc aattgaagat    600
ctgatcgacc agtcggtggg tcgcatgctg gacctgtttg atctggacac cggcgacttc    660
gaacgttgga atggttggga aaaataa                                        687
```

<210> SEQ ID NO 17
<211> LENGTH: 350
<212> TYPE: PRT
<213> ORGANISM: Escherichia coli
<220> FEATURE:
<221> NAME/KEY: MISC_FEATURE
<223> OTHER INFORMATION: Amino acid sequence for DAHP synthase AroG

<400> SEQUENCE: 17

```
Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
                100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
        130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
        210                 215                 220

Gly Asn Gly Asp Cys His Ile Ile Leu Arg Gly Gly Lys Glu Pro Asn
225                 230                 235                 240
```

```
Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 18
<211> LENGTH: 173
<212> TYPE: PRT
<213> ORGANISM: Escherichia coli
<220> FEATURE:
<221> NAME/KEY: MISC_FEATURE
<223> OTHER INFORMATION: Amino acid sequence for shikimate kinase AroK

<400> SEQUENCE: 18

Met Ala Glu Lys Arg Asn Ile Phe Leu Val Gly Pro Met Gly Ala Gly
1               5                   10                  15

Lys Ser Thr Ile Gly Arg Gln Leu Ala Gln Gln Leu Asn Met Glu Phe
            20                  25                  30

Tyr Asp Ser Asp Gln Glu Ile Glu Lys Arg Thr Gly Ala Asp Val Gly
        35                  40                  45

Trp Val Phe Asp Leu Glu Gly Glu Glu Gly Phe Arg Asp Arg Glu Glu
    50                  55                  60

Lys Val Ile Asn Glu Leu Thr Glu Lys Gln Gly Ile Val Leu Ala Thr
65                  70                  75                  80

Gly Gly Gly Ser Val Lys Ser Arg Glu Thr Arg Asn Arg Leu Ser Ala
                85                  90                  95

Arg Gly Val Val Val Tyr Leu Glu Thr Thr Ile Glu Lys Gln Leu Ala
            100                 105                 110

Arg Thr Gln Arg Asp Lys Lys Arg Pro Leu Leu His Val Glu Thr Pro
        115                 120                 125

Pro Arg Glu Val Leu Glu Ala Leu Ala Asn Glu Arg Asn Pro Leu Tyr
    130                 135                 140

Glu Glu Ile Ala Asp Val Thr Ile Arg Thr Asp Asp Gln Ser Ala Lys
145                 150                 155                 160

Val Val Ala Asn Gln Ile Ile His Met Leu Glu Ser Asn
                165                 170

<210> SEQ ID NO 19
<211> LENGTH: 288
<212> TYPE: PRT
<213> ORGANISM: Escherichia coli
<220> FEATURE:
<221> NAME/KEY: MISC_FEATURE
<223> OTHER INFORMATION: Amino acid sequence for shikimate dehydrogenase
      YdiB

<400> SEQUENCE: 19

Met Asp Val Thr Ala Lys Tyr Glu Leu Ile Gly Leu Met Ala Tyr Pro
1               5                   10                  15
```

```
Ile Arg His Ser Leu Ser Pro Glu Met Gln Asn Lys Ala Leu Glu Lys
             20                  25                  30

Ala Gly Leu Pro Phe Thr Tyr Met Ala Phe Glu Val Asp Asn Asp Ser
         35                  40                  45

Phe Pro Gly Ala Ile Glu Gly Leu Lys Ala Leu Lys Met Arg Gly Thr
 50                  55                  60

Gly Val Ser Met Pro Asn Lys Gln Leu Ala Cys Glu Tyr Val Asp Glu
 65                  70                  75                  80

Leu Thr Pro Ala Ala Lys Leu Val Gly Ala Ile Asn Thr Ile Val Asn
                 85                  90                  95

Asp Asp Gly Tyr Leu Arg Gly Tyr Asn Thr Asp Gly Thr Gly His Ile
                100                 105                 110

Arg Ala Ile Lys Glu Ser Gly Phe Asp Ile Lys Gly Lys Thr Met Val
            115                 120                 125

Leu Leu Gly Ala Gly Gly Ala Ser Thr Ala Ile Gly Ala Gln Gly Ala
            130                 135                 140

Ile Glu Gly Leu Lys Glu Ile Lys Leu Phe Asn Arg Arg Asp Glu Phe
145                 150                 155                 160

Phe Asp Lys Ala Leu Ala Phe Ala Gln Arg Val Asn Glu Asn Thr Asp
                165                 170                 175

Cys Val Val Thr Val Thr Asp Leu Ala Asp Gln Gln Ala Phe Ala Glu
                180                 185                 190

Ala Leu Ala Ser Ala Asp Ile Leu Thr Asn Gly Thr Lys Val Gly Met
            195                 200                 205

Lys Pro Leu Glu Asn Glu Ser Leu Val Asn Asp Ile Ser Leu Leu His
            210                 215                 220

Pro Gly Leu Leu Val Thr Glu Cys Val Tyr Asn Pro His Met Thr Lys
225                 230                 235                 240

Leu Leu Gln Gln Ala Gln Gln Ala Gly Cys Lys Thr Ile Asp Gly Tyr
                245                 250                 255

Gly Met Leu Leu Trp Gln Gly Ala Glu Gln Phe Thr Leu Trp Thr Gly
            260                 265                 270

Lys Asp Phe Pro Leu Glu Tyr Val Lys Gln Val Met Gly Phe Gly Ala
            275                 280                 285

<210> SEQ ID NO 20
<211> LENGTH: 386
<212> TYPE: PRT
<213> ORGANISM: Escherichia coli
<220> FEATURE:
<221> NAME/KEY: MISC_FEATURE
<223> OTHER INFORMATION: Amino acid sequence for chorismate
      mutase/prephenate dehydratase PheA

<400> SEQUENCE: 20

Met Thr Ser Glu Asn Pro Leu Leu Ala Leu Arg Glu Lys Ile Ser Ala
 1               5                  10                  15

Leu Asp Glu Lys Leu Leu Ala Leu Leu Ala Glu Arg Arg Glu Leu Ala
             20                  25                  30

Val Glu Val Gly Lys Ala Lys Leu Leu Ser His Arg Pro Val Arg Asp
         35                  40                  45

Ile Asp Arg Glu Arg Asp Leu Leu Glu Arg Leu Ile Thr Leu Gly Lys
     50                  55                  60

Ala His His Leu Asp Ala His Tyr Ile Thr Arg Leu Phe Gln Leu Ile
 65                  70                  75                  80
```

```
Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
            340                 345                 350

Ala Glu Met Gln Lys Ala Leu Lys Glu Leu Gly Glu Ile Thr Arg Ser
        355                 360                 365

Met Lys Val Leu Gly Cys Tyr Pro Ser Glu Asn Val Val Pro Val Asp
    370                 375                 380

Pro Thr
385

<210> SEQ ID NO 21
<211> LENGTH: 397
<212> TYPE: PRT
<213> ORGANISM: Escherichia coli
<220> FEATURE:
<221> NAME/KEY: MISC_FEATURE
<223> OTHER INFORMATION: Amino acid sequence for tyrosine
      aminotransferase TyrB

<400> SEQUENCE: 21

Met Phe Gln Lys Val Asp Ala Tyr Ala Gly Asp Pro Ile Leu Thr Leu
1               5                   10                  15

Met Glu Arg Phe Lys Glu Asp Pro Arg Ser Asp Lys Val Asn Leu Ser
            20                  25                  30

Ile Gly Leu Tyr Tyr Asn Glu Asp Gly Ile Ile Pro Gln Leu Gln Ala
```

Val Ala Glu Ala Glu Ala Arg Leu Asn Ala Gln Pro His Gly Ala Ser
 35                  40                  45

Leu Tyr Leu Pro Met Glu Gly Leu Asn Cys Tyr Arg His Ala Ile Ala
 50                  55                  60

Pro Leu Leu Phe Gly Ala Asp His Pro Val Leu Lys Gln Gln Arg Val
 65                  70                  75                  80

Ala Thr Ile Gln Thr Leu Gly Gly Ser Gly Ala Leu Lys Val Gly Ala
             85                  90                  95

Asp Phe Leu Lys Arg Tyr Phe Pro Glu Ser Gly Val Trp Val Ser Asp
         100                 105                 110

Pro Thr Trp Glu Asn His Val Ala Ile Phe Ala Gly Ala Gly Phe Glu
     115                 120                 125

Val Ser Thr Tyr Pro Trp Tyr Asp Glu Ala Thr Asn Gly Val Arg Phe
 130                 135                 140

Asn Asp Leu Leu Ala Thr Leu Lys Thr Leu Pro Ala Arg Ser Ile Val
 145                 150                 155                 160

Leu Leu His Pro Cys Cys His Asn Pro Thr Gly Ala Asp Leu Thr Asn
             165                 170                 175

Asp Gln Trp Asp Ala Val Ile Glu Ile Leu Lys Ala Arg Glu Leu Ile
         180                 185                 190

Pro Phe Leu Asp Ile Ala Tyr Gln Gly Phe Gly Ala Gly Met Glu Glu
     195                 200                 205

Asp Ala Tyr Ala Ile Arg Ala Ile Ala Ser Ala Gly Leu Pro Ala Leu
 210                 215                 220

Val Ser Asn Ser Phe Ser Lys Ile Phe Ser Leu Tyr Gly Glu Arg Val
 225                 230                 235                 240

Gly Gly Leu Ser Val Met Cys Glu Asp Ala Glu Ala Ala Gly Arg Val
             245                 250                 255

Leu Gly Gln Leu Lys Ala Thr Val Arg Arg Asn Tyr Ser Ser Pro Pro
         260                 265                 270

Asn Phe Gly Ala Gln Val Val Ala Ala Val Leu Asn Asp Glu Ala Leu
     275                 280                 285

Lys Ala Ser Trp Leu Ala Glu Val Glu Glu Met Arg Thr Arg Ile Leu
 290                 295                 300

Ala Met Arg Gln Glu Leu Val Lys Val Leu Ser Thr Glu Met Pro Glu
 305                 310                 315                 320

Arg Asn Phe Asp Tyr Leu Leu Asn Gln Arg Gly Met Phe Ser Tyr Thr
             325                 330                 335

Gly Leu Ser Ala Ala Gln Val Asp Arg Leu Arg Glu Glu Phe Gly Val
         340                 345                 350

Tyr Leu Ile Ala Ser Gly Arg Met Cys Val Ala Gly Leu Asn Thr Ala
     355                 360                 365

Asn Val Gln Arg Val Ala Lys Ala Phe Ala Ala Val Met
 370                 375                 380

<210> SEQ ID NO 22
<211> LENGTH: 1053
<212> TYPE: DNA
<213> ORGANISM: Escherichia coli
<220> FEATURE:
<221> NAME/KEY: misc_feature
<223> OTHER INFORMATION: DNA sequence for DAHP synthase AroG

<400> SEQUENCE: 22

```
atgaattatc agaacgacga tttacgcatc aaagaaatca aagagttact tcctcctgtc      60
gcattgctgg aaaaattccc cgctactgaa aatgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg      420 gcaggtgagt ttctcgatat gatcacccca caatatctcg ctgacctgat gagctggggc     480
gcaattggcg cacgtaccac cgaatcgcag gtgcaccgcg aactggcatc agggctttct     540
tgtccggtcg gcttcaaaaa tggcaccgac ggtacgatta agtggctat cgatgccatt      600 aatgccgccg gtgcgccgca ctgcttcctg tccgtaacga aatgggggca ttcggcgatt     660
gtgaatacca gcggtaacgg cgattgccat atcattctgc gcggcggtaa agagcctaac     720
tacagcgcga agcacgttgc tgaagtgaaa gaagggctga caaaagcagg cctgccagca     780
caggtgatga tcgatttcag ccatgctaac tcgtccaaac aattcaaaaa gcagatggat     840
gtttgtgctg acgtttgcca gcagattgcc ggtggcgaaa aggccattat tggcgtgatg     900
gtggaaagcc atctggtgga aggcaatcag agcctcgaga gcggggagcc gctggcctac     960
ggtaagagca tcaccgatgc ctgcatcggc tgggaagata ccgatgctct gttacgtcaa    1020
ctggcgaatg cagtaaaagc gcgtcgcggg taa                                 1053

<210> SEQ ID NO 23
<211> LENGTH: 522
<212> TYPE: DNA
<213> ORGANISM: Escherichia coli
<220> FEATURE:
<221> NAME/KEY: misc_feature
<223> OTHER INFORMATION: DNA sequence for shikimate kinase AroK

<400> SEQUENCE: 23
atggcagaga aacgcaatat ctttctggtt gggcctatgg gtgccggaaa aagcactatt      60
gggcgccagt tagctcaaca actcaatatg gaattttacg attccgatca agagattgag     120
aaacgaaccg gagctgatgt gggctgggtt ttcgatttag aaggcgaaga aggcttccgc     180
gatcgcgaag aaaaggtcat caatgagttg accgagaaac agggtattgt gctggctact     240
ggcggcggct ctgtgaaatc ccgtgaaacg cgtaaccgtc tttccgctcg tggcgttgtc     300
gtttatcttg aaacgaccat cgaaaagcaa cttgcacgca cgcagcgtga taaaaaacgc     360
ccgttgctgc acgttgaaac accgccgcgt gaagttctgg aagcgttggc caatgaacgc     420
aatccgctgt atgaagagat tgccgacgtg accattcgta ctgatgatca aagcgctaaa     480
gtggttgcaa accagattat tcacatgctg gaaagcaact aa                       522

<210> SEQ ID NO 24
<211> LENGTH: 867
<212> TYPE: DNA
<213> ORGANISM: Escherichia coli
<220> FEATURE:
<221> NAME/KEY: misc_feature
<223> OTHER INFORMATION: DNA sequence for shikimate dehydrogenase YdiB

<400> SEQUENCE: 24
atggatgtta ccgcaaaata cgaattgatt gggttgatgg cctatccgat ccgccacagt      60
ttatcgcccg aaatgcagaa taaagcctta gaaaaagcgg gattgccatt tacctatatg     120
```

```
gccttcgaag tggataacga tagctttcct ggagcaattg aaggattaaa agccctcaaa      180
atgcgcggaa ctggtgtatc gatgccgaac aaacaactgg cgtgtgaata tgttgatgaa      240
ttaacaccag ctgccaaact ggtgggggcc atcaacacca tcgttaatga tgatggctat      300
ctgcgtggct ataacaccga cggcacgggc catattcgcg ccattaaaga gagcggtttt      360
gatatcaaag gcaaaacgat ggtgctgtta ggggccggtg gtgcctcaac ggcaattggc      420
gcgcaggggg caattgaagg tttaaaagaa attaaactct taaccgtcg ggatgagttc       480 ttcgataaag ccctcgcctt cgcgcagcgg gttaatgaaa acaccgattg tgtcgtcacg      540
gtcaccgatc tcgccgatca gcaagccttt gctgaagccc tggcttccgc cgacatttta      600
accaatggca caaaagtggg tatgaaaccc cttgagaatg aatcattggt taatgatatc      660
agtctgttac atccgggact tctggtcact gaatgcgtgt ataacccgca tatgacgaag      720
ttattgcagc aggcgcaaca agctggttgc aaaacgattg atggatacgg catgttgttg      780
tggcaagggg ctgaacagtt cacattatgg actggcaaag atttccctct ggaatatgtt      840
aaacaggtca tggggttcgg tgcctga                                          867
```

```
<210> SEQ ID NO 25
<211> LENGTH: 1161
<212> TYPE: DNA
<213> ORGANISM: Escherichia coli
<220> FEATURE:
<221> NAME/KEY: misc_feature
<223> OTHER INFORMATION: DNA sequence for chorismate mutase/prephenate
      dehydratase PheA

<400> SEQUENCE: 25
atgacatcgg aaaacccgtt actggcgctg cgagagaaaa tcagcgcgct ggatgaaaaa       60
ttattagcgt tactggcaga acggcgcgaa ctggccgtcg aggtgggaaa agccaaactg      120
ctctcgcatc gcccggtacg tgatattgat cgtgaacgcg atttgctgga aagattaatt      180
acgctcggta aagcgcacca tctggacgcc attacatta ctcgcctgtt ccagctcatc       240
attgaagatt ccgtattaac tcagcaggct ttgctccaac aacatctcaa taaaattaat      300
ccgcactcag cacgcatcgc ttttctcggc cccaaaggtt cttattccca tcttgcggcg      360
cgccagtatg ctgcccgtca cttttgagcaa ttcattgaaa gtggctgcgc caaatttgcc      420
gatattttta atcaggtgga aaccggccag gccgactatg ccgtcgtacc gattgaaaat      480
accagctccg gtgccataaa cgacgtttac gatctgctgc aacataccag cttgtcgatt      540
gttggcgaga tgacgttaac tatcgaccat tgtttgttgg tctccggcac tactgattta      600
tccaccatca atacggtcta cagccatccg cagccattcc agcaatgcag caaattcctt      660
aatcgttatc cgcactggaa gattgaatat accgaaagta cgtctgcggc aatggaaaag      720
gttgcacagg caaaatcacc gcatgttgct gcgttgggaa gcgaagctgg cggcactttg      780
tacggtttgc aggtactgga gcgtattgaa gcaaatcagc gacaaaactt cacccgattt      840
gtggtgttgg cgcgtaaagc cattaacgtg tctgatcagg ttccggcgaa aaccacgttg      900
ttaatggcga ccgggcaaca agccggtgcg ctggttgaag cgttgctggt actgcgcaac      960
cacaatctga ttatgacccg tctgaatca cgcccgattc acggtaatcc atgggaagag      1020
atgttctatc tggatattca ggccaatctt gaatcagcgg aaatgcaaaa agcattgaaa     1080
gagttagggg aaatcacccg ttcaatgaag gtattgggct gttacccaag tgagaacgta     1140
gtgcctgttg atccaacctg a                                               1161
```

<210> SEQ ID NO 26
<211> LENGTH: 1194
<212> TYPE: DNA
<213> ORGANISM: Escherichia coli
<220> FEATURE:
<221> NAME/KEY: misc_feature
<223> OTHER INFORMATION: DNA acid sequence for tyrosine aminotransferase
      TyrB

<400> SEQUENCE: 26

| | | | | | | |
|---|---|---|---|---|---|---|
| gtgtttcaaa | aagttgacgc | ctacgctggc | gacccgattc | ttacgcttat | ggagcgtttt | 60 |
| aaagaagacc | ctcgcagcga | caaagtgaat | ttaagtatcg | gtctgtacta | caacgaagac | 120 |
| ggaattattc | cacaactgca | agccgtggcg | gaggcggaag | cgcgcctgaa | tgcgcagcct | 180 |
| catggcgctt | cgctttattt | accgatgaa | gggcttaact | gctatcgcca | tgccattgcg | 240 |
| ccgctgctgt | ttggtgcgga | ccatccggta | ctgaaacaac | agcgcgtagc | aaccattcaa | 300 |
| acccttggcg | gctccggggc | attgaaagtg | ggcgcggatt | tcctgaaacg | ctacttcccg | 360 |
| gaatcaggcg | tctgggtcag | cgatcctacc | tgggaaaacc | acgtagcaat | attcgccggg | 420 |
| gctggattcg | aagtgagtac | ttaccctgg | tatgacgaag | cgactaacgg | cgtgcgcttt | 480 |
| aatgacctgt | tggcgacgct | gaaaacatta | cctgcccgca | gtattgtgtt | gctgcatcca | 540 |
| tgttgccaca | acccaacggg | tgccgatctc | actaatgatc | agtgggatgc | ggtgattgaa | 600 |
| attctcaaag | cccgcgagct | tattccattc | tcgatattg | cctatcaagg | atttggtgcc | 660 |
| ggtatggaag | aggatgccta | cgctattcgc | gccattgcca | cgctggatt | acccgctctg | 720 |
| gtgagcaatt | cgttctcgaa | aatttttctcc | ctttacggcg | agcgcgtcgg | cggactttct | 780 |
| gttatgtgtg | aagatgccga | agccgctggc | cgcgtactgg | ggcaattgaa | agcaacagtt | 840 |
| cgccgcaact | actccagccc | gccgaatttt | ggtgcgcagg | tggtggctgc | agtgctgaat | 900 |
| gacgaggcat | tgaaagccag | ctggctggcg | gaagtagaag | agatgcgtac | tcgcattctg | 960 |
| gcaatgcgtc | aggaattggt | gaaggtatta | agcacagaga | tgccagaacg | caatttcgat | 1020 |
| tatctgctta | atcagcgcgg | catgttcagt | tataccggtt | taagtgccgc | tcaggttgac | 1080 |
| cgactacgtg | aagaatttgg | tgtctatctc | atcgccagcg | gtcgcatgtg | tgtcgccggg | 1140 |
| ttaaatacgg | caaatgtaca | acgtgtggca | aaggcgtttg | ctgcggtgat | gtaa | 1194 |

<210> SEQ ID NO 27
<211> LENGTH: 903
<212> TYPE: DNA
<213> ORGANISM: Escherichia coli
<220> FEATURE:
<221> NAME/KEY: misc_feature
<223> OTHER INFORMATION: DNA sequence for feedback inhibition resistant
      AroG*

<400> SEQUENCE: 27

| | | | | | | |
|---|---|---|---|---|---|---|
| atgacatcgg | aaagcccgtt | accggcgctg | cgagagaaaa | tcagcgcgct | ggatgaaaaa | 60 |
| ttattagcgt | tactggcaga | acggcgcgaa | ctggccgtcg | aggtgggaaa | agccaaactg | 120 |
| ctctcgcatc | gcccggtacg | tgatattgat | cgtgaacgca | acatgctgga | agattaatt | 180 |
| acgctcggta | aagcgcacca | tctggacgcc | attacatta | ctcgcctgtt | ccagctcatc | 240 |
| attgaagatt | ccgtattaac | tcagcaggct | ttgctccaac | aacatctcaa | taaaattaat | 300 |
| ccgcactcag | cacgcatcgc | ttttctcggc | cccaaaggtt | cttattccca | tcttgcgggcg | 360 |
| cgccagtatg | ctgcccgtca | ctttgagcaa | ttcattgaaa | gtggctgcgc | caaatttgcc | 420 |
| gatattttta | atcaggtgga | aaccggccag | gccgactatg | ccgtcgtacc | gattgaaaat | 480 |

```
accagctccg gtgccataaa cgacgtttac gatctgctgc aacataccag cttgtcgatt      540
gttggcgaga tgacgttaac tatcgaccat tgtttgttgg tctccggcac tactgattta      600
tccaccatca atacggtcta cagccatccg cagccattcc agcaatgcag caaattcctt      660
aatcgttatc cgcactggaa gattgaatat accgaaagta cggcggcggc aatggaaaag      720
gttgcacagg caaaatcacc gcatgttgct gcgttgggaa gcgaagctgg cggcactttg      780
tacggtttgc aggtactgga gcgtattgaa gcaaatcagc gacaaaactt cacccgattt      840
gtggtgttgg cgcgtaaagc cattaacgtg tctgatcagg ttccggcgaa aaccacgttg      900
tga                                                                    903

<210> SEQ ID NO 28
<211> LENGTH: 1056
<212> TYPE: DNA
<213> ORGANISM: Escherichia coli
<220> FEATURE:
<221> NAME/KEY: misc_feature
<223> OTHER INFORMATION: DNA sequence for feedback inhibition resistant
      PheA*

<400> SEQUENCE: 28
atggtgaatt atcagaacga cgatttacgc atcaaagaaa tcaaagagtt acttcctcct       60
gtcgcattgc tggaaaaatt ccccgctact gaaaatgccg cgaatacggt tgcccatgcc      120
cgaaaagcga tccataagat cctgaaaggt aatgatgatc gcctgttggt tgtgattggc      180
ccatgctcaa ttcatgatcc tgtcgcggca aaagagtatg ccactcgctt gctggcgctg      240
cgtgaagagc tgaaagatga gctggaaatc gtaatgcgcg tctattttga aaagccgcgt      300
accacggtgg gctggaaagg gctgattaac gatccgcaca tggataatag cttccagatc      360
aacgacggtc tgcgtatagc ccgtaaattg ctgcttgata ttaacgacag cggtctgcca      420
gcggcaggtg agtttctcaa catgatcacc ccacaatatc tcgctgacct gatgagctgg      480
ggcgcaattg gcgcacgtac caccgaatcg caggtgcacc gcgaactggc atcagggctt      540
tcttgtccgg tcggcttcaa aaatggcacc gacggtacga ttaaagtggc tatcgatgcc      600
attaatgccg ccggtgcgcc gcactgcttc ctgtccgtaa cgaaatgggg gcattcggcg      660
attgtgaata ccagcggtaa cggcgattgc catatcattc tgcgcggcgg taaagagcct      720
aactacagcg cgaagcacgt tgctgaagtg aaagaagggc tgaacaaagc aggcctgcca      780
gcacaggtga tgatcgattt cagccatgct aactcgtcca aacaattcaa aaagcagatg      840
gatgtttgtg ctgacgtttg ccagcagatt gccggtggcg aaaaggccat tattggcgtg      900
atggtggaaa gccatctggt ggaaggcaat cagagcctcg agagcgggga gccgctggcc      960
tacggtaaga gcatcaccga tgcctgcatc ggctgggaag ataccgatgc tctgttacgt     1020
caactggcga atgcagtaaa agcgcgtcgc gggtaa                                1056

<210> SEQ ID NO 29
<211> LENGTH: 49
<212> TYPE: DNA
<213> ORGANISM: Artificial Sequence
<220> FEATURE:
<223> OTHER INFORMATION: StyC-KpnI-RBS Forward Primer

<400> SEQUENCE: 29
cgggtaccta aggagatata taatgttaca cgcgtttgaa cgtaaaatg                   49

<210> SEQ ID NO 30
```

```
<211> LENGTH: 47
<212> TYPE: DNA
<213> ORGANISM: Artificial Sequence
<220> FEATURE:
<223> OTHER INFORMATION: StyC-HindIII-XhoI Reverse Primer

<400> SEQUENCE: 30
actgctcgag aagcttactc ggctgccgcg tgtggaacgg ctttacg          47

<210> SEQ ID NO 31
<211> LENGTH: 32
<212> TYPE: DNA
<213> ORGANISM: Artificial Sequence
<220> FEATURE:
<223> OTHER INFORMATION: StyA-BspHI Forward Primer

<400> SEQUENCE: 31
actgtcatga aaaagcgtat cggtattgtt gg                          32

<210> SEQ ID NO 32
<211> LENGTH: 48
<212> TYPE: DNA
<213> ORGANISM: Artificial Sequence
<220> FEATURE:
<223> OTHER INFORMATION: PAR-HindIII-RBS Forward Primer

<400> SEQUENCE: 32
actgaagctt taaggagata tataatgagc gtgaccgcga aaaccgtg         48

<210> SEQ ID NO 33
<211> LENGTH: 35
<212> TYPE: DNA
<213> ORGANISM: Artificial Sequence
<220> FEATURE:
<223> OTHER INFORMATION: PAR-XhoI Reverse Primer

<400> SEQUENCE: 33
actgctcgag tcacatgctt gaactcccgc cgaaa                       35

<210> SEQ ID NO 34
<211> LENGTH: 1137
<212> TYPE: DNA
<213> ORGANISM: Bacillus subtilis str.168
<220> FEATURE:
<221> NAME/KEY: misc_feature
<223> OTHER INFORMATION: DNA sequence for AlaDH

<400> SEQUENCE: 34
atgatcatag gggttcctaa agagataaaa aacaatgaaa accgtgtcgc attaacaccc    60
gggggcgttt ctcagctcat ttcaaacggc caccgggtgc tggttgaaac aggcgcgggc   120
cttggaagcg gatttgaaaa tgaagcctat gagtcagcag gagcgaaaat cattgctgat   180
ccgaagcagg tctgggacgc cgaaatggtc atgaaagtaa agaaccgct  gccggaagaa   240 tatgtttatt ttcgcaaagg acttgtgctg tttacgtacc ttcatttagc agctgagcct   300
gagcttgcac aggccttgaa ggataaagga gtaactgcca tcgcatatga aacggtcagt   360
gaaggccgga cattgcctct tctgacgcca atgtcagagg ttgcgggcag aatggcagcg   420
caaatcggcg ctcaattctt agaaaagcct aaaggcggaa aaggcattct gcttgccggg   480
gtgcctggcg tttccgcgg aaaagtaaca attatcggag gaggcgttgt cgggacaaac   540
gcggcgaaaa tggctgtcgg cctcggtgca gatgtgacga tcattgactt aaacgcagac   600
cgcttgcgcc agcttgatga catcttcggc catcagatta aacgttaat  ttctaatccg   660
```

```
gtcaatattg ctgatgctgt ggcggaagcg atctcctca tttgcgcggt attaattccg      720
ggtgctaaag ctccgactct tgtcactgag gaaatggtaa aacaaatgaa acccggttca      780
gttattgttg atgtagcgat cgaccaaggc ggcatcgtcg aaactgtcga ccatatcaca      840
acacatgatc agccaacata tgaaaaacac ggggttgtgc attatgctgt agcgaacatg      900
ccaggcgcag tccctcgtac atcaacaatc gccctgacta acgttactgt tccatacgcg      960
ctgcaaatcg cgaacaaagg ggcagtaaaa gcgctcgcag acaatacggc actgagagcg     1020
ggtttaaaca ccgcaaacgg acacgtgacc tatgaagctg tagcaagaga tctaggctat     1080
gagtatgttc ctgccgagaa agctttacag gatgaatcat ctgtggcggg tgcttaa       1137
```

```
<210> SEQ ID NO 35
<211> LENGTH: 42
<212> TYPE: DNA
<213> ORGANISM: Artificial Sequence
<220> FEATURE:
<223> OTHER INFORMATION: CvTA-BamHI-BspHI Forward Primer

<400> SEQUENCE: 35
actgggatcc gatcatgatg caaaaacaac gcaccacctc ac                          42

<210> SEQ ID NO 36
<211> LENGTH: 35
<212> TYPE: DNA
<213> ORGANISM: Artificial Sequence
<220> FEATURE:
<223> OTHER INFORMATION: AlaDH-XhoI Reverse Primer

<400> SEQUENCE: 36
actgctcgag ttaagcaccc gccacagatg attca                                  35

<210> SEQ ID NO 37
<211> LENGTH: 50
<212> TYPE: DNA
<213> ORGANISM: Artificial Sequence
<220> FEATURE:
<223> OTHER INFORMATION: EcALDH-NotI-RBS Forward Primer

<400> SEQUENCE: 37
actgcggccg ctaaggagat atataatgac agagccgcat gtagcagtat                  50

<210> SEQ ID NO 38
<211> LENGTH: 36
<212> TYPE: DNA
<213> ORGANISM: Artificial Sequence
<220> FEATURE:
<223> OTHER INFORMATION: EcALDH-XhoI Reverse Primer

<400> SEQUENCE: 38
actgctcgag ttaataccgt acacacaccg acttag                                 36

<210> SEQ ID NO 39
<211> LENGTH: 774
<212> TYPE: DNA
<213> ORGANISM: Pantoea
<220> FEATURE:
<221> NAME/KEY: misc_feature
<223> OTHER INFORMATION: DNA sequence for ADH9v1

<400> SEQUENCE: 39
atgaaaaatc gtgttgcctt tgttaccggt gcaggtcagg gtattggtga agcaattgca      60
ctgcgtctgg caaaagatgg tctggcagtt gcagttgccg atttcaatca agaaaccgca     120
```

```
cgtcaggttg ccgaaaaaat caatcagcag ggtggtaaag ccattgccct gaaagttgat      180
gttagccagc gtgatcaggt tatggaagca gttgaagaag cacgtcgtac cctgggtggt      240
tttgatgtta ttgttaataa tgcaggtatt gcaccgagca ccccgattgc agaaattacc      300
gaagccgttg ttgataaagt gtataacgtg aatgtgaaag gtgtgatttg ggtatgcag       360 gcagcaatta aagcatttgc agccgaaggt catggtggca aaattatcaa tgcatgtagc      420
caggcaggtc atgttggtgc accggaactg gcagtttata gcagcagtaa atttgcagtt      480
cgtggtctga cccagaccgc agcacgtgat ctggcaccgg caggtattac cgttaatgca      540
ttttgtccgg gtattgttcg taccccgatg tgggaagaaa ttgatcgtca gattagcgaa      600
gcagcaggta aaccggcagg ctatggcacc gaagaatttg caaaacgtat tacactgggt      660
cgtctgagcg aaccggaaga tgttgcagca tgtgttgcat atctggcaag tccggatagc      720
gattatatga caggtcagag tctgctgatt gatggtggta tggtgtttaa ctaa            774

<210> SEQ ID NO 40
<211> LENGTH: 50
<212> TYPE: DNA
<213> ORGANISM: Artificial Sequence
<220> FEATURE:
<223> OTHER INFORMATION: ADH9v1-HindIII-RBS Forward Primer

<400> SEQUENCE: 40
actgaagctt taaggagata tatcatgaaa aatcgtgttg cctttgttac                  50

<210> SEQ ID NO 41
<211> LENGTH: 33
<212> TYPE: DNA
<213> ORGANISM: Artificial Sequence
<220> FEATURE:
<223> OTHER INFORMATION: ADH9v1-XhoI Reverse Primer

<400> SEQUENCE: 41
actgctcgag ttagttaaac accataccac cat                                   33

<210> SEQ ID NO 42
<211> LENGTH: 1503
<212> TYPE: DNA
<213> ORGANISM: Aspergillus niger
<220> FEATURE:
<221> NAME/KEY: misc_feature
<223> OTHER INFORMATION: DNA sequence for AnFDC

<400> SEQUENCE: 42
atgagcgcgc aacctgcgca cctgtgcttc cgcagtttcg tggaagcact gaaagttgat      60
aacgatctgg tggaaattaa taccccgatc gatccgaacc tggaagcggc ggcaattacc     120
cgtcgcgtgt gcgaaacgaa tgataaagcc ccgctgttta caatctgat tggcatgaaa      180 aacggtctgt tccgcatcct gggtgcaccg ggcagtctgc gtaaaagctc tgcggatcgt      240
tatggtcgtc tggcacgtca tctggcactg ccgccgaccg caagcatgcg tgaaattctg     300
gataaaatgc tgagtgcgag cgatatgccg ccgattccgc cgaccatcgt gccgacgggt     360
ccgtgtaaag aaaatagcct ggatgattct gaatttgatc tgaccgaact gccggttccg    420
ctgatccata aaagcgatgg cggtaaatat attcagacgt acggtatgca catcgtgcag     480
agtccggatg gcacctggac gaattggagc attgcgcgtg cgatggtgca tgataaaaac    540
cacctgaccg gtctggtgat cccgccgcag catatttggc agatccacca gatgtggaaa    600
aaagaaggtc gtagcgatgt tccgtgggca ctggcattcg gcgtgccgcc ggcggcaatt      660
```

```
atggcgagta gcatgccgat cccggatggt gttaccgaag cgggttatgt gggcgccatg      720
acgggctcta gtctggaact ggttaaatgc gataccaacg atctgtacgt tccggcgacg      780
tctgaaattg tgctggaagg caccctgtct atcagtgaaa cgggtccgga aggcccgttt      840
ggtgaaatgc atggctatat tttcccgggt gataccacc tgggcgccaa atataaagtg       900
aatcgcatta cgtaccgtaa caatgcaatc atgccgatga gcagctgcgg tcgcctgacc      960
gatgaaaccc atacgatgat tggcagcctg gcagcggccg aaatccgtaa actgtgtcag     1020
cagaacgatc tgccgatcac ggatgcattt gcgccgttcg aaagccaggt gacctgggtt     1080
gccctgcgcg ttgatacgga aaaactgcgt gcaatgaaaa ccacgtctga aggttttcgt     1140
aaacgcgtgg gcgatgtggt tttcaatcat aaagcgggtt ataccattca ccgcctggtg     1200
ctggttggtg atgatatcga tgtttacgaa ggcaaagatg tgctgtgggc cttttctacc     1260
cgttgtcgcc cgggtatgga tgaaacgctg tttgaagatg ttcgcggctt cccgctgatt     1320
ccgtacatgg gtcatggcaa cggtccggca caccgtggcg gtaaagttgt tagtgatgcc     1380
ctgatgccga ccgaatatac cacgggtcgt aattgggaag cagcgatttt taaccagtct     1440
tacccggaag acctgaaaca gaaagtgctg gataattgga ccaaaatggg cttcagtaac     1500
taa                                                                    1503
```

<210> SEQ ID NO 43
<211> LENGTH: 500
<212> TYPE: PRT
<213> ORGANISM: Aspergillus niger
<220> FEATURE:
<221> NAME/KEY: MISC_FEATURE
<223> OTHER INFORMATION: Amino acid sequence for AnFDC

<400> SEQUENCE: 43

```
Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
    50                  55                  60

Arg Ile Leu Gly Ala Pro Gly Ser Leu Arg Lys Ser Ser Ala Asp Arg
65                  70                  75                  80

Tyr Gly Arg Leu Ala Arg His Leu Ala Leu Pro Pro Thr Ala Ser Met
                85                  90                  95

Arg Glu Ile Leu Asp Lys Met Leu Ser Ala Ser Asp Met Pro Pro Ile
            100                 105                 110

Pro Pro Thr Ile Val Pro Thr Gly Pro Cys Lys Glu Asn Ser Leu Asp
        115                 120                 125

Asp Ser Glu Phe Asp Leu Thr Glu Leu Pro Val Pro Leu Ile His Lys
    130                 135                 140

Ser Asp Gly Gly Lys Tyr Ile Gln Thr Tyr Gly Met His Ile Val Gln
145                 150                 155                 160

Ser Pro Asp Gly Thr Trp Thr Asn Trp Ser Ile Ala Arg Ala Met Val
                165                 170                 175

His Asp Lys Asn His Leu Thr Gly Leu Val Ile Pro Pro Gln His Ile
            180                 185                 190

Trp Gln Ile His Gln Met Trp Lys Lys Glu Gly Arg Ser Asp Val Pro
        195                 200                 205
```

Trp Ala Leu Ala Phe Gly Val Pro Ala Ala Ile Met Ala Ser Ser
        210                 215                 220

Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
            245                 250                 255

Val Pro Ala Thr Ser Glu Ile Val Leu Glu Gly Thr Leu Ser Ile Ser
            260                 265                 270

Glu Thr Gly Pro Glu Gly Pro Phe Gly Glu Met His Gly Tyr Ile Phe
        275                 280                 285

Pro Gly Asp Thr His Leu Gly Ala Lys Tyr Lys Val Asn Arg Ile Thr
        290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Ala Glu Ile Arg
            325                 330                 335

Lys Leu Cys Gln Gln Asn Asp Leu Pro Ile Thr Asp Ala Phe Ala Pro
            340                 345                 350

Phe Glu Ser Gln Val Thr Trp Val Ala Leu Arg Val Asp Thr Glu Lys
        355                 360                 365

Leu Arg Ala Met Lys Thr Thr Ser Glu Gly Phe Arg Lys Arg Val Gly
        370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
            405                 410                 415

Ala Phe Ser Thr Arg Cys Arg Pro Gly Met Asp Glu Thr Leu Phe Glu
            420                 425                 430

Asp Val Arg Gly Phe Pro Leu Ile Pro Tyr Met Gly His Gly Asn Gly
        435                 440                 445

Pro Ala His Arg Gly Gly Lys Val Val Ser Asp Ala Leu Met Pro Thr
450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
            485                 490                 495

Gly Phe Ser Asn
            500

<210> SEQ ID NO 44
<211> LENGTH: 30
<212> TYPE: DNA
<213> ORGANISM: Artificial Sequence
<220> FEATURE:
<223> OTHER INFORMATION: AnFDC-BspHI Forward Primer

<400> SEQUENCE: 44
actgtcatga gcgcgcaacc tgcgcacctg                                    30

<210> SEQ ID NO 45
<211> LENGTH: 35
<212> TYPE: DNA
<213> ORGANISM: Artificial Sequence
<220> FEATURE:
<223> OTHER INFORMATION: AnFDC-EcoRI Reverse Primer

<400> SEQUENCE: 45

-continued

```
actggaattc ttagttactg aagcccattt tggtc                                35

<210> SEQ ID NO 46
<211> LENGTH: 48
<212> TYPE: DNA
<213> ORGANISM: Artificial Sequence
<220> FEATURE:
<223> OTHER INFORMATION: AnPAD-EcoRI-RBS Forward Primer

<400> SEQUENCE: 46
actggaattc taaggagata tatcatgttc aactcacttc tgtccggc                  48

<210> SEQ ID NO 47
<211> LENGTH: 34
<212> TYPE: DNA
<213> ORGANISM: Artificial Sequence
<220> FEATURE:
<223> OTHER INFORMATION: AnPAD-PstI Reverse Primer

<400> SEQUENCE: 47
actgctgcag ttatttttcc caaccattcc aacg                                 34

<210> SEQ ID NO 48
<211> LENGTH: 33
<212> TYPE: DNA
<213> ORGANISM: Artificial Sequence
<220> FEATURE:
<223> OTHER INFORMATION: AtPAL-NdeI Forward Primer

<400> SEQUENCE: 48
actgcatatg gatcaaatcg aagcaatgtt gtg                                  33

<210> SEQ ID NO 49
<211> LENGTH: 34
<212> TYPE: DNA
<213> ORGANISM: Artificial Sequence
<220> FEATURE:
<223> OTHER INFORMATION: AtPAL-XhoI Reverse Primer

<400> SEQUENCE: 49
actgctcgag ttatttttcc caaccattcc aacg                                 34

<210> SEQ ID NO 50
<211> LENGTH: 300
<212> TYPE: PRT
<213> ORGANISM: Escherichia coli
<220> FEATURE:
<221> NAME/KEY: MISC_FEATURE
<223> OTHER INFORMATION: Amino acid sequence for feedback inhibition
      resistant AroG*

<400> SEQUENCE: 50

Met Thr Ser Glu Ser Pro Leu Pro Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asn Met Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
```

```
                    85                  90                  95
Asn Lys Ile Asn Pro His Ser Ala Arg Ile Ala Phe Leu Gly Pro Lys
                100                 105                 110

Gly Ser Tyr Ser His Leu Ala Ala Arg Gln Tyr Ala Ala Arg His Phe
            115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
                180                 185                 190

Leu Val Ser Gly Thr Thr Asp Leu Ser Thr Ile Asn Thr Val Tyr Ser
            195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu
        290                 295                 300

<210> SEQ ID NO 51
<211> LENGTH: 351
<212> TYPE: PRT
<213> ORGANISM: Escherichia coli
<220> FEATURE:
<221> NAME/KEY: MISC_FEATURE
<223> OTHER INFORMATION: Amino acid sequence for feedback inhibition
      resistant PheA*

<400> SEQUENCE: 51

Met Val Asn Tyr Gln Asn Asp Asp Leu Arg Ile Lys Glu Ile Lys Glu
1               5                   10                  15

Leu Leu Pro Pro Val Ala Leu Leu Glu Lys Phe Pro Ala Thr Glu Asn
                20                  25                  30

Ala Ala Asn Thr Val Ala His Ala Arg Lys Ala Ile His Lys Ile Leu
            35                  40                  45

Lys Gly Asn Asp Asp Arg Leu Leu Val Val Ile Gly Pro Cys Ser Ile
        50                  55                  60

His Asp Pro Val Ala Ala Lys Glu Tyr Ala Thr Arg Leu Leu Ala Leu
65                  70                  75                  80

Arg Glu Glu Leu Lys Asp Glu Leu Glu Ile Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Asn Ser Phe Gln Ile Asn Asp Gly Leu Arg Ile Ala Arg
        115                 120                 125

Lys Leu Leu Leu Asp Ile Asn Asp Ser Gly Leu Pro Ala Ala Gly Glu
    130                 135                 140
```

Phe Leu Asn Met Ile Thr Pro Gln Tyr Leu Ala Asp Leu Met Ser Trp
145                 150                 155                 160

Gly Ala Ile Gly Ala Arg Thr Thr Glu Ser Gln Val His Arg Glu Leu
                165                 170                 175

Ala Ser Gly Leu Ser Cys Pro Val Gly Phe Lys Asn Gly Thr Asp Gly
            180                 185                 190

Thr Ile Lys Val Ala Ile Asp Ala Ile Asn Ala Ala Gly Ala Pro His
        195                 200                 205

Cys Phe Leu Ser Val Thr Lys Trp Gly His Ser Ala Ile Val Asn Thr
    210                 215                 220

Ser Gly Asn Gly Asp Cys His Ile Ile Leu Arg Gly Gly Lys Glu Pro
225                 230                 235                 240

Asn Tyr Ser Ala Lys His Val Ala Glu Val Lys Glu Gly Leu Asn Lys
                245                 250                 255

Ala Gly Leu Pro Ala Gln Val Met Ile Asp Phe Ser His Ala Asn Ser
            260                 265                 270

Ser Lys Gln Phe Lys Lys Gln Met Asp Val Cys Ala Asp Val Cys Gln
        275                 280                 285

Gln Ile Ala Gly Gly Glu Lys Ala Ile Ile Gly Val Met Val Glu Ser
    290                 295                 300

His Leu Val Glu Gly Asn Gln Ser Leu Glu Ser Gly Glu Pro Leu Ala
305                 310                 315                 320

Tyr Gly Lys Ser Ile Thr Asp Ala Cys Ile Gly Trp Glu Asp Thr Asp
                325                 330                 335

Ala Leu Leu Arg Gln Leu Ala Asn Ala Val Lys Ala Arg Arg Gly
            340                 345                 350

<210> SEQ ID NO 52
<211> LENGTH: 1233
<212> TYPE: DNA
<213> ORGANISM: Artificial Sequence
<220> FEATURE:
<223> OTHER INFORMATION: crr deletion fragment

<400> SEQUENCE: 52
gtaaattgcg cattatgttc ccgatgatca tctctgttga agaagtgcgt gcactgcgca      60
aagagatcga aatctacaaa caggaactgc gcgacgaagg taaagcgttt gacgagtcaa     120
ttgaaatcgg cgtaatggtg gaaacaccgg ctgccgcaac aattgcacgt catttagcca     180
aagaagttga tttctttagt atcggcacca atgatttaac gcagtacact ctggcagttg     240
accgtggtaa tgatatgatt tcacaccttt accagccaat gtcaccgtcc gtgctgaact     300
tgatcaagca agttattgat gcttctcatg ctgaaggcaa atggactggc atgtgtggtg     360
agcttgctgg cgatgaacgt gctacacttc tgttgctggg gatgggtctg gacgaattct     420
ctatgagcgc catttctatc ccgcgcatta gaagattat ccgtaacacg aacttcgaag     480
atgcgaaggt gttagcagag caggctcttg ctcaaccgac aacggacgag ttaatgacgc     540
tggttaacaa gttcattgaa gaaaaaacaa tctgctaatc cacgagatgc ggcccaattt     600
actgcttagg agaagatcat gcatcaagaa gtaattcttg ccgcagtgaa aaatggcgcc     660
catcggcgcc atttttttat gcttccgcca gcggcggcaa aatcaattca tcgctctcat     720
gctgctgggt gtagcgcatc acttccagta cgcgcaaccc cgctcggtgc actgcatcgg     780 ttaacgccctt ccctttcagc aagccactga tgagctgagc acaaaacagg tcgccagtcc     840
ctttcaggtc ggttttttacc cgtgaatggg aaatgacatt cacgctgtcg gcagtgacca     900

-continued

```
ccacaacctg catctcctga ttttcttcat taccggaggc gctggtaacc accacccatt      960
ttaatgtgtc tgaaagcaga cttttgcgg cagcaatggc actgtcgaga tcgcggcaat     1020
ttttaccggt caggatttcc aactcaaaga tattgggggt aattccctgc gccagcggca    1080
gtaaatattg tcgatacgct tcgggaaggt caggtttgac ataaattccg ctatcaatat    1140
cgccaatcac cggatcgacc atgatcaata ggtcaggatg gtctttgcgt agcgcagtca    1200
gccactcggc aaggattttg atttgcgatg ccg                                  1233

<210> SEQ ID NO 53
<211> LENGTH: 1157
<212> TYPE: DNA
<213> ORGANISM: Artificial Sequence
<220> FEATURE:
<223> OTHER INFORMATION: tyrA deletion fragment

<400> SEQUENCE: 53
caattggtgc tcgtacaacg gaatcgcaaa ctcaccgtga aatggcctcc gggctttcca      60
tgccggttgg ttttaaaaac ggcaccgacg gcagtctggc aacagcaatt aacgctatgc    120
gcgccgccgc ccagccgcac cgttttgttg gcattaacca ggcagggcag gttgcgttgc    180
tacaaactca ggggaatccg gacggccatg tgatcctgcg cggtggtaaa gcgccgaact    240
atagccctgc ggatgttgcg caatgtgaaa aagagatgga acaggcggga ctgcgcccgt    300
ctctgatggt agattgcagc cacggtaatt ccaataaaga ttatcgccgt cagcctgcgg    360
tggcagaatc cgtggttgct caaatcaaag atggcaatcg ctcaattatt ggtctgatga    420
tcgaaagtaa tatccacgag ggcaatcagt cttccgagca accgcgcagt gaaatgaaat    480
acggtgtatc cgtaaccgat gcctgcatta gctgggaaat gaccgatgcc ttgctgcgtg    540
aaattcatca ggatctgaac gggcagctga cggctcgcgt ggcttaagag gtttattatg    600
tcgccagtaa taatccagtg ccggatgatt cacatcatcc ggcaccttt catcaggttg    660 gatcaacagg cactacgttc tcacttgggt aacagcccaa taccttcatt gaacgggtga    720
tttcccctaa ctctttcaat gcttttttgca tttccgctga ttcaagattg gcctgaatat    780 ccagataaa catctcttcc catggattac cgtgaatcgg gcgtgattcc agacgggtca    840
taatcagatt gtggttgcgc agtaccagca acgcttcaac cagcgcaccg gcttgttgcc    900
cggtcgccat taacaacgtg gttttcgccg gaacctgatc agacacgtta atggctttac    960
gcgccaacac cacaaatcgg gtgaagtttt gtcgctgatt tgcttcaata cgctccagta   1020
cctgcaaacc gtacaaagtg ccgccagctt cgcttcccaa cgcagcaaca tgcggtgatt   1080
ttgcctgtgc aaccttttcc attgccgcag acgtactttc ggtatattca atcttccagt   1140
gcggataacg attaagg                                                   1157
```